United States Patent [19]
Takeuchi et al.

[11] Patent Number: 6,080,293
[45] Date of Patent: Jun. 27, 2000

[54] ELECTROLYTIC TEST MACHINE

[75] Inventors: Toshihiro Takeuchi; Tadashi Imanaka, both of Wako; Shigeru Akutsu, Kiryu; Keiji Kiuchi, Kiryu; Yoshio Takada, Kiryu, all of Japan

[73] Assignees: Honda Giken Kogyo Kabushiki Kaisha, Tokyo; Mitsuba Corporation, Gunma, both of Japan

[21] Appl. No.: 08/876,094

[22] Filed: Jun. 10, 1997

[30] Foreign Application Priority Data

Jun. 10, 1996 [JP] Japan .................................... 8-147069
Apr. 1, 1997 [JP] Japan .................................... 9-082982

[51] Int. Cl.$^7$ .................................................. G01N 27/26
[52] U.S. Cl. ........................ 204/400; 204/278; 204/434; 205/516; 205/775; 205/775.5; 205/776.5; 205/777; 205/790.5; 205/791; 205/791.5
[58] Field of Search ..................... 204/400, 434, 204/266, 278; 205/775, 778.5, 779, 779.5, 780, 791, 791.5, 790.5, 510, 516, 537, 775.5, 776.5, 777

[56] References Cited

U.S. PATENT DOCUMENTS

| | | | |
|---|---|---|---|
| 3,223,598 | 12/1965 | Jacky et al. | 205/791 |
| 3,506,560 | 4/1970 | Grangaard | 204/263 |
| 3,770,593 | 11/1973 | Dick | 205/791 |
| 3,996,118 | 12/1976 | Sanders | 205/516 |
| 4,035,279 | 7/1977 | Lohrberg et al. | 204/266 |
| 4,592,814 | 6/1986 | Vaughn | 204/266 |
| 4,595,465 | 6/1986 | Ang et al. | 204/266 |
| 4,737,255 | 4/1988 | Arruda et al. | 204/400 |
| 5,160,596 | 11/1992 | Keller | 204/266 |

FOREIGN PATENT DOCUMENTS

| | | |
|---|---|---|
| 0107491 | 5/1984 | European Pat. Off. . |
| 0465347 | 1/1992 | European Pat. Off. . |
| 3114826 | 11/1982 | Germany . |
| 7-195612 | 8/1995 | Japan . |
| 93/19365 | 9/1993 | WIPO . |
| 94/19673 | 9/1994 | WIPO . |

*Primary Examiner*—T. Tung
*Attorney, Agent, or Firm*—Arent Fox Kintner Plotkin & Kahn PLLC

[57] ABSTRACT

An electrolytic test machine is used for a corrosion resistance test for a test material comprised of a metal blank and a coating film. The electrolytic test machine is constructed so that an adverse influence, due to chlorine gas generated during a test, can be inhibited. The electrolytic test machine includes an electrolytic cell in which an aqueous solution of NaCl is stored so that a test material is immersed in the aqueous solution of NaCl. An electrode is immersed in the aqueous solution of NaCl. A DC power source supplies electric current between the electrode and the test material. A chlorine gas treating device collects chlorine gas which is generated with electrolysis of the aqueous solution of NaCl and which is released out of the aqueous solution of NaCl along with the aqueous solution of NaCl. The chlorine gas treating device includes a treating pipe line, a suction pump mounted on the treating pipe line, and a chlorine gas purifying member.

6 Claims, 52 Drawing Sheets

FIG.17
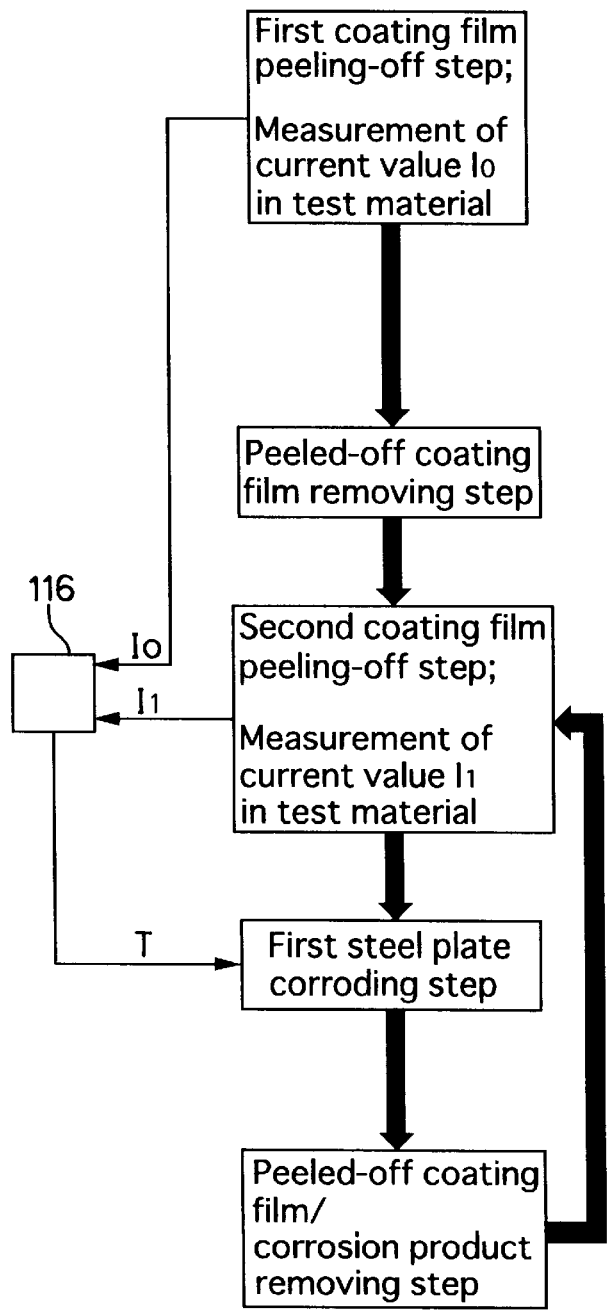
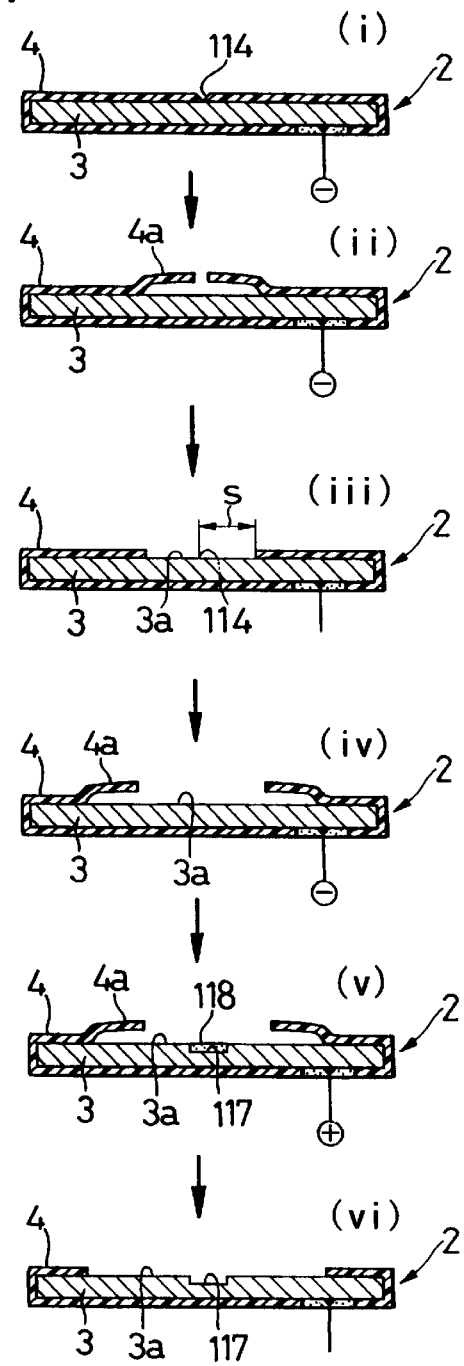

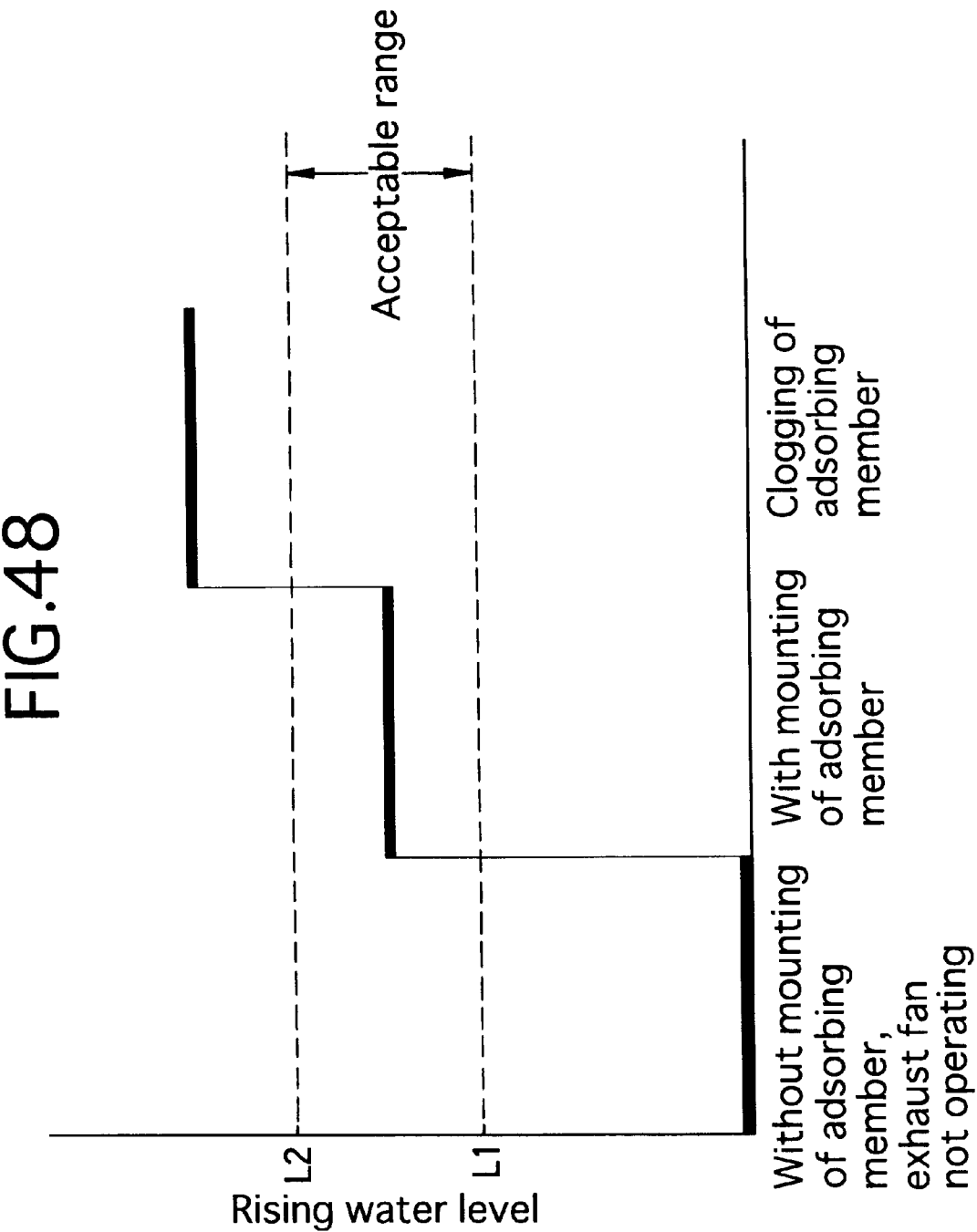

ELECTROLYTIC TEST MACHINE

BACKGROUND OF THE INVENTION

1. Field of the Invention

The present invention relates to an electrolytic test machine, and in particular relates to an electrolytic test machine including an electrolytic cell in which an aqueous solution of NaCl is stored so that a test material can be immersed in the aqueous solution of NaCl, an electrode immersed in the aqueous solution of NaCl, and a DC power source for supplying electric current between the electrode and the test material.

2. Description of the Related Art

Such an electrolytic test machine is used, for example, for a cathode peel-off test for a coating film on a test material (see Japanese Patent Application Laid-open No.195612/1995). This test is carried out in such a manner that the polarity of the test material is set at a cathode, while the polarity of the electrode is set at an anode. Therefore, a chlorine gas is produced on the side of the electrode with electrolysis of the aqueous solution of NaCl.

In this case, such a measure may be contemplated that a chlorine gas treating means collects and treats the chlorine gas that is released out of the aqueous solution of NaCl and flows within the electrolytic cell.

However, if the chlorine gas treating means of the above-described type is used, it is impossible to inhibit the production of HC10 and NaClo in the aqueous solution of NaCl and impossible to inhibit the dissolution of the chlorine gas into the aqueous solution of NaCl.

As a result, a problem arises because the coating film is whitened by the bleaching effects of HClO and NaClO, and the appearance of the coating film is considerably different from a corroded state in a natural environment. Another problem that arises is that the concentration of chlorine in the aqueous solution of NaCl is increased and hence, an irritant odor is generated during replacement of the test material or during replacement of the aqueous solution of NaCl which degrades the working environment.

SUMMARY OF THE INVENTION

Accordingly, it is an object of the present invention to provide an electrolytic test machine, wherein the production of HClO and NaClO in the aqueous solution of NaCl and the dissolution of the chlorine gas into the aqueous solution of NaCl can be inhibited to the maximum amount.

To achieve the above object, according to a first aspect and feature of the present invention, there is provided an electrolytic test machine comprising an electrolytic cell in which an aqueous solution of NaCl is stored so that a test material can be immersed in the aqueous solution of NaCl. An electrode is immersed in the aqueous solution of NaCl. A DC power source supplies electric current between the electrode and the test material. The electrolytic test machine further includes a chlorine gas treating device which collects, out of the aqueous solution of NaCl, chlorine gas which is generated around the electrode with electrolysis of the aqueous solution of NaCl along with the aqueous solution of NaCl.

With the above arrangement, the chlorine gas generated in the aqueous solution of NaCl can be immediately collected and treated. Therefore, the diffusion of the chlorine gas into the aqueous solution of NaCl in the electrolytic cell can be suppressed. Thus, the production of HClO and NaClO in the aqueous solution of NaCl in the electrolytic cell is inhibited, the dissolution of the chlorine gas into the aqueous solution of NaCl is inhibited to the utmost and the decomposition of the collected chlorine gas is realized.

In addition, according to the present invention, the chlorine gas treating device includes a treating pipe line having a suction port disposed in an electrode immersion zone within the electrolytic cell, a suction pump disposed in the treating pipe line, and a chlorine gas purifying member disposed in the treating pipe line and having a catalyst which has a function to decompose NaClO and HClO which are reaction products in a test.

With the above arrangement, it is possible to reliably perform the decomposition of NaClO and HClO which are reaction products.

Further, according to the present invention, the electrolytic test machine further includes an NaOH introducing device, mounted in the electrolytic cell, for introducing NaOH to the electrode immersion zone. NaOH is produced in the test material immersion zone within the electrolytic cell.

With the above arrangement, it is possible to promote the decomposition of the collected chlorine gas and to prolong the life of the catalyst.

The above and other objects, features and advantages of the invention will become apparent from the following description of the preferred embodiment taken in conjunction with the accompanying drawings.

BRIEF DESCRIPTION OF THE DRAWINGS

FIG. 17 is an illustration for explaining a corrosion resistance test:

FIG. 48 is a graph illustrating the relationship between the situation of the exhaust system and the liquid level;

DETAILED DESCRIPTION OF THE PREFERRED EMBODIMENTS

A. Summary of Electrolytic Test Machine

Figure 1:
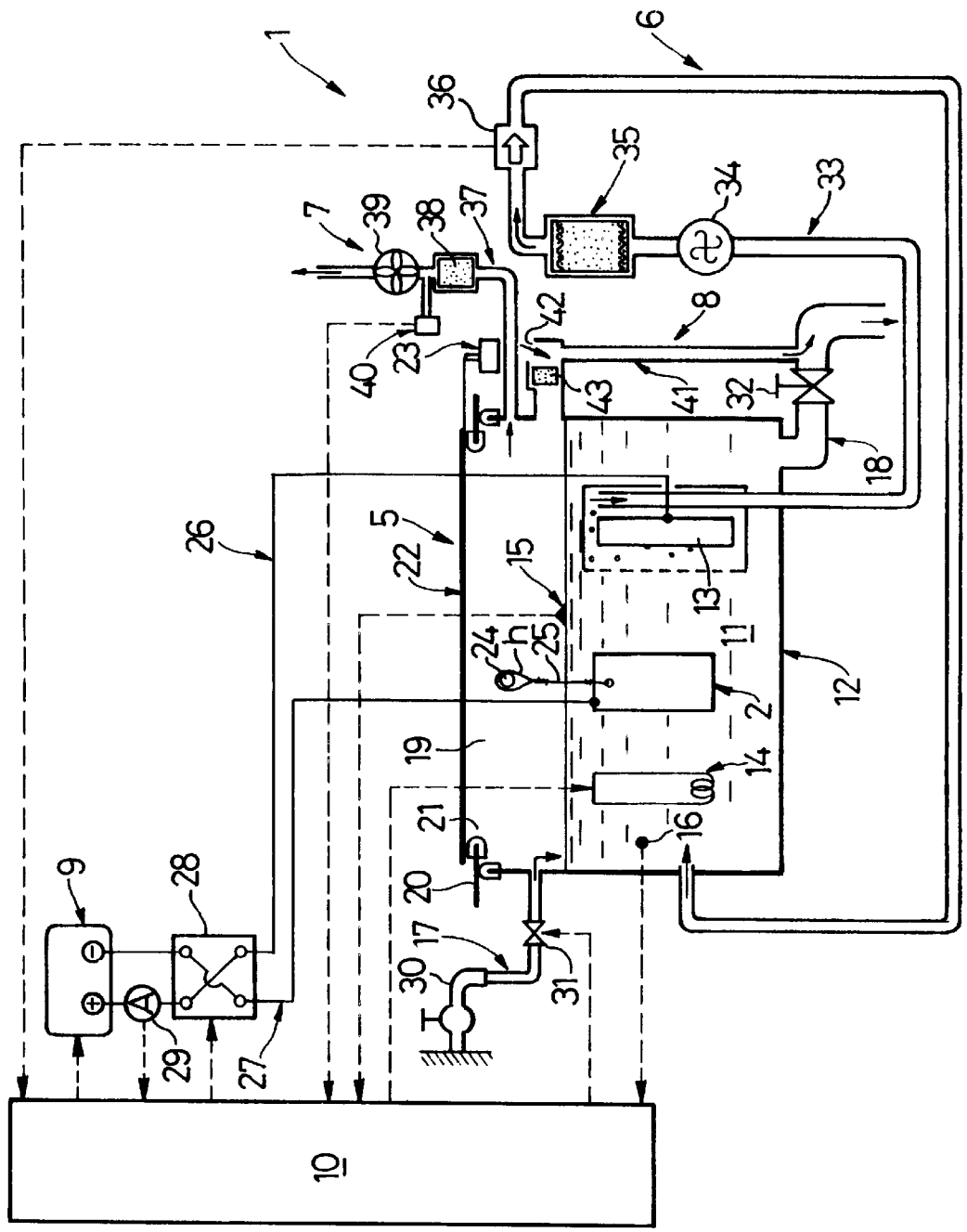
FIG. 1 is a diagrammatic illustration of an electrolytic test machine.
Figure 2:
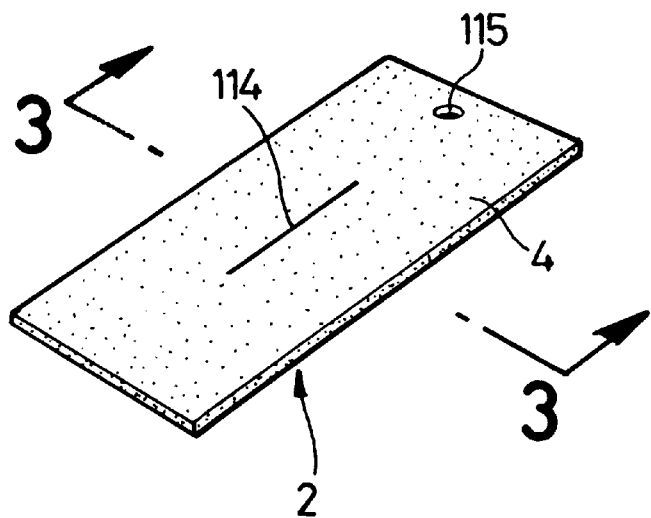
FIG. 2 is a perspective view of a test material.
Figure 3:
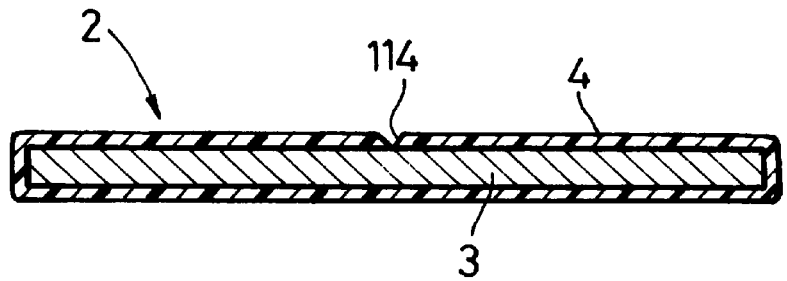
FIG. 3 is a sectional view taken along a line 3—3 in FIG. 2.

An electrolytic test machine 1 shown in FIG. 1 is used for a corrosion test for a test material 2 shown in FIGS. 2 and 3. The test material 2 is comprised of a steel plate 3 such as a metal blank, and a coating film 4 formed on the entire steel plate 3.

The electrolytic test machine 1 includes an electrolytic device 5. A harmful gas treating device 6, an exhaust device 7 and an overflow device 8 having a sucking function are mounted to the electrolytic device 5.

The electrolytic device 5 includes a DC power source 9 (a constant-voltage power source having a highest voltage of 20 V and a maximum current of 50 A), a computer programmed control unit 10, an electrolytic cell 12 in which an aqueous solution of NaCl 11 as an electrolytic liquid is stored, a plate-like carbon electrode 13 which is a consumable electrode as an electrolytic electrode immersed in the aqueous solution 11 of NaCl, an electric heater 14, a water level sensor 15, a temperature sensor 16, a water supply pipe line 17 and a drainage pipe line 18.

Because an aqueous solution of NaCl 11 is used, a chlorine gas is generated with the electrolysis of the aqueous solution of NaCl 11 during a test. To cope with this, an upward opening 19 in the electrolytic cell 12 is covered and sealed with a cover 20 made of a synthetic resin. An upward opening 21 in the cover 20 is used for placing and removing the test material 2 into and out of the electrolytic cell 12. The opening 21 is sealed with an openable and closable lid 22. The lid 22 and cover 20 tightly close the electrolytic cell 12.

An electric power cylinder 23, which is a drive source for opening and closing the lid 22, is supplied with an electric current from an external power source.

The test material 2 is hung from a support bar 24 in the electrolytic cell 12 by a string 25 made of a synthetic resin, and is immersed into the aqueous solution of NaCl 11. The carbon electrode 13 and the steel plate 3 of the test material 2 are connected to the DC power source through energizing lines 26 and 27. A polarity switch-over relay 28, as a polarity switch-over means, is connected to the energizing lines 26 and 27. An ammeter 29 is connected to one of the energizing lines 27 between the DC power source 9 and the polarity switch-over relay 28.

The DC power source 9 is controlled at a constant voltage by the control unit 10 and also controlled in an ON/OFF manner. The polarity switch-over relay 28 is controlled so that the polarity of the steel plate 3 of the test material 2 is alternately switched over from positive to negative polarity or vice versa. In this case, the polarity of the carbon electrode 13 is, of course, opposite from that of the steel plate 3. The ammeter 29 inputs an electric current flowing across the carbon electrode 13 and the steel plate 3 to the control unit 10.

The water supply pipe line 17 communicates at one end thereof with a cock 30 of a water service which is a water supply source and at the other end with the electrolytic cell 12. A solenoid valve 31 is mounted at an intermediate portion of the water supply pipe line 17. The opening and closing of the solenoid valve 31 are controlled through the control unit 10 by a detection signal from the water level sensor 15. The drainage pipe line 18 communicates with a bottom of the electrolytic cell 12 and includes a manual cock 32.

The electric heater 14 is supplied with an electric current from the external power source and is controlled in an ON/OFF manner through the control unit 10 by detection signals from the water level sensor 15 and the temperature sensor 16.

The chlorine gas treating device 6 includes a treating pipe line 33 extending from the electrolytic cell 12. An electric suction pump 34, a chlorine gas purifying member 35 and an abnormal-point detecting flow rate sensor 36 are mounted in the treating pipe line 33. The suction pump 34 is supplied with an electric current from the external power source.

The exhaust device 7 includes an exhaust pipe line 37 extending from the electrolytic cell 12. A chlorine gas adsorbing member 38, an electric exhaust fan 39 and a detecting means 40 for detecting an abnormality generation are provided in the exhaust pipe line 37. The exhaust fan 39 is supplied with an electric current from the external power source.

The overflow device 8, having a sucking function, is comprised of an overflow pipe 41 extending from the electrolytic cell 12, a gas intake port 42 provided in the overflow pipe 41, and a chlorine gas (harmful gas) adsorbing member 43 disposed in an inlet of the overflow pipe 41.

B. Entire structure of Electrolytic Test Machine (FIGS. 4 to 9)

The electrolytic test machine 1 is constructed into a movable type, wherein the side thereof as viewed in FIGS. 4 to 6, 8 and 9 is a front portion X. Therefore, testing personnel conducts a testing operation from the front portion X.

As shown in FIGS. 5 to 9, the electrolytic test machine 1 includes a rectangular machine base 44. A plurality of casters 45, functioning as traveling wheels, are mounted on a lower surface at the four corners of the machine base 44 in the illustrated embodiment. If the direction a of movement of the machine base 44 is a lengthwise direction, namely, a lateral direction, a tracklng/urging hook 46 is provided on each opposite outer end face of the machine base 44 as viewed in the direction of movement of the machine base 44, namely, on left and right end faces.

Figure 7:
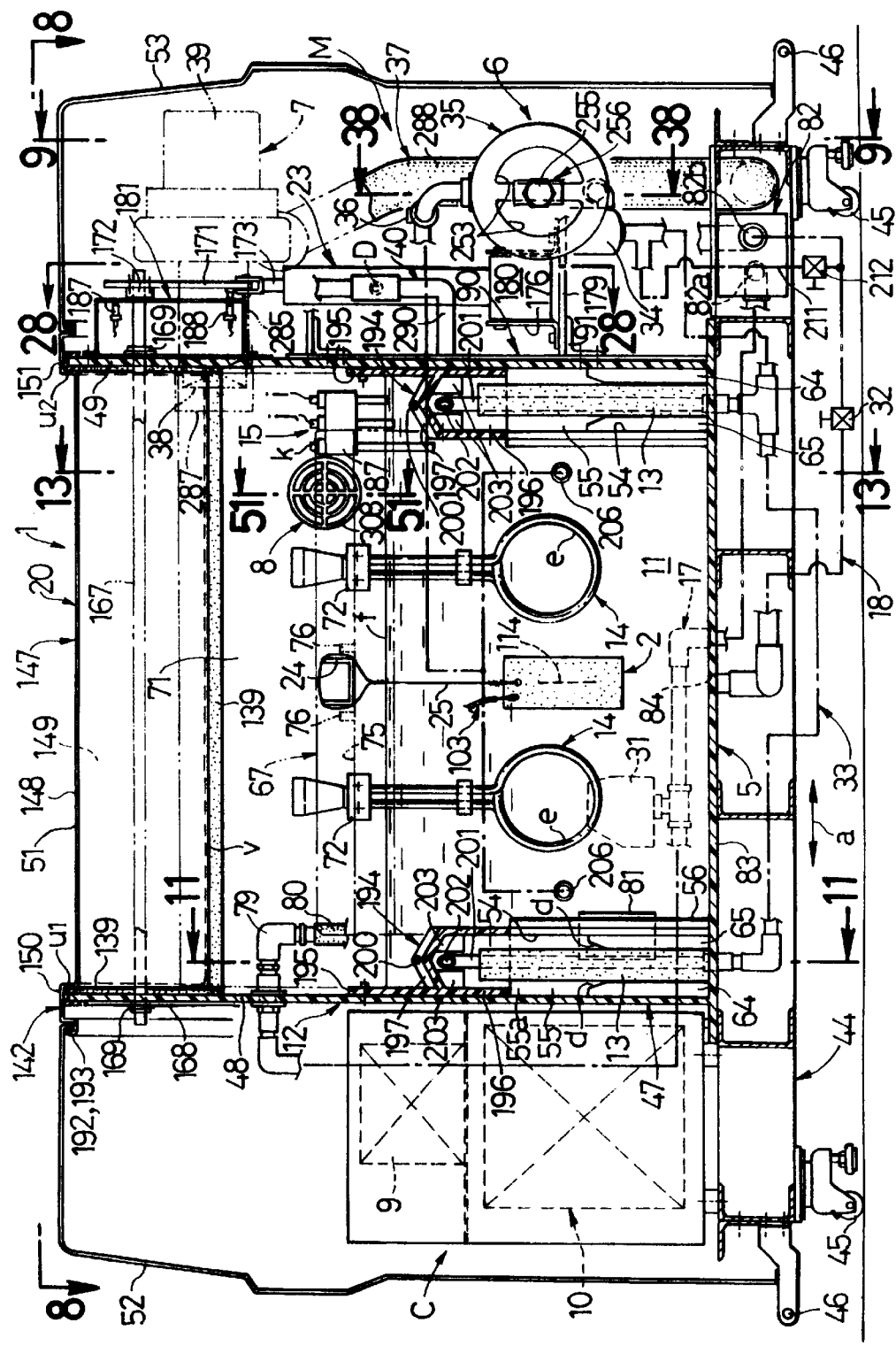
FIG. 7 is a vertical sectional front view of the electrolytic test machine, which corresponds to a sectional view taken along a line 7—7 in FIG. 6.
Figure 8:
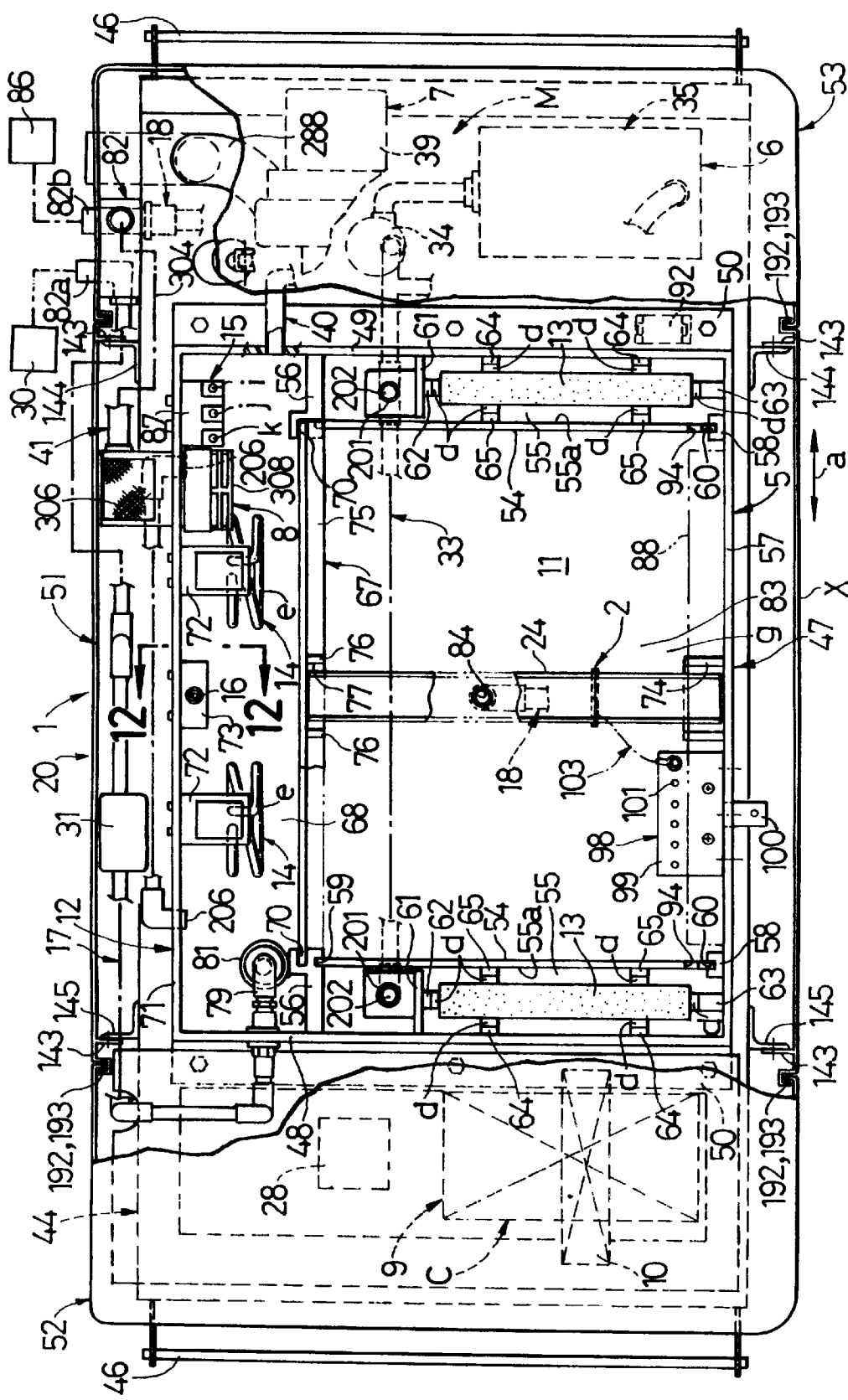
FIG. 8 is a cutaway plan view of an essential portion of the electrolytic test machine, which corresponds to a sectional view taken along a line 8—8 in FIG. 7.

A mechanical section M is disposed on the machine base 44 on one end side, i.e., on the right side as viewed in FIG. 7 and 8 along the direction a of movement of the machine base 44. A box-like electrolytic bell 12 made of a synthetic resin is disposed at a central portion of the machine base. A control section C is disposed on the machine base 44 on the other end side, e.g., on the left side as viewed in FIGS. 7 and 8.

The electrolytic cell 12 is detachably mounted to the machine base 44 through a pair of mounting plates 50 which protrude from lower ends of an outer surface of left and right sidewall portions 48 and 49 of a peripheral wall 47, as shown in FIGS. 7 and 8.

The electrolytic cell 12, the mechanical section M and the control section C are covered respectively with a central cover section 51, a left cover section 52 and a right cover section 53 which constitute a cover 20 made of a synthetic resin. The central cover section 51 covering the electrolytic cell 12 seals the upward opening in the electrolytic cell 12, and has a rectangular opening 21 which is used for placing and removing the test material 2 into and out of the electrolytic cell 12. The lid 22, for opening and closing the opening 21, has a hinge on the side of one end thereof, namely, on the side of a rear portion thereof.

Figure 9:
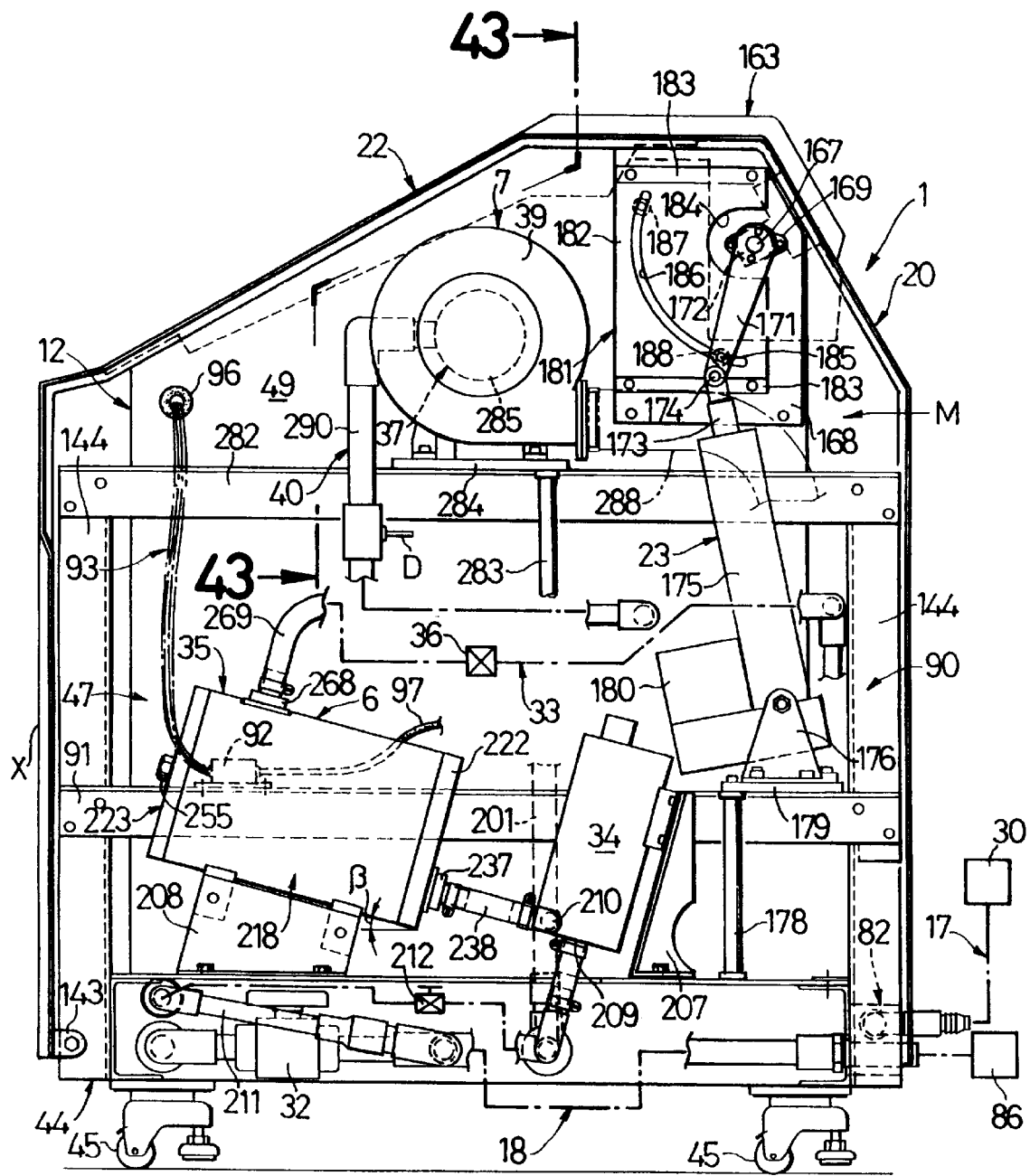
FIG. 9 is a sectional view taken along a line 9—9 in FIG. 7.

As best shown in FIGS. 7 and 9, included in the mechanical section M are an electric power cylinder 23, which is the drive source for opening and closing the lid 22, a suction pump 34 and a chlorine gas purifying device 35 in the chlorine gas treating device 6, an exhaust fan 39 of the exhaust device 7, and the like.

In addition, as best shown in FIGS. 7 and 8, included in the control section C are transformers (not shown), various switches and the like for the suction pump 34 and the exhaust fan 39, in addition to the DC power source 9, the computer programmed control unit 10 and the polarity switch-over relay 28.

With such a construction, the electrolytic cell 12 is independent from the mechanical section M and the control section C. Therefore, it is possible to sufficiently increase the volume of the electrolytic cell 12, thereby moderating the limitation for the size of the test material 2.

The electrolytic cell 12, the mechanical section M and the control section C are independent from one another, resulting in independent maintenance for them.

Further, the electrolytic test machine 1 is of a movable type and therefore, it is easy to transport the test machine 1 into and out of a test room.

Moreover, the relatively large-sized and heavy electrolytic cell 12 is disposed at the central area and therefore, the electrolytic test machine 1 is stable and balanced when moved.

Figure 6:
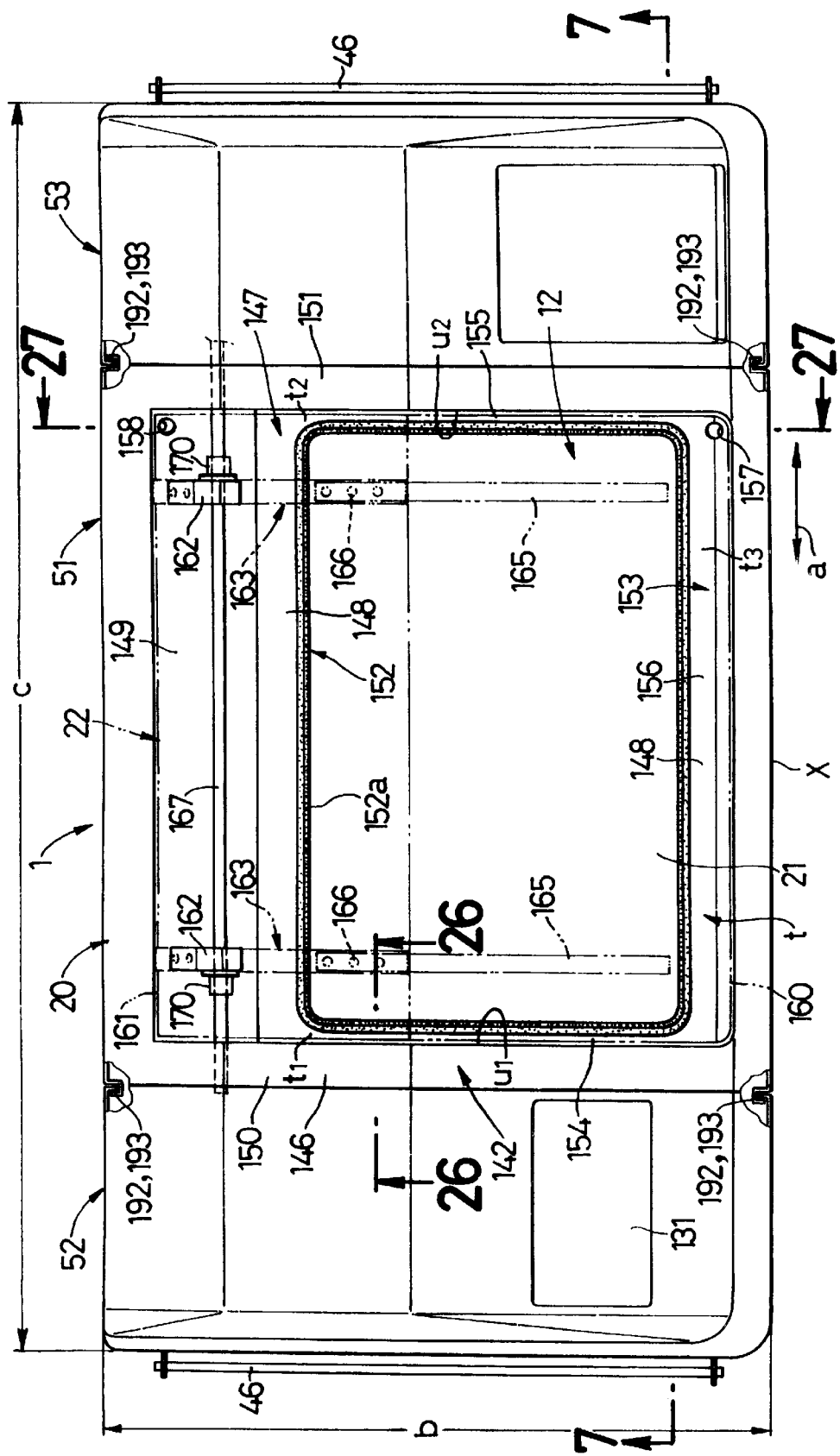
FIG. 6 is a view taken along an arrow 6 in FIG. 5.

Additionally, the electrolytic cell 12, the mechanical section M and the control section C are disposed in a line in the direction a of movement of the electrolytic test machine 1 and therefore, the width dimension perpendicular to the direction a of movement can be easily adjusted to the width dimension of an access port of a ready-made test room. For example, the width b in the electrolytic test machine 1 is set at 800 mm, and the length c can be set at 1,600 mm, as shown in FIG. 6.

C. Structure of Disposition of Carbon Electrode and Electric Heater (FIGS. 7, 8 and 10 to 13)

In a left and lower area within the electrolytic cell 12, an electrode chamber 55 is immersed in the aqueous solution of NaCl 11. The electrode chamber 55 is defined by the peripheral wall 47 of the electrolytic cell 12, and a partition plate 54. The partition plate 54 is opposed to and in proximity to an inner surface of the peripheral wall 47 and is attachable to and detachable from the electrolytic cell 12.

The left sidewall portion 48 of the peripheral wall 47 has a division plate 56, made of a synthetic resin, which forms a rear wall of the electrode chamber 55. A front wall portion 57 of the peripheral wall 47 has a projection 58 which forms a front wall of the electrode chamber 55 and is opposed to the division plate 56. The partition plate 54 is slidably fitted into opposed guide grooves 59 and 60 in the division plate 56 and the protection 58. Therefore, the partition plate 54 forms a right wall of the electrode chamber 55, while the left sidewall portion 48 forms a left wall of the electrode chamber 55.

The plate-like carbon electrode 13 is accommodated within the electrode chamber 55 in a vertical state and in parallel to the partition plate 54. An upper portion of the carbon electrode 13 protrudes above the top end of the partition plate 54. Front and rear end faces of the carbon electrode 13 are clamped by clamping member 62 of a protruding plate 61 of the left sidewall portion 48 and by clamping member 63 of the front wall portion 57. The left and right flat sides of the carbon electrode 13 are clamped by a pair of clamping members 64 of the left sidewall portion 48 and a pair of clamping members 65 of the partition plate 54. The carbon electrode 13 is capable of being set between and withdrawn from between the clamping members 62 to 65. In order to guide the insertion of the electrode 13, a slope d is formed on an upper portion of each of the clamping members on the insertion side of the electrode. The partition plate 54 has a large number of through-holes 66 at locations opposed to the carbon electrode 13 for permitting the aqueous solution of NaCl 11 to be passed therethrough.

In a right lower area within the electrolytic cell 12, another electrode chamber 55, similar to the above-described electrode chamber 55, is defined utilizing the right sidewall portion 49 of the peripheral wall 47. Another plate-like carbon electrode 13, similar to the above-described electrode 13, is accommodated in the other electrode chamber 55. Thus, the distribution of voltage in the test material 2 can be uniform. Components of the right electrode chamber 55 similar to those of the left electrode chamber 55 are designated by like reference characters.

In a rear area within the electrolytic cell 12, a heater chamber 68 is defined by the peripheral wall 47 of the electrolytic cell 12 and a partition plate 67. The partition plate 67 is opposed to and in proximity to the inner surface of the peripheral wall 47 and is attachable to and, detachable from the electrolytic cell 12. The partition plate 67 has a plurality of through-holes 69 for permitting the aqueous solution of NaCl 11 to be passed therethrough, and is slidably fitted into opposed guide grooves 70 defined in the pair of division plates 56 of both electrode chambers 55. Therefore, a front wall of the heater chamber 68 is formed by the partition plate 67 and the pair of division plates 56, A rear wall of the heater chamber 68 is formed by a rear wall portion 71 of the peripheral wall 47 and left and right walls of the heater chamber 68 are formed by the left and right sidewall portions 48 and 49.

As best shown in FIGS. 7, 8, 12 and 13, the pair of electric heaters 14 are accommodated within the heater chamber 68 at a predetermined distance in left and right directions and with their coiled portions e turned downwards. An upper portion of each of electric heaters 14 is supported by a support 72 mounted on the rear wall portion 71 above the liquid level f of the aqueous solution of NaCl 11. The temperature sensor 16, for detecting the temperature of the aqueous solution of NaCl 11, is disposed between both electric heaters 14. The temperature sensor 16 has a lower end portion immersed in the aqueous solution of NaCl 11, and an upper portion supported by a support 73 mounted on the rear wall portion 71 above the liquid level f.

Within the electrolytic cell 12, an area surrounded by the three partition plates 54 and 67 and the front wall portion 57 is used as a space g for placement of the test material 2.

Figure 13:
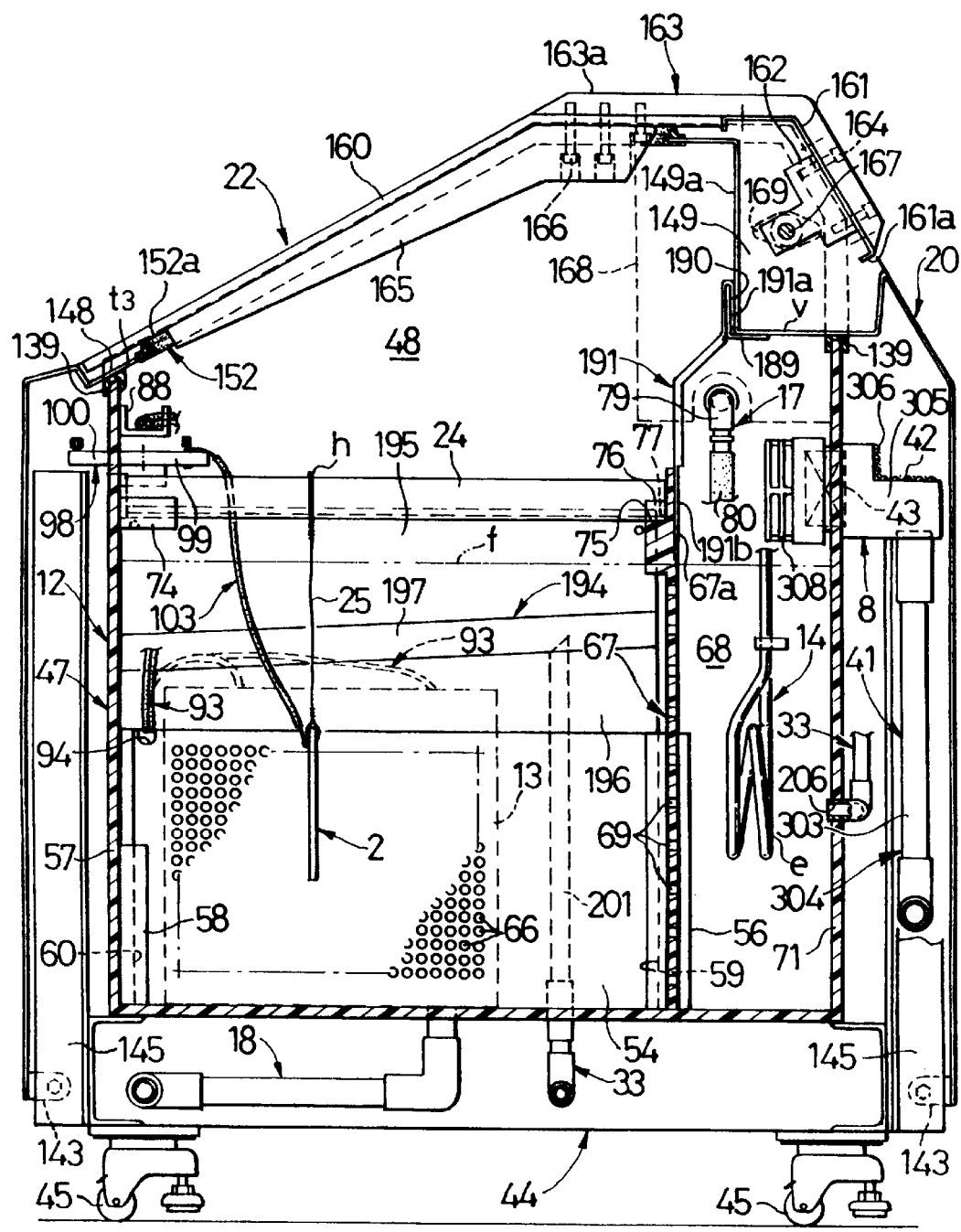
FIG. 13 is a sectional view taken along a line 13—13 in FIG. 7.

As shown in FIGS. 7, 8 and 13, a U-shaped support 74 is projectingly provided on an inner surface of the front wall portion 57, so that it is located above the liquid level f of the aqueous solution of NaCl 11 and is located at a laterally intermediate portion. A recess 77 is defined by a pair of protrusions 76 located at a stepped portion 75 of the partition plate 67 adjacent the heater chamber 68. Thus, the recess 77 is opposed to the support 74. The test material supporting bar 24, made of a synthetic resin and having a channel-like shape, is detachably suspended between the U-shaped support 74 and the recess 77. As shown in FIGS. 1 and 13, the test material 2 is immersed into the aqueous solution of NaCl 11 in such a manner that it is hung from the supporting bar 24 through a looped portion h of a string of a synthetic resin attached to the test material 2.

If both carbon electrodes 13 and both electric heaters 14 are accommodated within the electrode chambers 55 and the heater chamber 68 as described above, the contact of the electrodes 13 and the electric heaters 14 with the test material 2 can be reliably prevented, and both carbon electrodes 13 and both electric heaters 14 can be protected. Each of the partition plates 54 and 67 are in proximity to the peripheral wall 47 of the electrolytic cell 12 and moreover, each of the electrode chambers 55 and the heater chamber 68 uses a portion of the peripheral wall 47 as a portion of the chamber wall. Therefore, the space g for placement of the test material 2 can be made wider, as compared with when another partition plate is used in place of the peripheral wall 47. Each of the partition plates 54 and 67 can be removed from the electrolytic cell 12 and each of the carbon electrodes 13 can be removed from the electrolytic cell 12. Therefore, the partition plates 54 and 67 and the carbon electrodes 13 cannot become obstacles in carrying out maintenance, for example, washing the inside of the electrolytic cell 12, resulting in easy maintenance of the cell 12. Since each of the carbon electrodes 13 is clamped by the peripheral wall 47 and the partition plate 54, the structure of supporting the carbon electrode 13 is simple and secure. Also, since each of the electric heaters 14 is attached to the fixed peripheral wall 47, the structure of attaching the electric heater 14 is secure. The three partition plates 54 and 67 may be formed into a U-shaped integral configuration.

D. Water-supply and Discharge Structure of Electrolytic Cell (FIGS. 7, 8, 10, 13 and 14)

Figure 10:
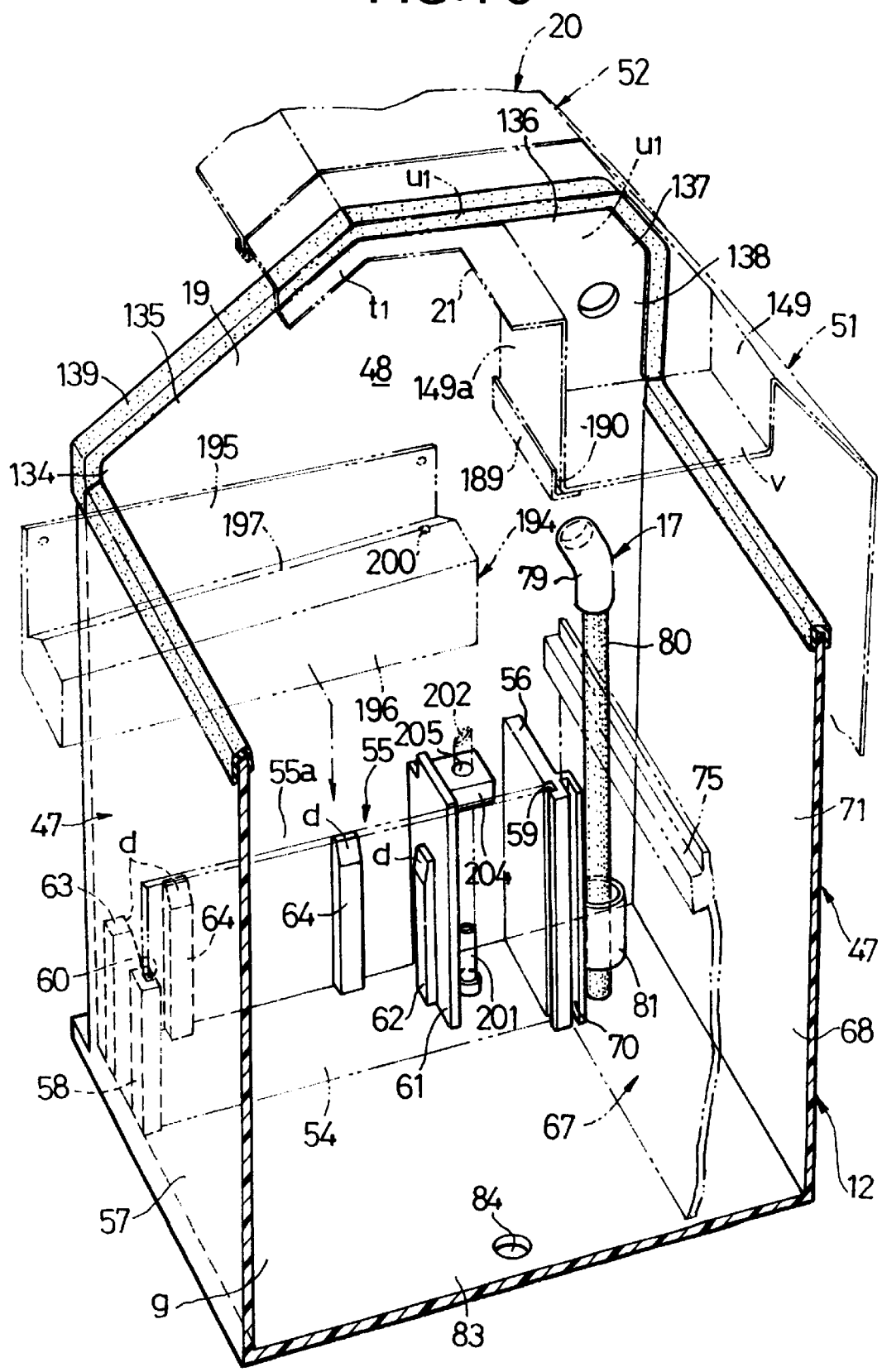
FIG. 10 is a perspective view illustrating the relationship among an electrolytic cell, a cover and a hood.

Above the heater chamber 68, an L-shaped water supply pipe 79, made of a synthetic resin pipe material, in the water supply pipe line 17 is disposed in the left sidewall portion 48 of the electrolytic cell 12 with its outlet turned downwards. A tube 80, made of a soft synthetic resin, is attached to the water supply pipe 79, as best shown in FIG. 10, and has a lower end portion loosely inserted into a retaining sleeve 81 made of a synthetic resin. The sleeve 81 is mounted to a rear surface of the division plate 56 adjacent the heater chamber 68. The retaining sleeve 81 prevents the lower end portion of the tube 80 from being unnecessarily swung during supplying of water. The tube 80 can be withdrawn from the retaining sleeve 81 and used for washing the electrolytic cell 12.

Figure 14:
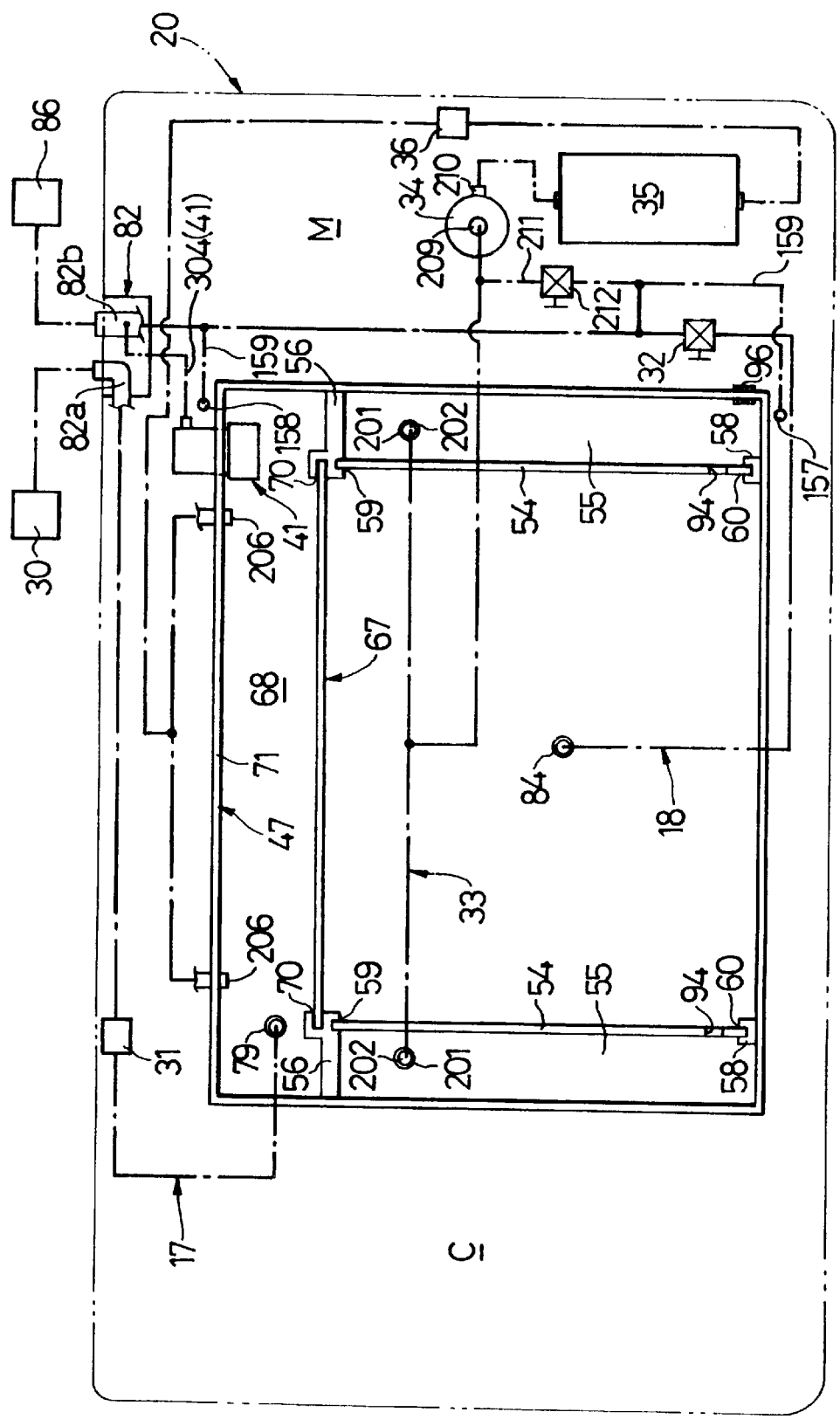
FIG. 14 is an illustration of a piping in the electrolytic test machine.

As best shown in FIGS. 8 and 14, half of the water supply pipe line 17, on the side of the water supply pipe 79, is connected to a water supply portion 82a of a water dispensing block 82, which is mounted on the machine base 44 via outer surfaces of the left sidewall portion 48 and the rear wall portion 71, and half of the supply pipe line 17 on the side of the cock 30 for water service is connected to the water supply portion 82a. In the half of the water supply pipe line 17 on the side of the water supply pipe 79, a solenoid valve 31 is mounted at an intermediate portion thereof. The preparation of the aqueous solution of NaCl 11 is carried out within the electrolytic cell 12 after supplying water to the electrolytic cell 12.

A drainage port 84 is opened in a central portion of a bottom wall 83 of the electrolytic cell 12. A drainage pipe line 18, made of a synthetic resin pipe material, is connected to the drainage port 84. Half of the drainage pipe line 18, on the side of the drainage port 84, is passed through the inside of the machine base 44 and connected to a drainage portion 82b of the water dispensing block 82. Half of the drainage pipe line 18 on the side of a drainage channel 86 is connected to the drainage portion 82b. In the half of the drainage pipe line 18 on the side of the drainage port 84, the manual cock 32 is mounted at an intermediate portion thereof.

E. Control of Water Level of Electrolytic Cell (FIGS. 7 and 8)

The water level sensor 15, for controlling the amount of the aqueous solution of NaCl 11, is disposed at the right end of the inner surface of the rear wall portion 71 of the electrolytic cell 12. The water level sensor 15 includes first, second and third detecting elements i, j and k extending vertically and a level of their lower ends is different from one another. These detecting elements are supported on a support 87 mounted on the rear wall portion 71 and located above the liquid level f of the aqueous solution of NaCl 11. The lower end of the first detecting element i lies at a highest position. The lower end of the third detecting element k lies at a lowest position and the lower end of the second detecting element j lies at a middle position between both the lower ends of the first and third detecting elements i and k.

During supplying of water to the electrolytic cell 12, the first and third detecting elements i and j are non-conducting therebetween, and the solenoid valve 31 is controlled into an opened state by the control unit 10. If the liquid level f rises up to the lower end of the first detecting element i, the first and third detecting elements i and j are brought into conduction therebetween, and the solenoid valve 31 is controlled into a closed state by the control unit 10. This causes the water supply to be stopped. If the liquid level f is low and spaced apart from the lower end of the first detecting element i during a test, the first and third detecting elements i and j are brought into non-conducting therebetween, and the solenoid valve 31 is brought into an opened state, thereby permitting water to be supplied. In this manner, the amount of aqueous solution of NaCl 11 is usually controlled by the first detecting element i.

On the other hand, if water is not supplied even if the liquid level f is spaced apart from the lower end of the first detecting element I, because the first detecting element i fails to operate in the test, the second and third detecting elements j and k are brought into non-conduction therebetween when the liquid level f is lower and is spaced apart from the lower end of the second detecting element j. The DC power source 9 is therefore controlled into an OFF state by the control unit 10. This causes electric current supplied to the carbon electrodes 13 and the test material 2 to be cut off, thereby stopping the test.

The second and third detecting elements j and k are also used for the control of both electric heaters 14. More specifically, if the aqueous solution of NaCl 11 is in a defined amount, the lower ends of the second and third detecting elements j and k are located in the aqueous solution of NaCl 11, and the second and third detecting elements j and k are in conduction therebetween. Hence, both the electric heaters 14 are controlled into energized states by the control unit 10. For example, if the liquid level f is spaced apart from the lower end of the second detecting element j, the second and third detecting elements j and k are brought into non-conduction therebetween. Hence, both electric heaters 14 are controlled into energization-stopped states by the control unit 10.

F. Structure of Wiring of Carbon Electrode and Energizing Terminal Base for Test Material (FIGS. 8, 9, 11, 13 and 15)

In the front wall portion 57 of the electrolytic cell 12, a receiving member 88, made of a synthetic resin, having a channel-like configuration is fixed to extend laterally above the U-shaped support 74.

As best shown in FIGS. 8 and 9, a vertical and quadrilateral frame 90 in the machine base 44 extends the outer surface of the right sidewall portion 49 of the electrolytic cell 12. A terminal box 92 is fixed to an upper surface of a lower angle member 91 which extends longitudinally of the frame 90.

Figure 11:
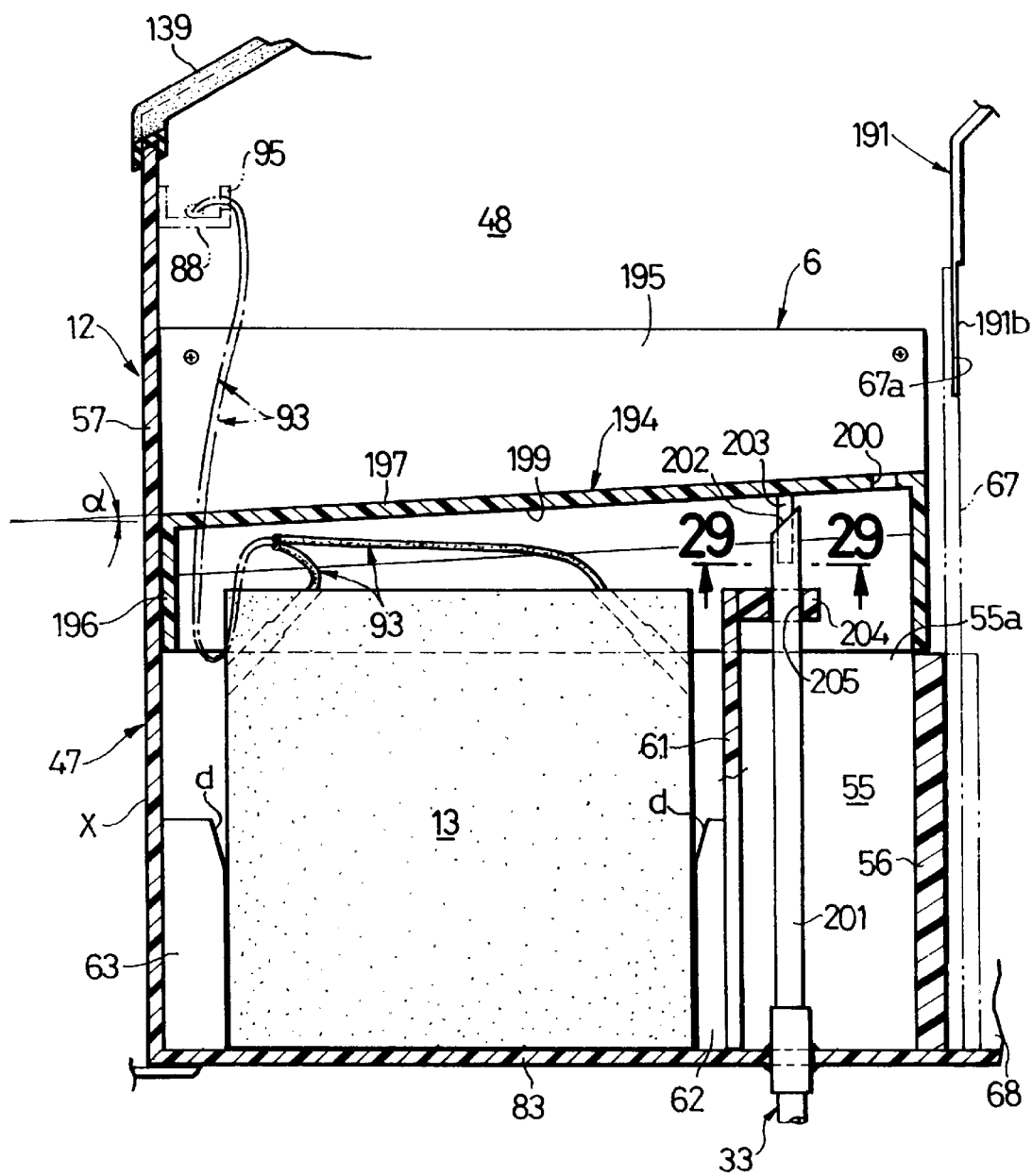
FIG. 11 is a sectional view taken along a line 11—11 in FIG. 7.
Figure 12:
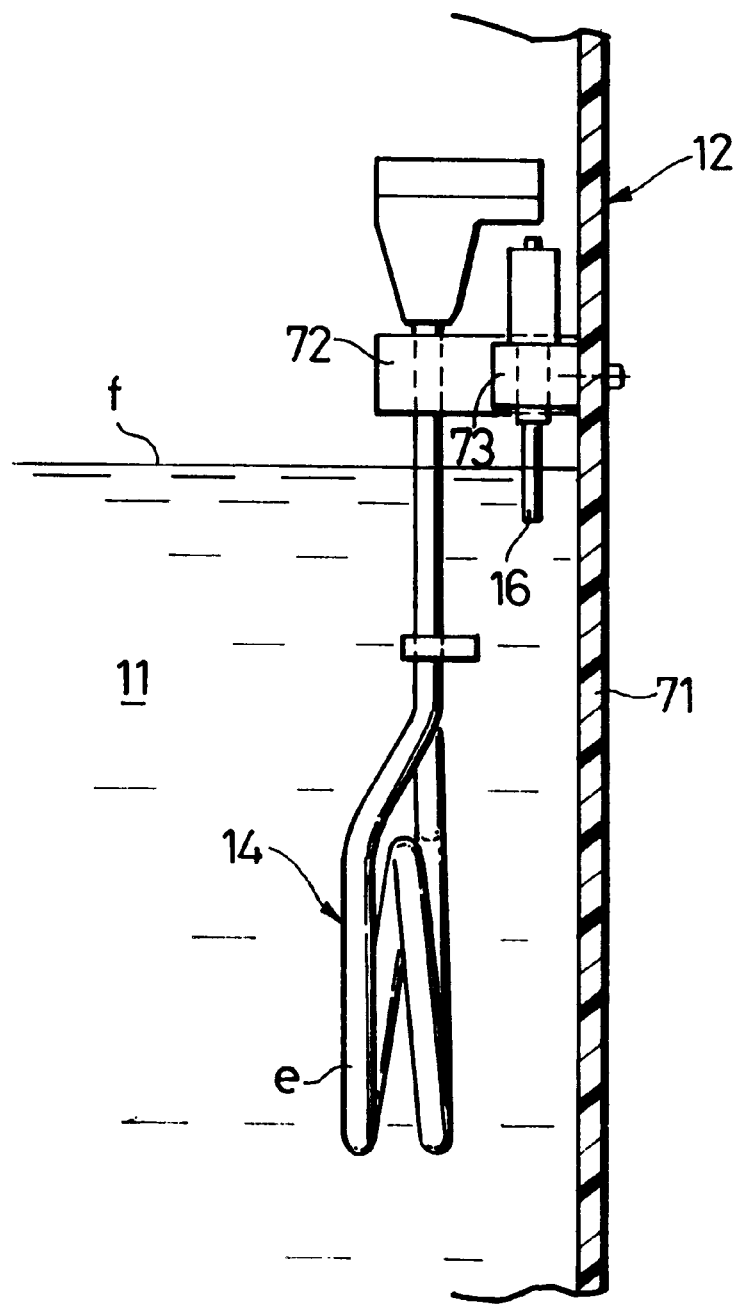
FIG. 12 is a sectional view taken along a line 12—12 in FIG. 8.
Figure 15:
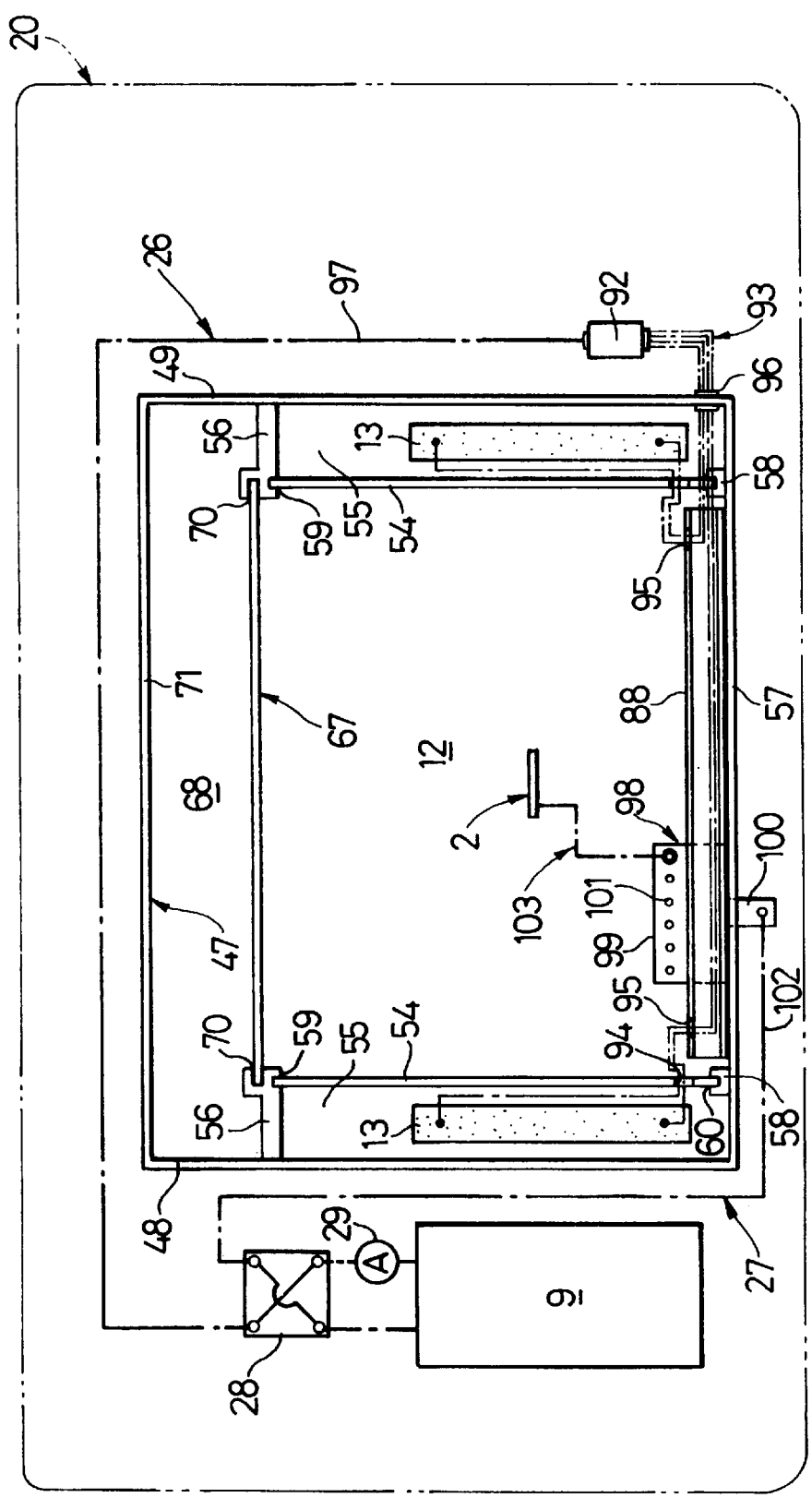
FIG. 15 is an illustration of a wiring in the electrolytic test machine.

Referring to FIGS. 11, 13 and 15, feeder wires 93 are connected to front and rear sides of the upper portions of the left and right carbon electrodes 13, respectively. The two feeder wires 93 of each carbon electrode 13 are drawn to the outside of the electrode chamber 55 through a notch 94 of each partition plate 54. As shown in FIGS. 9 and 15, the feeder wires 93 are passed into the inside of the receiving member 88 from notches 95 of the receiving members 88, where they are collected into four wires. The feeder wires 93 are drawn through a grommet 96 of the right sidewall portion 49 to the outside of the electrolytic cell 12 and connected to connection terminals of the terminal box 92. Main 97 connected to the connection terminals of the terminal box 92 is drawn from the terminal box 92. The main 97 is extended along the outer surfaces of the right sidewall portion 49, the rear wall portion 71 and the left sidewall portion 48 of the electrolytic cell 12, and connected to DC power source 9 through the polarity switch-over relay 28. The feeder wires 93, the terminal box 92 and the main 97 constitute one of the energizing line 26.

Referring again to FIGS. 8, 13 and 15, an energizing terminal base 98, made of titanium, used for connection to the test material 2 is mounted on the front wall portion 57 of the electrolytic cell 12 to lie below the receiving member 88 and in the vicinity of the U-shaped support 74. A first connecting portion 99 of the energizing terminal base 98 with the test material 2 is disposed within the electrolytic cell 12, and a second connecting portion 100 of the energizing terminal base 98 with the DC power source 9 is disposed outside the electrolytic cell 12. A plurality of connecting bores 101, each having an internal thread, are defined in the first connecting portion 99, so that they correspond to the plurality of feeder wires 103 connected to a plurality of test materials 2. A main 102 is connected to the second connecting portion 100. The main 102 is extended along the outer surfaces of the front wall portion 57 and the left sidewall portion 48 and connected to the DC power source 9 through the polarity switch-over relay 28. The feeder wires 103, the energizing terminal base 98 and the main 102 constitute the other energizing line 27.

Figure 16:
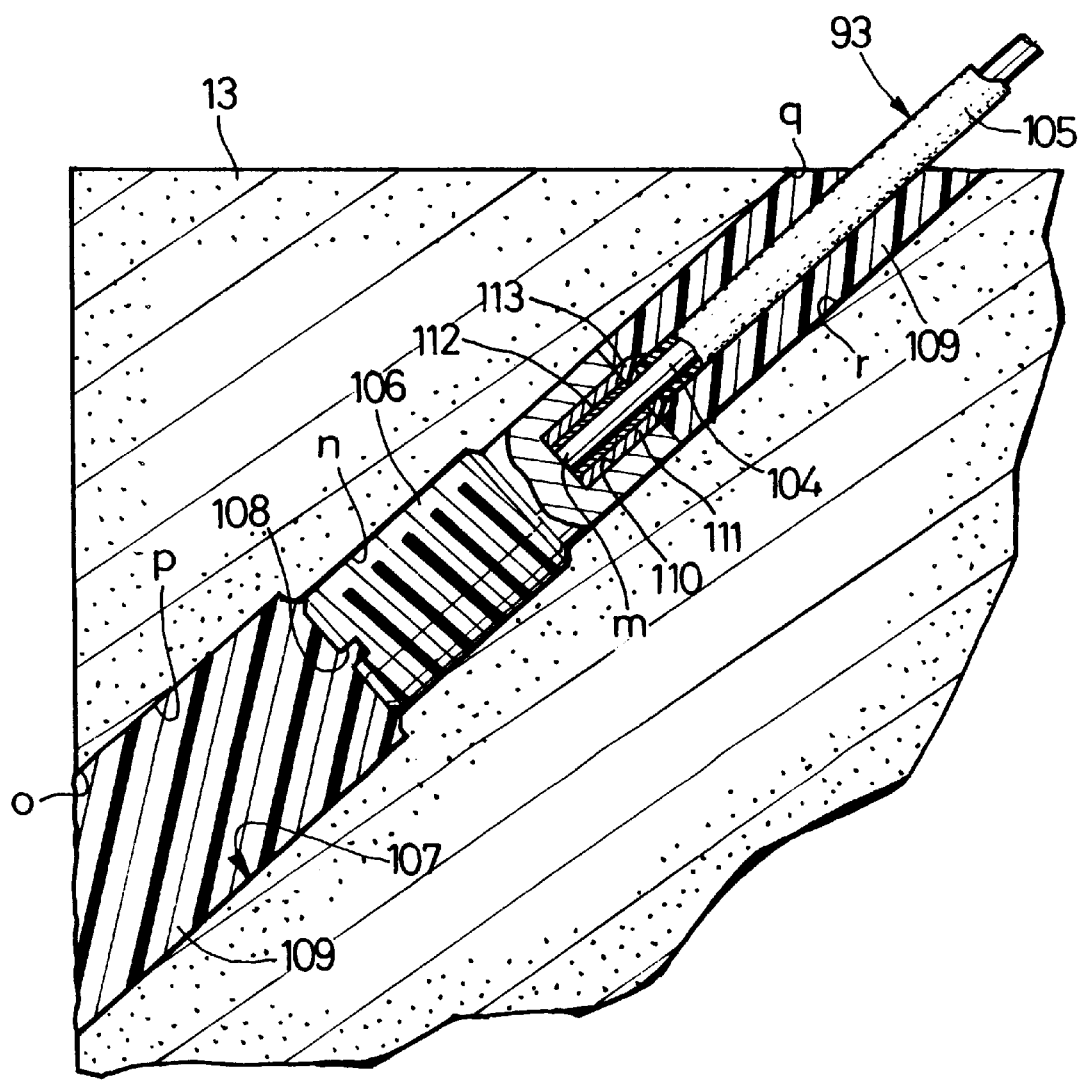
FIG. 16 is a sectional view showing the structure of a connection of a carbon electrode with an electric feeder wire.

G. Structure of Connection of Carbon Electrode with Feeder Wires (FIG. 16)

Each of the feeder wires 93 has a conductor 104 and a corrosion-resistant insulating coating layer 105. A terminal end m of the conductor 104 protrudes from the corrosion-resistant insulating coating layer 105 of the feeder wire 93. The terminal end m is connected to a conductive connecting bolt 106. A connecting bore 107 is defined in a corner of the carbon electrode 13 and has a threaded portion n. The connecting bolt 106 is threadedly engaged with the threaded portion n.

The connecting bore 107 may be a blind bore, but in the illustrated embodiment, the connecting bore 107 is a through-bore extending obliquely and vertically. The feeder wire 93 and the connecting bolt 106 are inserted into the connecting bore 107 through a lower opened end o of the connecting bore 107. To this end, the connecting bolt 106 has a tool, e.g., an engage portion for engagement with a minus screwdriver, namely, an engage groove 108, at an end opposite from an end to which the feeder wire 93 is connected.

A seal material 109, such as a silicone, is filled in a void space p of the connecting bore 107. The void space p is located between the lower opened end o of the connecting bore 107 and an end face of the connecting bolt 106 on the side of the engage groove 108. A seal material 109, similar to the above seal material, is also filled in a void space r of the connecting bore 107. The void space r is located between an upper opened end g and an end face of the connecting bolt 106, from which the feeder wire 93 extends. The void space r surrounds the insulating coating layer 105 of the feeder wire 93.

The connection of the connecting bolt 106 with the terminal end m of the conductor 104 of the feeder wire 93 is as follows; The connecting bolt 106 is formed of titanium which enhances corrosion resistance of the connecting bolt 106. The connecting bolt 106 has a blind bore 110 which is open at one end face of the bolt. A hollow tubular member 111 made of a copper alloy, e.g., brass in the illustrated embodiment, is press-fitted into the blind bore 110. The terminal end m of the conductor 104 is inserted into the hollow tubular member 111 and connected thereto through a soldering layer 112. Since titanium is hard to solder, the hollow tubular member 111 made of brass which is easier to solder is used.

A seal member 113, similar to the above-described seal material, is disposed between one end face of the hollow tubular member 111 and an end face of the insulating coating layer 105 of the feeder wire 93. The seal member 113 surrounds the conductor 104 protruding from the end face of the insulating coating layer 105. Thus, the conductor 104, protruding from the hollow tubular member 111 made of brass, and the insulating coating layer 105 are made water-tight with respect to the aqueous solution of NaCl 11.

With the above construction, the carbon electrode 13 and the feeder wire 93 are connected within the connecting bore 107 in the carbon electrode 13. Hence, only the feeder wire 93 is exposed to the outside, thereby providing a compact connecting structure.

In addition, the connection portion between the carbon electrode 13 and the conductor 104 of the feeder wire 93 is reliably sealed. Hence, the connecting portion is water-tightly sealed from the aqueous solution of NaCl 11 which prevents corrosion of the connecting portion.

Since the connecting portion is water-tight as described above, the carbon electrode 13 can be immersed into the aqueous solution of NaCl 11. Thus, the effective volume of the aqueous solution of NaCl 11 is increased when compared with when the upper portion of the carbon electrode protrudes from the liquid level, and the connecting portion is disposed therein.

Moreover, since the connecting bolt 106 is threadedly engaged with the internal threaded portion n of the carbon electrode 13, close contact between the internal threaded portion n and the connecting bolt 106 can be improved. Thus, the carbon electrode 13 and the feeder wire 93 can be reliably electrically connected to each other.

The connecting bolt 106 and the end of the feeder wire 93 connected to the connecting bolt 106 are fixed within the connecting bore 107 by the seal material 109. Thus, the mechanical connection between the carbon electrode 13 and the feeder wire 93 is very strong.

H. Corrosion Test for Test Material (FIGS. 1 to 3, 13, 15 and 17 to 21)

For a corrosion test of the test material 2, a damaged portion 114 is formed by a cutter in the coating film 4 on one flat surface of the test material 2. The damaged portion 114 cuts through the coating film 4 and reaches the steel plate 3, as shown in FIGS. 2 and 3. In this case, the coating film 4 on the other surface of the test material 2 and the coating film 4 on the peripheral surfaces function as a mask for the steel plate 3. A bore 115 in the test material 2 is used for passing a hanging string 25, made of the synthetic resin, therethrough.

The corrosion test of the test material 2 includes a process of immersing the test material 2 into the aqueous solution of NaCl 11, allowing a DC current to flow between the steel plate 3 and both carbon electrodes 13 in the aqueous solution of NaCl 11 and alternately switching over the polarity of the steel plate 3 to positive or negative polarity.

When the polarity of the steel plate 3 is negative, the coating film peeling-off step is performed. During this step, starting at the damaged portion 114 of the coating film, OH ions produced by electrolysis of water reduces the adhesion force of the coating film to the steel plate 3, thereby promoting the peel-off of and blistering of the coating film. On the other hand, when the polarity of the steel plate 3 is positive, the steel plate corroding step, i.e. the anode oxidation process is performed. By alternately repeating the peeling-off and anode oxidation of the coating film, the peeling-off of the coating film 4 and the corrosion of the steel plate 3 starting with the damaged portion 114 can be promoted. Thus, an overall evaluation of corrosion resistance can be performed within a short period of time.

During the steel plate corroding step, the amount of steel plate 3 corroded is proportional to an amount of coulombs used for energization. However, even in the same amount of coulombs is used, if the coating film peeled-off area of the steel plate 3 is varied, the amount of corrosion is varied. Therefore, the amount of coulombs required to corrode the steel plate 3 is determined based on the coating film peeled-off area of the steel plate 3.

Thus, a procedure is used which measures the coating film peeled-off area of steel plate 3 after the coating film peeling-off step, and determines the amount of coulombs used in the steel plate corroding step in accordance with the coating film peeled-off area of the steel plate 3.

FIG. 17 illustrates a corrosion test process. The corrosion test process will be described specifically with reference to FIG. 17.

(a) First Coating Film Peeling-off Step

At this step, the polarity of both carbon electrodes 13 in the aqueous solution of NaCl 11 is set at a positive polarity, while the polarity of the steel plate 3 of the test material 2 is set at a negative polarity by the polarity switch-over relay 28, as shown in FIG. 17(i). An electric current is supplied under a constant voltage from the DC power source 9 between the carbon electrodes 13 and the steel plate 3 through the aqueous solution of NaCl 11.

After a lapse of 5 to 10 minutes from the start of supplying the current, namely, after the current value is stabilized to some extent. a value $I_0$ of an electric current flowing in the steel plate 3 is measured by an ammeter 29.

If the peeling-off of the coating film 4 does not occur within the above-described time, a peeled-off coating film 4a is produced by a subsequent supplying of electric current, as shown in FIG. 17(ii).

The measurement of the current value $I_0$ may be carried out before the start of the first coating film peeling-off step. In this case, the polarity of the steel plate 3 is set at a negative polarity. If the polarity of the steel plate 3 is set at a positive polarity, the steel plate 3 is corroded at the damaged portion 114 of the coating film 4 and as a result, the coating film 4 is barely peeled off at a next coating film peeling-off step.

(b) Peeled-off Coating Film Removing Step

The test material 2 is withdrawn out of the aqueous solution of NaCl 11, and the peeled-off coating film 4a is removed from the test material 2 using adhesive tape, thereby exposing the coating film-peeled of f surface 3a in the steel plate 3, as shown in FIG. 17(iii). This removal can be alternatively carried out by ultra-sonic washing or a high-pressure water jet in the aqueous solution of NaCl 11.

(c) Second Coating Film Peeling-off Step

In this step, the polarity of both carbon electrodes 13 in the aqueous solution of NaCl 11 is set at a positive polarity, while the polarity of the steel plate 3 of the test material 2 is set at a negative polarity by the polarity switch-over relay 28, as shown in FIG. 17(iv). An electric current is supplied under a constant voltage from the DC power source 9 between the carbon electrodes 13 and the steel plate 3 through the aqueous solution of NaCl 11.

After a lapse of 5 to 10 minutes from the start of supplying the current, namely, after the current value is stabilized to some extent, a value $I_1$ of an electric current flowing in the steel plate 3 is measured by the ammeter 29.

If the peeling-off of the coating film 4 does not occur within the above-described time, a peeled-off coating film 4a is produced by a subsequent supplying of electric current, as shown in FIG. 17(iv).

(d) Step of Setting Amount of Coulombs in Corrosion of Steel Plate

The current values $I_0$ and $I_1$ measured at the first coating film peeling-off step (a) and the second coating film peeling-off step (c) are introduced to a calculating unit 116. In this calculating unit 116, a difference $\Delta I$ between both current values $I_0$ and $I_1$ is first calculated. This difference $\Delta I$ is substantially proportional to the coating film peeled-off area of the steel plate 3. Hence, the measurement of the coating film peeled-off area is replaced by the calculation of the difference $\Delta I$. Then, an amount of coulombs, corresponding to the difference $\Delta I$, is determined in terms of an energization time T under the constant voltage. This amount of coulombs can be determined by measuring a variation in voltage under a constant current, or by simultaneously measuring a current and a voltage.

(e) First Steel Plate Corroding Step

At this step, as shown in FIG. 17(v), the peeled-off coating film 4a produced at the second coating film peeling-off step (c) is not removed, and the polarity of the carbon electrodes 13 in the aqueous solution of NaCl 11 is set at a negative polarity, while the polarity of the steel plate 3 of the test material 2 is set at a positive polarity by the polarity switch-over relay 28. An electric current is supplied under a constant voltage from the DC power source 9 between the carbon electrodes 13 and the steel plate 3 through the aqueous solution of NaCl 11. The amount of time for supplying the current is the energization time T determined at the step (d) for setting the amount of coulombs.

Thus, a recess 117 is formed in the coating film peeled-off surface 3a of the steel plate 3 by the corrosion (anode oxidization), and a corrosion product 118 is accumulated within the recess 117.

The first steel plate corroding step must be carried out without removal of the peeled-off coating film 4a produced at the second coating film peeling-off step (c) in FIG. 17(iv). If the peeled-off coating film 4a is removed, the amount of coulombs determined at the stop (d) and the coating film peeled-off area of the steel plate 3 are unequal to each other. In addition, if the peeled-off coating film 4a is not removed, the coating film peeled-off area of the steel plate 3 in this corroding step is hardly different from the coating film peeled-off area of the steel plate 3 produced at the peeling-off coating film removing step (b) in FIG. 17(iii).

(f) Step of Removing Peeled-off Coating Film and Corrosion Product

The test material 2 is withdrawn out of the aqueous solution of NaCl 11, and the peeled-off coating film 4a and the corrosion product 118 are removed from the test material 2 using adhesive tape, thereby exposing the coating film peeled-off surface 3a and the recess 117 in the steel plate 3, as shown in FIG. 17(vi). This removal can be carried out alternatively by ultrasonic washing or a high-pressure water Jet in the aqueous solution of NaCl 11.

Thereafter, if required, a plurality of cycles, each including steps from the second coating film peeling-off step to the peeled-off coating film/corrosion product removing step, may be repetitively carried out. In this case, the difference $\Delta I$ is calculated, for example, from a current value $I_1$ measured at the second coating film peeling-off step in a first cycle and a current value $I_2$ measured at the third coating film peeling-off step in a second cycle.

If the coating film peeling-off step is carried out subsequent to the steel plate corroding step, the peeling-off of the coating film 4 is obstructed by the corrosion product 118. Hence, it is necessary to interpose the peeled-off coating film/corrosion product removing step between both the coating film peeling-off step and the steel plate corroding step.

Particular examples will be described below.

I. Coating film Peeling-off Test

A coating film peeling-off test, which will be described below, was carried out to examine the relationship between the applied voltage and the degree of peeling-off of the coating film 4.

(1) Conditions for Test Material 2

Steel plate:
   width: 70 mm; length: 150 mm; thickness 1.017 mm
   Coating film:
A pre-treating agent available under a trade name of SD2800 from Nippon Paint is used; a coating method: an cationic electrostatic coating; film thickness: 20 to 25 $\mu$m; a damaged portion is formed into a length of 50 mm using a cutter.

In addition, another test material 2 was made under the same conditions, except that the pre-treatment agent was not used.

Figure 18:
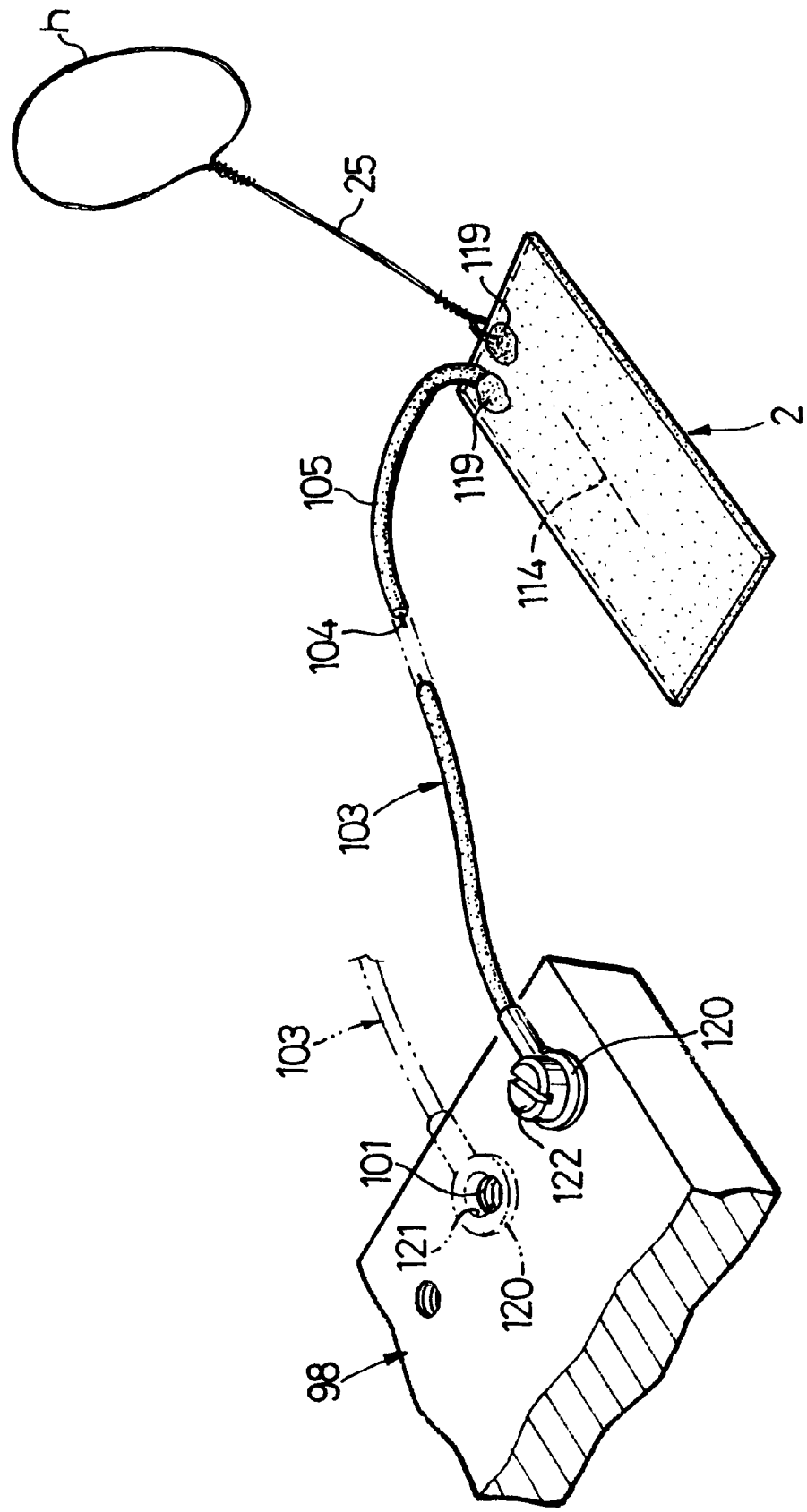
FIG. 18 is a perspective view showing the connection of the test material with an energizing terminal base.

As shown in FIG. 18, one end of the string 25, made of the synthetic resin, was tied in the bore 115 in the test material 2, and a loop h was formed at the other end of the string 25. The conductor 104, protruding from the corrosion resistant insulating coating layer 105 of the feeder wire 103, was soldered to the steel plate 3 on the opposite surface of the test material 2 from the surface having the damaged portion 114 provided thereon. Exposed portions of the steel plate 3 in the bore 115 and the soldered zone of the test material 2 and the conductor 104 are covered by a seal member 119. A bolt insertion bore 121 in a terminal 120, connected to the other end of the feeder wire 103, was aligned with the connecting bore 101 in the energizing terminal base 98. A bolt 122 was threadedly inserted into the connecting bore 101 through the bolt insertion bore 121. This caused the steel plate 3 and the DC power source 9 to be electrically connected to each other through the polarity switch-over relay 28. The test material 2 was immersed into the aqueous solution of NaCl 11 by hanging it from the support bar 24 through the loop h of the string 25 made of the synthetic resin.

(2) The concentration of the aqueous solution of NaCl 11 was set at 3%, and the temperature of the aqueous solution of NaCl 11 was set at 40° C. The polarity of the steel plate 3 was set at a negative polarity, while the polarity of the carbon electrode 13 was set at a positive polarity. The test time was set at 2 hours. The applied voltage was varied in a range of 0 to 20 V. Under such conditions, the coating film peeling-off test for the test material 2 was carried out.

(3) Test Result

Figure 19:
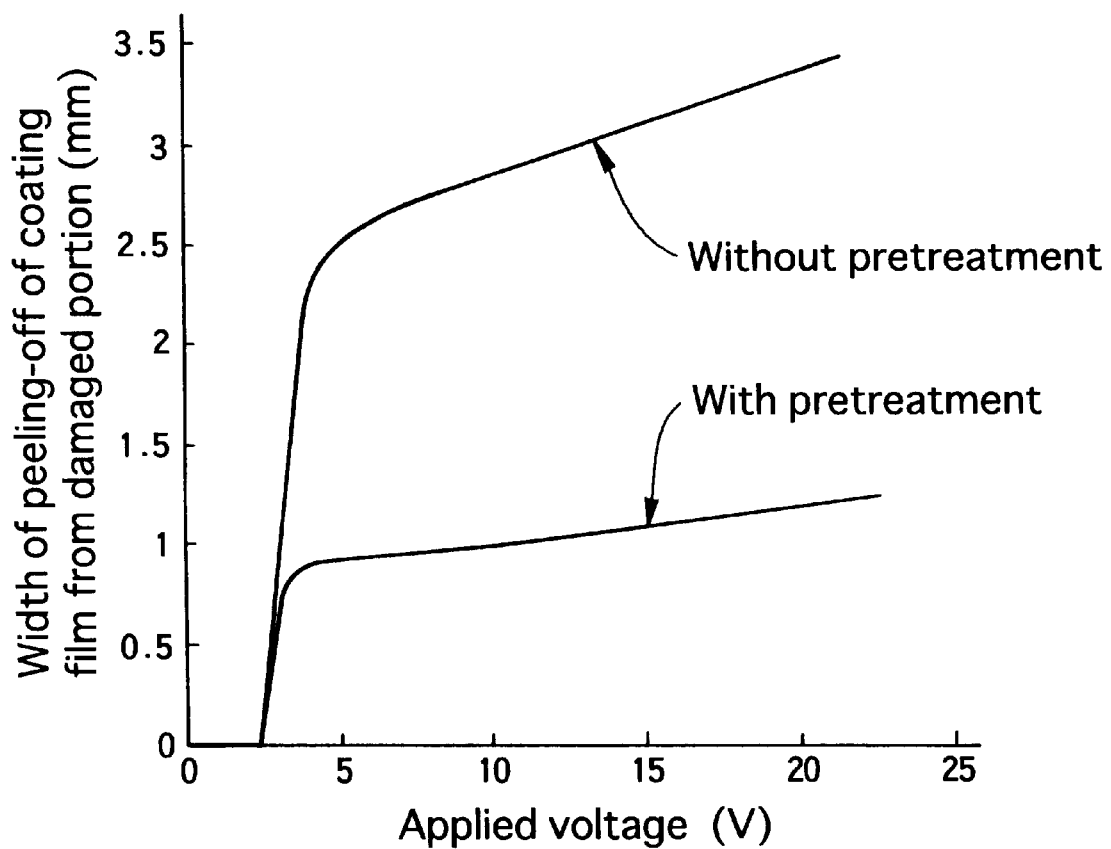
FIG. 19 is a graph illustrating the relationship between the applied voltage and the width of peeling-off of a coating film from a damaged portion of the test material.

FIG. 19 is a graph illustrating the relationship between the applied voltage and the width s of the coating film peeled off from the damaged portion 114 (see FIG. 17 (iii)). As apparent from FIG. 19, the peeling-off of the coating film 4 is started at the applied voltage of about 2.5 V, whether the pre-treatment is carried out or not. To perform the peeling-off of the coating film with stability, it is preferred that the applied voltage is set at about 5.5 V or more for the test material 2 subjected to the pretreatment and at about 8 V or more for the test material 2 not subjected to the pretreatment.

At the same applied voltage the amount of coating film peeled off is smaller in the test material 2 subjected to the pretreatment than in the test material 2 not subjected to the pretreatment. As shown from this, pretreatment is preferably carried out in order to enhance the durability of the coating film 4.

II. Corrosion Resistance Test (1) Conditions for the test material 2 in the corrosion resistance test are identical to those described in the item I for the coating film peeling-off test.

(2) Steps and conditions for the steps in a particular example are as shown in Table 1. In this case, the concentration of the aqueous solution of NaCl was set at 3%, and the temperature of the aqueous solution of NaCl was set at 45° C.

TABLE I

| Cycle | Step | Voltage | Current Value | Difference ΔI | Energizing time |
|---|---|---|---|---|---|
| | first peeling-off | 16 V | $I_0$ = 1.9 A | — | 4 hours |

TABLE I-continued

| Cycle | Step | Voltage | Current Value | Difference ΔI | Energizing time |
|---|---|---|---|---|---|
| 1 | second peeling-off | 16 V | $I_1$ = 14.9 A | $I_1 - I_0$ | 4 hours |
| | first steel plate corrosion | 10 V | — | — | T = 1810 seconds |
| 2 | third peeling-off | 16 V | $I_2$ = 18.3 A | $I_2 - I_1$ | 4 hours |
| | second steel plate corrosion | 10 V | — | — | T = 1984 seconds |
| 3 | fourth coating film peeling-off | 16 V | $I_3$ = 19.6 A | $I_3 - I_2$ | 4 hours |
| | third steel plate corrosion | 10 V | — | — | T = 1986 seconds |
| 4 | fifth coating film peeling-off | 16 V | $I_4$ = 19.4 A | $I_4 - I_3$ | 4 hours |
| | fourth steel plate corrosion | 10 V | — | — | T = 1472 seconds |

(3) A cycle corrosion test (CCT) enabling the deterioration of the coating film 4 and the corrosion of the steel plate 3 to be simultaneously estimated was carried out as a comparative example, using a test material 2 subjected to a pretreatment similar to the above-described pretreatment and a test material 2 not subjected to the pretreatment. Conditions for this test are as follows: a step for carrying out a spraying of salt water for 2 hours, a wetting for 2 hours and a drying for 4 hours was repeated three times. This was defined as one cycle. Therefore, the time required for one cycle is 24 hours.

(4) Result of Test

Figure 20:
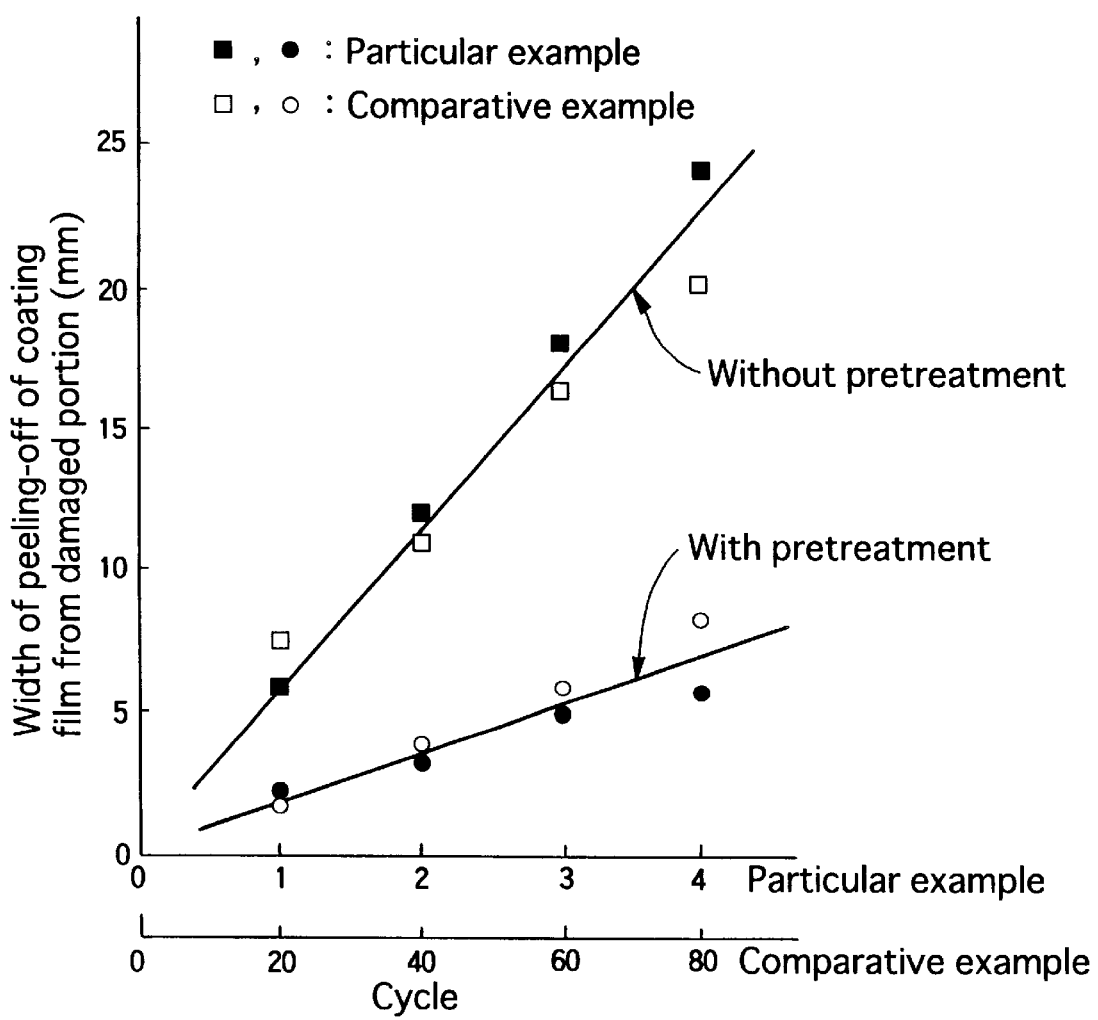
FIG. 20 is a graph illustrating the relationship between the cycle and the width of peeling-off of the coating film from the damaged portion of the test material.

FIG. 20 is a graph illustrating the relationship between the cycle and the width s (see FIG. 17 (iii)) of the coating film peeled off from the damaged portion 114 when 20, 40, 60 and 80 cycles in the comparative example correspond to 1, 2, 3 and 4 cycles in the particular example. As apparent from FIG. 20, the 1 cycle in the particular example substantially compares with 20 cycles in the comparative example in the above-described width s of coating film peeled off.

Table 2 shows the relationship between the cycle and the maximum decrement in plate thickness in the particular example using the test material 2 subjected to the pretreatment.

TABLE 2

| Cycle | Maximum decrement in plate thickness (mm) |
|---|---|
| 1 | 0.146 |
| 2 | 0.347 |
| 3 | 0.643 |
| 4 | 0.968 |

Figure 21:
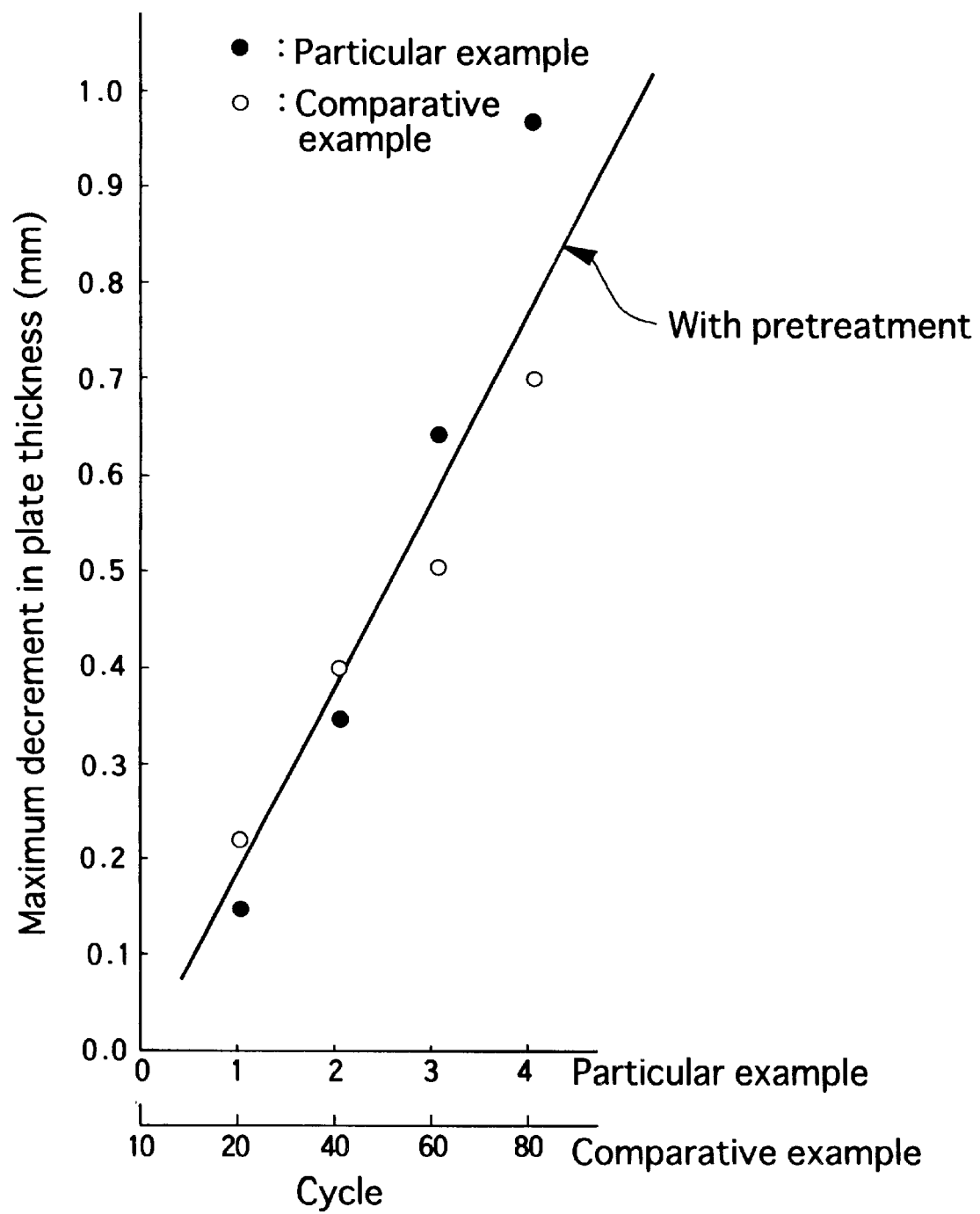
FIG. 21 is a graph illustrating the relationship between the cycle and the maximum decrement in plate thickness of the test material.

FIG. 21 is a graph illustrating the relationship between the cycle similar to the above-described cycle and the maximum decrement in plate thickness. Even in the comparative example, the test material 2 subjected to the pretreatment was used. As apparent from FIG. 21, the 1 cycle in the particular example substantially compares with 20 cycles in the comparative example even in the above-described maximum decrement in plate thickness.

It is apparent from this result that in the particular example, the peeling-off of the coating film 4 and the corrosion of the steel plate 3, i.e., the metal blank, can be promoted, and the overall evaluation of the corrosion resistance can be performed in a short time.

When only the coating film peeling-off test for the film 4 is carried out, the polarity switch-over relay 28 is switched over, so that the polarity of the steel plate 3 is negatively polarized as described above. In this case, the coating film 4 is provided only on one surface of the steel plate 3 because the steel plate corroding step is not included. Hence, it is unnecessary to mask the other surface of the steel plate 3.

I. Determining Device for Determining Timing of Replacement of Carbon Electrode (FIGS. 4 to 6 and 22 to 24)

Carbon particles are dropped by the carbon electrode 13 as a result of use of the carbon electrode 13 for a long time and the conductive area varies. In order to replace the carbon electrode 13 by a new carbon electrode 13, if it reaches the end of its service life, a determining device 123 is mounted in the electrolytic test machine 1. The device 123 is incorporated in the computer programmed control unit 10.

Figure 22:
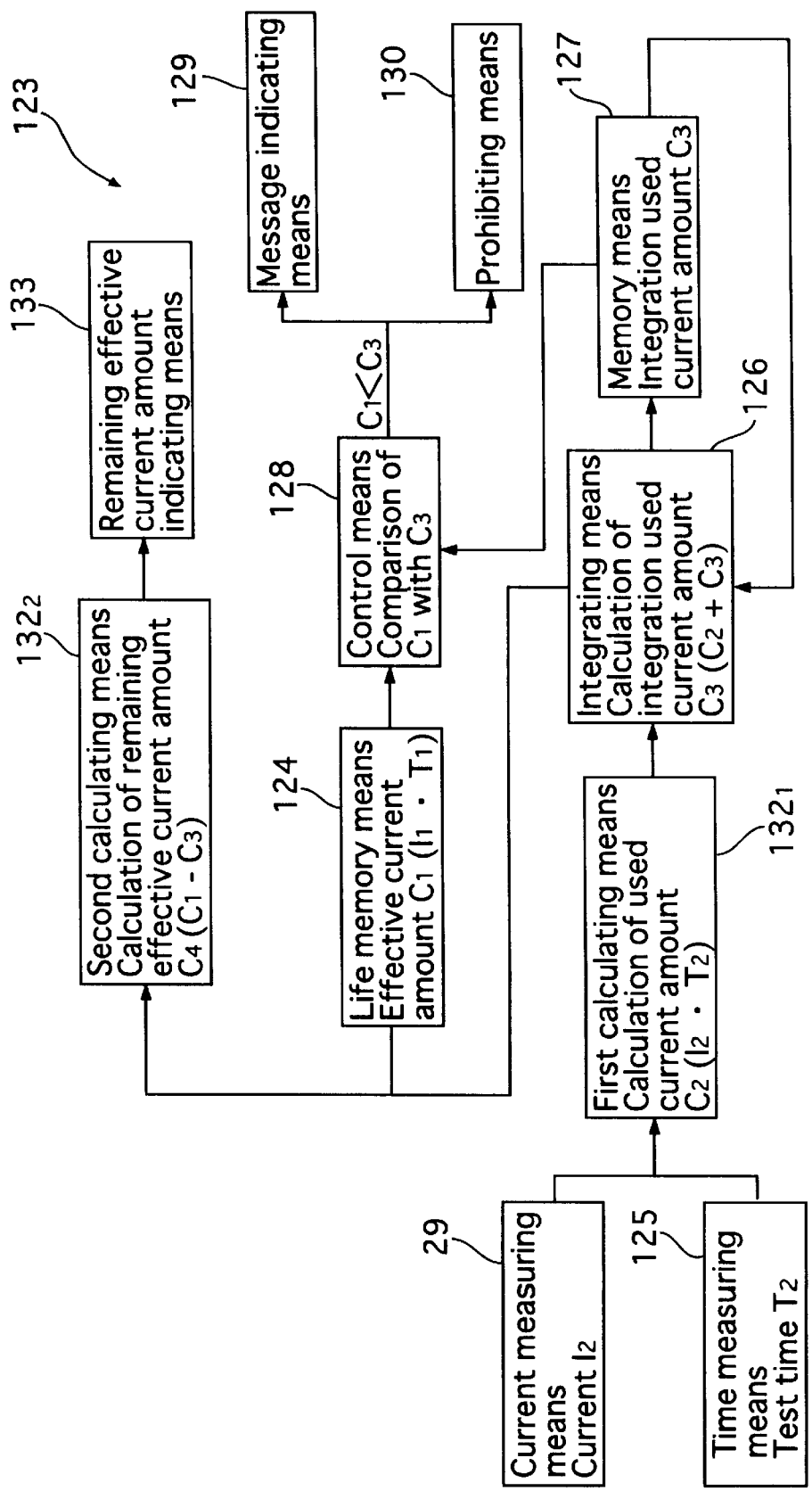
FIG. 22 a block diagram of a determining device for determining a replacement time of the carbon electrode.
Figure 23:
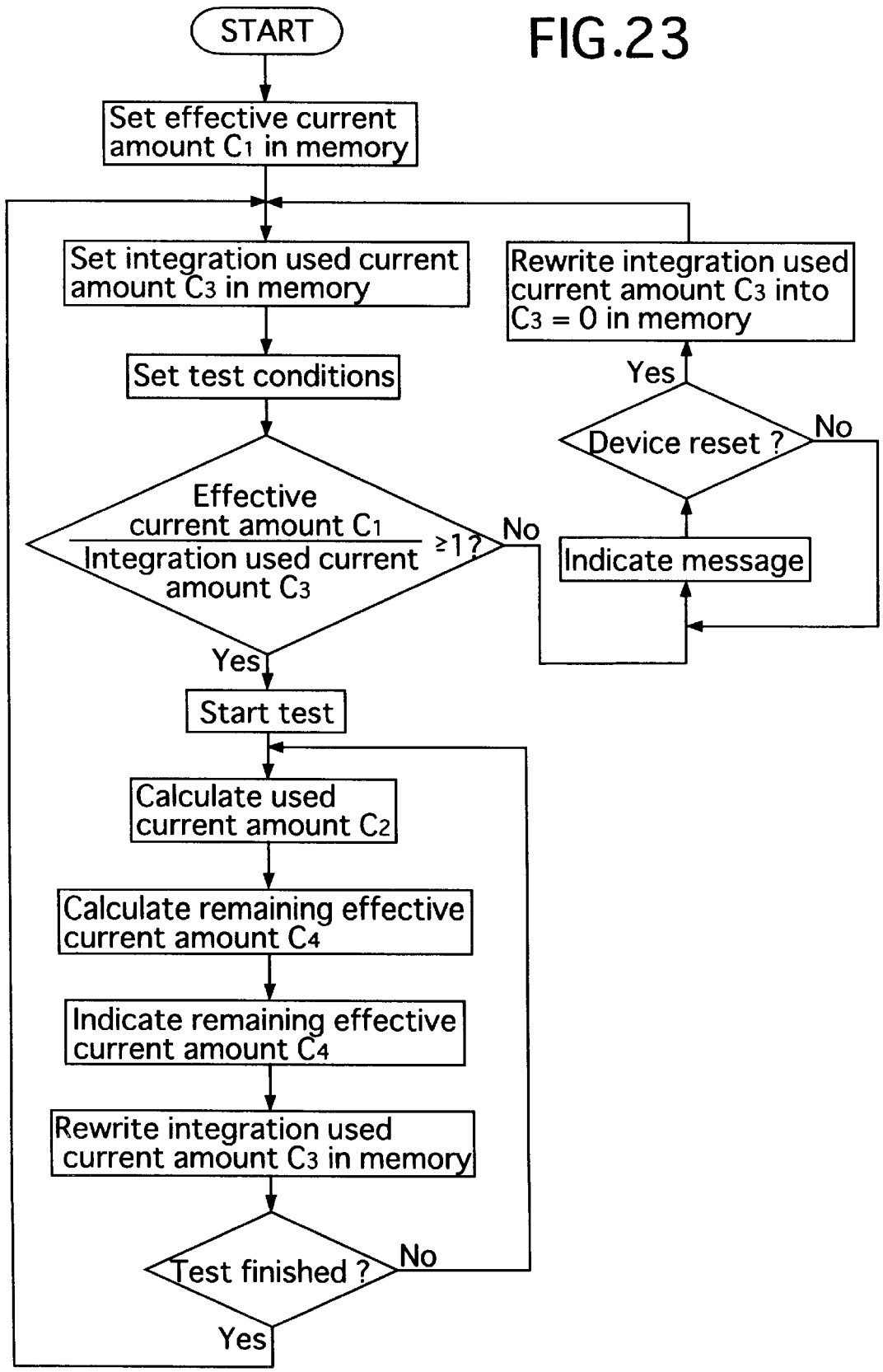
FIG. 23 is a flow chart illustrating the operation of the determining device for determining the replacement time of the carbon electrode;.

FIG. 22 is a block diagram of the determining device 123, and FIG. 23 is a flow chart illustrating the operation of the device 123. The term "set test conditions" in FIG. 23 means that any one of the following conditions are selected: a) the corrosion test including the coating film peeling step and the steel plate corroding step is to be carried out, b) the coating film peeling-off test is to be carried out and c) the test is to be finished. Conditions selected are then input.

Referring to FIG. 22, the determining device 123 includes a life memory means 124 for storing the service life of the carbon electrode 13 in the form of an effective current amount $C_1$ which is a product $I_1 \cdot T_1$ of a certain current $I_1$ flowing in the carbon electrode 13 and a total test time $T_1$ capable of being used when the current $I_1$ continues to flow. A current measuring means (ammeter) 29 measures a current 12 flowing in the carbon electrode 13, during a test. A time measuring means 125 measures a test time $T_2$. A first calculating means $132_1$ calculates a used current amount $C_2$ which is a product $I_2 \cdot T_2$ of the current $I_2$ and the test time $T_2$. An integrating means 126 integrates the used current amounts $C_2$ to calculate an integration used current amount $C_3$ from the start of the use of the carbon electrode 13. A memory means 127 stores the integration used current amount $C_3$. A control means 128 compares the effective current amount $C_1$ with the integration used current amount $C_3$ at the start of the test and to transmit an electrode replacing signal, when $C_1 < C_3$.

With such an arrangement, as the carbon electrode 13, which is a consumable electrode, reaches the end of its service life, the replacement time of the carbon electrode 13 can be automatically detected.

In this case, even if the relationship between the effective current amount $C_1$ and the integration used current amount $C_3$ becomes $C_1 < C_3$, the test is continued. This is permitted by depending on a margin of the effective current amount $C_1$ corresponding to several runs of the test.

The determining device 123 includes a) a message indicating means 129 for informing a testing operator of reaching the electrode replacing timing, based on the electrode replacing signal from the control means 128, and b) a prohibiting means 130 for prohibiting the supplying of current to the carbon electrode 13.

As best shown in FIGS. 4 to 6 and 24, a message on the message indicating means 129 is displayed by characters on a liquid crystal display plate 131 mounted on the upper surface of the left cover 52 which covers the control section C. The prohibiting means 130 is operated to maintain the DC power source 9 in its OFF state. Thus, the testing operator can reliably know the replacement time of the carbon electrode 13.

As shown in FIG. 23, the determining device 123 is constructed, so that the device 123 will not operate after replacing the electrode 13 unless the integration used current amount $C_3$ stored in the memory means 127 is reset to 0.

If the effective current amount $C_1$ and the integration used current amount $C_3$ are in a relation of $C_1 \geq C_3$ prior to starting the test, the test is started, and the calculation and the integration of the used current amount $C_2$ and the like are carried out.

The determining device 123 includes a second calculating means $132_2$ for subtracting the integration used current amount $C_3$ from the effective current amount $C_1$ in the carbon electrode 13 to determine a remaining effective current amount $C_4$, and a remaining effective current indicating means 133 for indicating the remaining effective current amount $C_4$.

Figure 24:
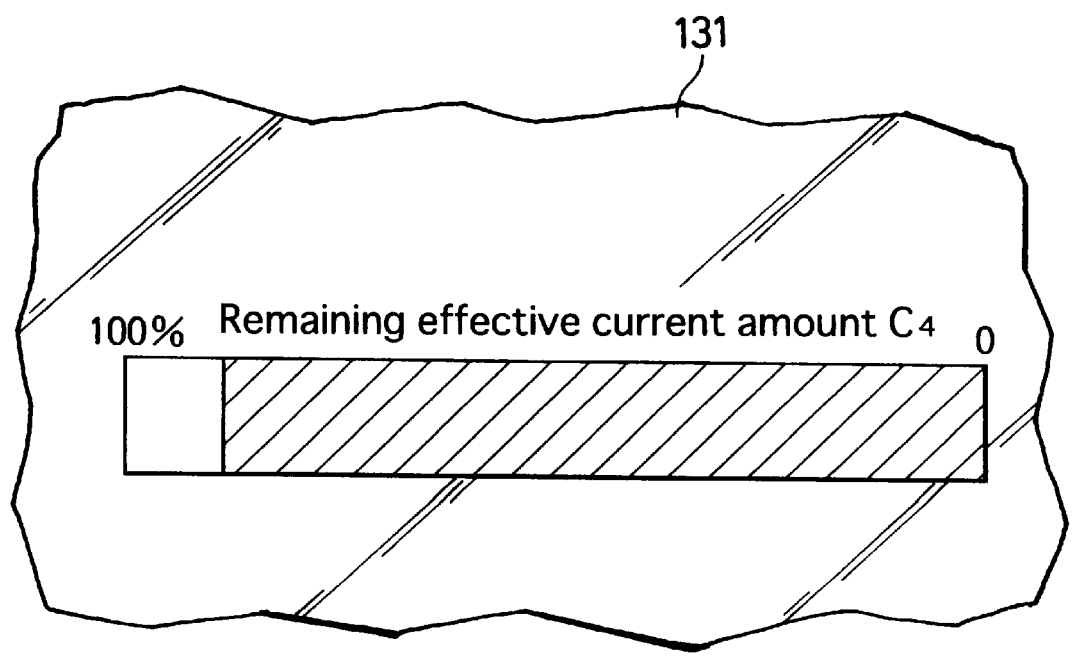
FIG. 24 is a diagram for explaining a remaining effective current quantity indicating portion.

The second calculating means 1322 calculates the remaining effective current amount $C_4$ according to $C_4 (\%) = \{1-(C_3/C_1)\} \times 100$. The remaining effective current amount $C_4$ indicated by the remaining effective current amount indicating means 133 is indicated by a bar graph on the liquid crystal display plate 131, so that the remaining effective current amount $C_4$ is gradually decreased, as shown in FIG. 24. Thus, it is possible for the testing operator to easily know the remaining service life of the carbon electrode 13 and the variations therein.

When the effective current amount $C_1$ and the integration used current amount $C_3$ are in a relation of $C_1 \leq C_3$, the effective current amount $C_4$ is displayed as being $C_4 = 0\%$.

J. Structure of Sealing of the Opening in the Electrolytic Cell (FIGS. 6 to 10, 13 and 25 to 27)

As shown in FIG. 10, the heights of the front and rear wall portions 57 and 71 in the peripheral wall 47 of the electrolytic cell 12 are lower than heights of the left and right sidewall portions 48 and 49. Part of each of the left and right sidewall portions 48 and 49, which protrudes from the front and rear wall portions 57 and 71, has a vertical front edge 134, a forward declined upper edge 135, a horizontal upper edge 136, a rearward declined upper edge 137 and a vertical rear edge 138. A seal member 139, made of a rubber, is mounted on the upper edges of the front and rear wall portions 57 and 71 and all the edges 134 to 138 of the left and right sidewall portions 48 and 49, i.e., an entire peripheral edge of the upward opening 19.

Figure 25:
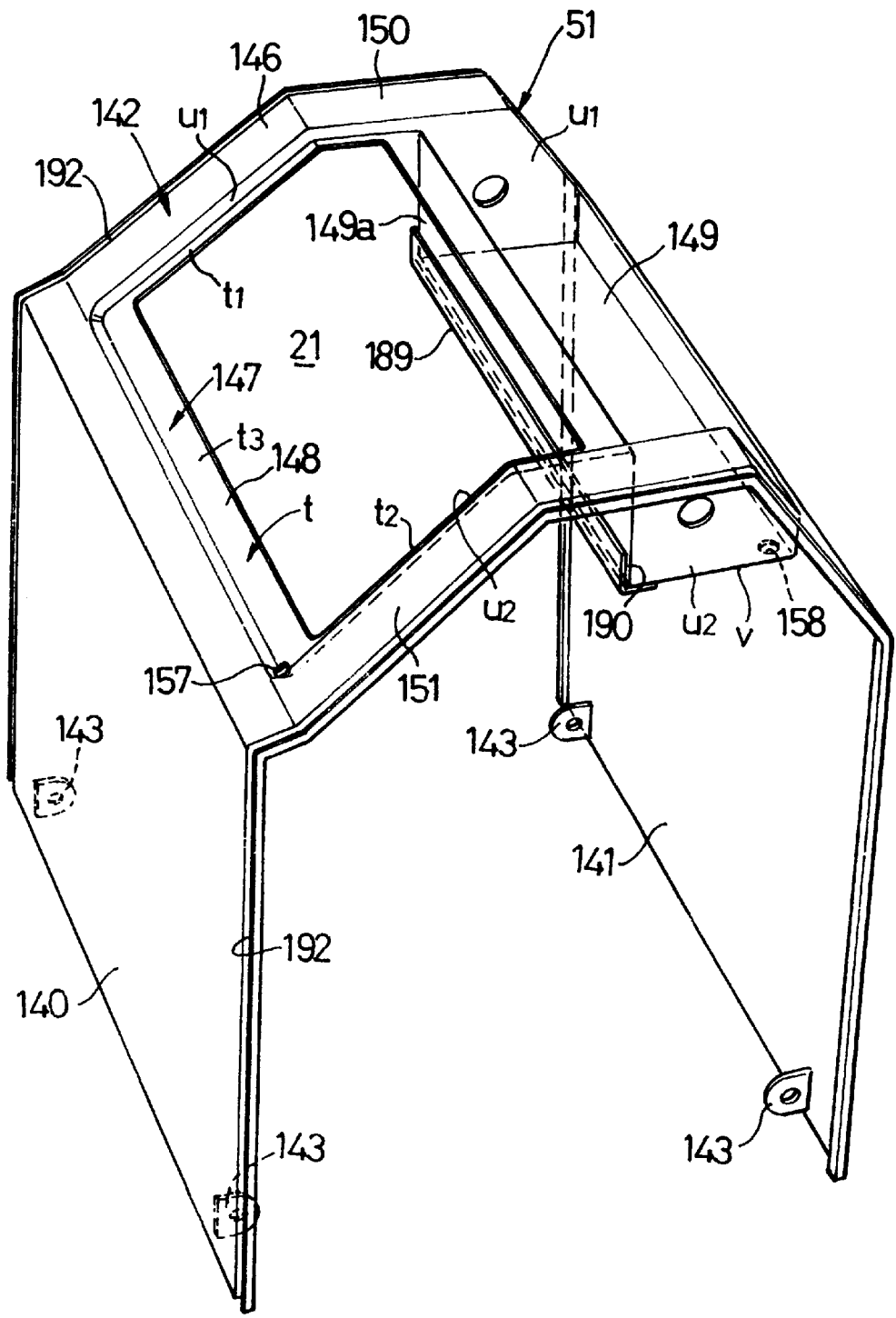
FIG. 25 is a perspective view of a central cover.

As best shown in FIG. 25, the central cover section 51 is comprised of a front wall 140, a rear wall 141 and an upper wall 142 which connects the front and rear walls 140 and 141 to each other. The central cover section 51 is placed over the electrolytic cell 12 from above the electrolytic cell 12. Thus, the front, upper and rear portions of the electrolytic cell 12 are covered with the central cover section 51. As shown in FIGS. 8, 9 and 25, inward-turned projecting pieces 143 are provided on right and left ends of lower portions of inner surfaces of the front and rear walls 140 and 141. The projecting pieces 143 at the right end are detachably mounted to front and rear angle members 144 extending vertically to form the frame 90 of the machine base 44. The projecting pieces 143 at the left end are detachably mounted to front and rear angle members 145 extending vertically of the machine base 44.

As best shown in FIGS. 6, 10 and 25, the upper wall 142 has an outer peripheral frame-like section 146, and a recess 147 surrounded by the outer peripheral frame-like section 146. The recess 147 is comprised of a relatively large and shallow recess portion 148 located on a front side, and a relatively small and deep recess portion 149 located on a rear side. The quadrilateral opening 21 for placing the test material 2 into and for removing the test material 2 out of the electrolytic cell 12 is provided in a bottom wall t of the shallow recess portion 148.

Each of left and right portions 150 and 151 of the outer peripheral frame-like section 146 has a shape extending along the forward-declined edge 134, the horizontal upper edge 136 and the rearward-declined upper edge 137 in the left and right sidewall portions 48 and 49 of the electrolytic cell 12, as shown in FIG. 10. In addition, each of left and right portions $t_1$ and $t_2$ of the bottom wall of the shallow recess portion 148 has a shape extending along portions of the forward-declined upper edge 135 and the horizontal upper edge 136.

As best shown in FIGS. 7, 10, 25 and 26, left and right sidewalls $u_1$ and $u_2$ of the recess 147 are fitted between the left and right sidewall portions 48 and 49 of the electrolytic cell 12. Thus, lower surfaces of the left and right portions 150 and 151 of the outer peripheral frame-like section 146 are brought into close contact with the upper surface of the seal member 139 at portions of the forward-declined upper edge 135, the horizontal upper edge 136 and the rearward-declined upper edge 137 of the left and right sidewalls 48 and 49. In addition, outer surface of the left and right sidewalls $u_1$ and $u_2$ of the recess 147 are brought into close contact with the inner surface of the seal member 139 at the vertical front edge 134, the forward-declined upper edge 135, the horizontal upper edge 136, the rearward-declined upper edge 137 and the vertical rear edge 138 of the left and right sidewall portions 48 and 49.

As best shown in FIGS. 7, 10, 13 and 27, a lower surface of a front portion $t_3$ of the bottom wall of the shallow recess portion 148 is brought into close contact with the upper surface of the seal member 139 at the front wall portion 57 of the electrolytic cell 12. A lower surface of a bottom wall v of the deep recess portion 149 is brought into close contact with the upper surface of the seal member 139 at the rear wall portion 71 of the electrolytic cell 12.

In this way, when the central cover section 51 is placed over the electrolytic cell 12 from above the electrolytic cell 12 and mounted to the machine base 44, the opening. 19 in the electrolytic cell 12 can be reliably sealed.

K. Structure for Opening and Closing Lid and Structure for Collecting Water Drops Deposited on Inner Surface of Lid (FIGS. 4 to 7, 9, 13, 14 and 25 to 28)

Figure 26:
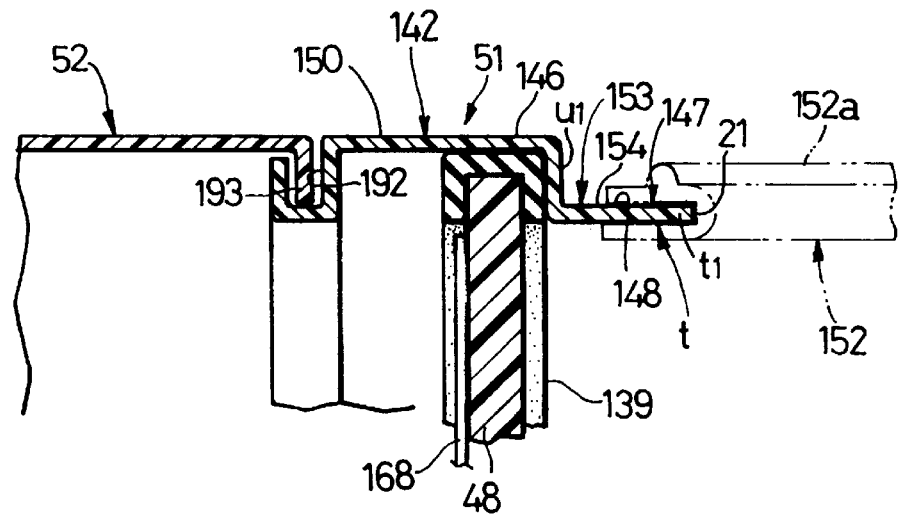
FIG. 26 is a sectional view taken along a line 26—26 in FIG. 6.
Figure 27:
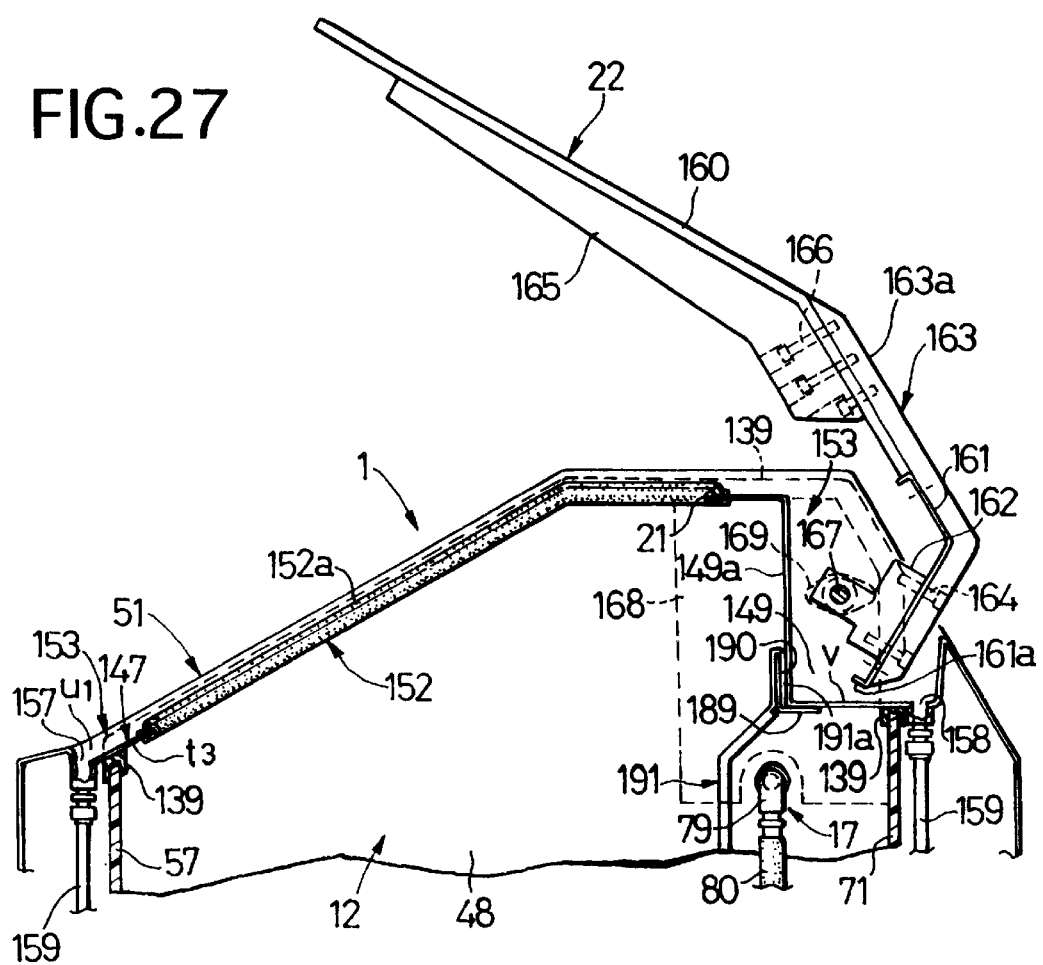
FIG. 27 is a sectional view taken along a line 27—27 in FIG. 6.

As shown in FIGS. 4, 6, 26 and 27, an annular seal member 152 is mounted to that entire peripheral edge of the upper wall of the central cover section 51 which defines the upward opening 21. The annular seal member 152 includes an annular lip 152a which protrudes from an upper surface of the annular seal member 152 and surrounds the opening 21. Thus, an annular tub 153 is formed by cooperation of the annular seal member 152, the shallow recess portion 148 and the deep recess portion 149 with one another. The tub 153 is located outside the annular seal member 152 to surround the annular seal member 152. Left and right grooves 154 and 155 in the annular tub 153 are forward declined. A front groove 156 in the annular tub 153 assumes a V-shape. As best shown in FIGS. 6, 14 and 27, drainage ports 157 and 158 are opened in right ends of bottoms of the front groove 156 and the rear deep recess portion 149. The drainage ports 157 and 158 are connected to a downstream portion of the drainage pipe line 18 from the manual cock 32 through a tube 159.

As best shown in FIGS. 4, 5, 13 and 27, the lid 22 for opening and closing the opening 21 includes a transparent synthetic resin plate 160 located in a front side which forms a main body of the lid 22. A steel plate 161 made of a stainless steel is mated to a rear edge of the plate 160. As best shown in FIGS. 6 and 13, when the opening 21 has been closed, the transparent synthetic resin plate 160 covers the substantially entire shallow recess portion 148, with its inner surface put in close contact with the annular lip 152a of the annular seal member 152. The steel plate 161 covers the substantially entire deep recess portion 149, with its rear edge 161a located in the vicinity of an opening of the deep recess portion 149. Namely, the substantially entire annular tub 153 is covered with the lid 22.

A pair of brackets 162, made of a stainless steel, is disposed at a predetermined distance on an inner surface of the steel plate 161. A pair of reinforcing rib members 163 is disposed on an outer surface of the steel plate 161. The pair of brackets and the pair of reinforcing rib members 163 are coupled to each other by a plurality of bolts with the steel plate 161 interposed therebetween. Protrusions 163a of the reinforcing rib members 163 are disposed on an outer surface of a rear portion of the transparent synthetic resin plate 160 to project forwards from the steel plate 161. The protrusions 163a are coupled to rear portions of a pair of reinforcing rib members 165 by a plurality of bolts 166 with the transparent synthetic resin plate 160 interposed therebetween. The pair of reinforcing rib members 165 are made of a synthetic resin and are disposed on an inner surface of the main plate 160. A front portion of each of the reinforcing rib members 165 is bonded to the transparent synthetic resin plate 160.

As best shown in FIGS. 6, 7 and 9, a support shaft 167 for the lid 22 extends laterally in a substantially central area of the deep recess portion 149 in such a manner that its opposite ends are passed through the left and right sidewalls $u_1$ and $u_2$ of the recess 147 and the left and right sidewall portions 48 and 49 of the electrolytic cell 12. The support shaft 167 is turnably supported on bearings 169 mounted on outer surfaces of reinforcing plates 168 made of a steel and mounted on the outer surfaces of the left and right sidewalls 48 and 49. The support shaft 167 is passed through the brackets 162 of the lid 22 and short tubes 170 fixed to the brackets 162, and is coupled in a rotation-prevented manner to the short tube 170.

Figure 28:
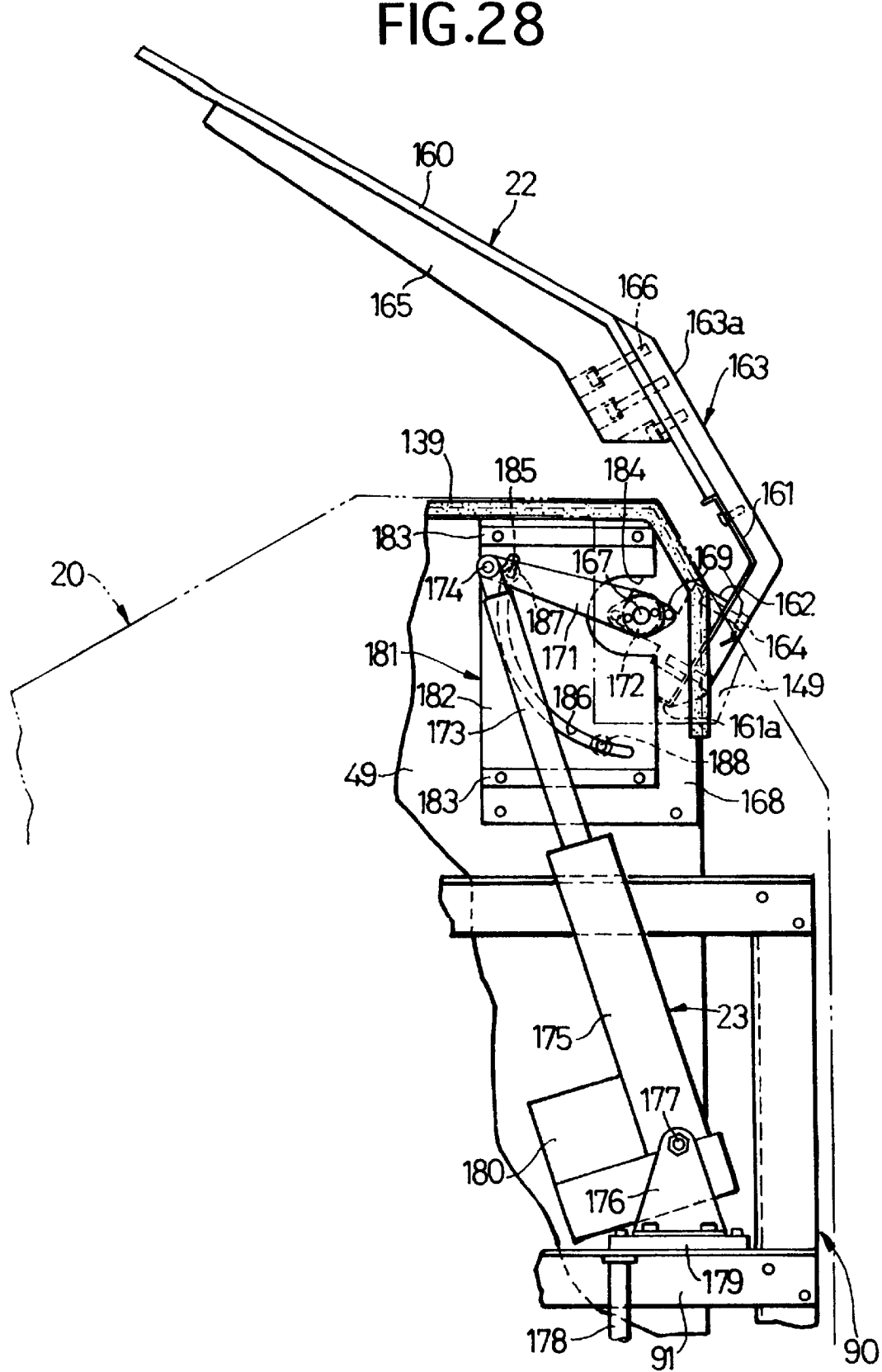
FIG. 28 is a sectional view taken along a line 28—28 in FIG. 7.

As best shown in FIGS. 7, 9 and 28, a right end of the support shaft 167 protruding from the right sidewall portion 49 of the electrolytic cell 12 is passed through an upper end of a link 171 and a short tube 172 fixed to the link 171. The right end of the support shaft 167 is coupled to the short tube 172 in a rotation-prevented manner. The link 171 is pivotally connected at its lower end, through a connecting pin 174, to a piston rod 173 of the electric power cylinder 23 which is disposed below the link 171.

A cylinder body 175 of the power cylinder 23 is pivotally connected at its lower end to a bifurcated support member 176 of the machine base 44 through a connecting shaft 177. The support member 176 is fixed to a mounting base 179 which is supported by the lower angle member 91 of the frame 90 and a support pillar 178. The power cylinder 23 includes an electric motor 180 integral with the cylinder body 175.

On the outer surface of the right sidewall portion 49 of the electrolytic cell 12, a guide plate 181 for the link is disposed in an superposed relation to the reinforcing plate 168. The guide plate 181 has L-shaped legs 183 at upper and lower edges of a flat plate portion 182 thereof. The legs 183 are mounted to the right sidewall portion 49 through the reinforcing plate 168. The flat plate portion 182 has a notch 184 for avoiding interference with the support shaft 167, and an arcuate guide bore 186 in which a guide pin 185 projectingly is slidably fitted and which extends vertically. Limit switches 187 and 188 are mounted to an inner surface of the flat plate portion 182 in the vicinity of upper and lower ends of the guide bore 186 and are operated by the guide pin 185. The lower limit switch 188 determines a closed position of the lid 22, as shown in FIG. 9, and the upper limit switch 187 determines an opened position of the lid 22, as shown in FIG. 28. When the opening 21 is opened, one end of the lid 22 on the side of its rotational center, e.g., the rear edge 161a of the steel plate 161 in the illustrated embodiment, is disposed within the deep recess portion 149 of the annular tub 153, as best shown in FIG. 27.

In the corrosion test, the temperature of the aqueous solution of NaCl 11 rises to about 40° C. as described above. Hence, many waterdrops are likely to be deposited onto the inner surface of the transparent synthetic resin plate 160 of the lid 22 which closes the opening 21.

With the above construction, many waterdrops deposited on the inner surface of the transparent synthetic resin plate 160 are displaced upon opening of the lid 22, and dropped from the rear edge 161a via the steel plate 161 into and collected in the deep recess portion 149 of the annular tub 153. Waterdrops deposited on the annular seal member 152 and dropped outside the seal member 152 are likewise collected into the annular tub 153. The water collected in the above manner is discharged through the tube 159 into the drainage pipe line 18.

As shown in FIGS. 4, 10, 13, 25 and 27, an L-shaped plate 189 is mounted to a lower portion of the front wall 149a defining the deep recess portion 149 in the central cover section 51. A fine groove 190 is defined by cooperation of the L-shaped plate 189 and the front wall 149a with each other. An upper folded edge 191a of a cover member 191, covering the heater chamber 68, is engaged in the fine groove 190. A lower portion 191b of the cover member 191 is fitted into a notch-like recess 67a in a rear surface of the upper portion of the partition plate 67 defining the heater chamber 68, as shown in FIGS. 11 and 13.

L. Structure of Coupling of Central Cover Section and Left and Right Cover Sections (FIGS. 6 to 8, 25 and 26)

The structure of coupling the central cover section 51 covering the front, upper and rear portions of the electrolytic cell 12 and the left cover section 52 covering the control section C, adjacent the central cover section 51, is constructed in the following manner: As best shown in FIGS. 25 and 26, a recessed groove 192 is defined in an edge of the central cover section 51, which is adjacent the left cover section 52, continuously over the entire periphery thereof, so that the groove 192 is opened and forms a J or U shape. A projection 193 is formed on an edge of the left cover section 52, which is adjacent the central cover section 51, continuously over the entire periphery thereof, so that it is folded inward or downward into an L shape.

When the central cover section 51 has been fixed to the machine base 44, the left cover section 52 is coupled to the central cover section 51 by bringing the lower end of the L-shape portion of the projection 193 of the left cover section 52 into engagement with the J or U shaped portion of the recessed groove 192 in the central cover section 51 to lower the left cover section 52, and then bringing the upper portion of the projection 193 into engagement with the upper portion of the recessed groove 192. The structure of coupling of the central cover section 51 and the right cover section 53 is the same as the above structure.

With such a construction, even if the left and right cover sections 52 and 53 have water poured upon them, the water is prevented from entering into the control section C and the mechanical section M.

The water, entering the coupled portions of the central cover section 51 and the left and right cover sections 52 and 53, is received into the recess 192 and discharged downwards.

During maintenance of the electrolytic cell 12, the mechanical section M and the control section C, the left and right cover sections 52 and 53 can be easily lifted and removed from the central cover section 51. Similarly, the left and right cover sections 52 and 53 are easily recoupled to each other. In addition, removing and attaching operations are not required, because no seal member is used at each of the coupled portions.

Thus, maintenance of the electrolytic cell 12, the mechanical section M and the control section C, is improved over the prior art.

M. Chlorine Gas Treating Device (1) Entire Structure and Function thereof (FIGS. 4, 7 to 11, 13, 14 and 29 to 34)

At the coating film peeling-off step in the corrosion test, a chlorine gas is generated on the side of the carbon electrodes 13 with the electrolysis of the aqueous solution of NaCl 11 due the polarity of the carbon electrodes 13 being set at a positive polarity.

The chlorine gas treating device 6 is mounted in the electrolytic test machine 1 to purify the chlorine gas. The treating device 6 collects the chlorine gas generated around the carbon electrodes 13 in response to the electrolysis of the aqueous solution of NaCl 11, together with a part of the aqueous solution of NaCl 11, adsorbs the chlorine gas, decomposes NaClO which is a product of reaction of the NaOH and the chlorine gas produced by the electrolysis of the aqueous solution of NaCl 11, thereby producing NaCl, returns the NaCl to the electrolytic cell 12 and decomposes HClO which is a similar reaction product.

The chlorine gas treating device 6 will be described more specifically below. As shown in FIGS. 4, 7, 8, 10, 11 and 13, a chlorine gas collecting hood 194 is placed on the partition plate 54 and the division plate 56 in the left electrode chamber 55. A mounting plate 195, integral with the hood 194, is screwed to the left sidewall portion 48 of the electrolytic cell 12. As best shown in FIGS. 7 and 11, the hood 194 covers the entire upper portion of the electrode 13 and closes the upward opening 55a in the electrode chamber 55. The hood 194 includes a box-like hood body 196 placed on the partition plate 54 and the division plate 56, and a roof-like portion 197, integral with the hood body 196, and assuming an angle shape in cross section. A lower surface of the roof-like portion 197, namely, a lower ridgeline 199 is inclined at an angle $\alpha \geq 1$ degree, so that its rear end, which is a first end, is located at a higher elevation than its front end which is the other or second end. A through-hole 200 is defined in the rear end of the roof-like portion 197 for venting air within the electrode chamber 55 at the start of supplying water into the electrolytic cell 12.

Figure 29:
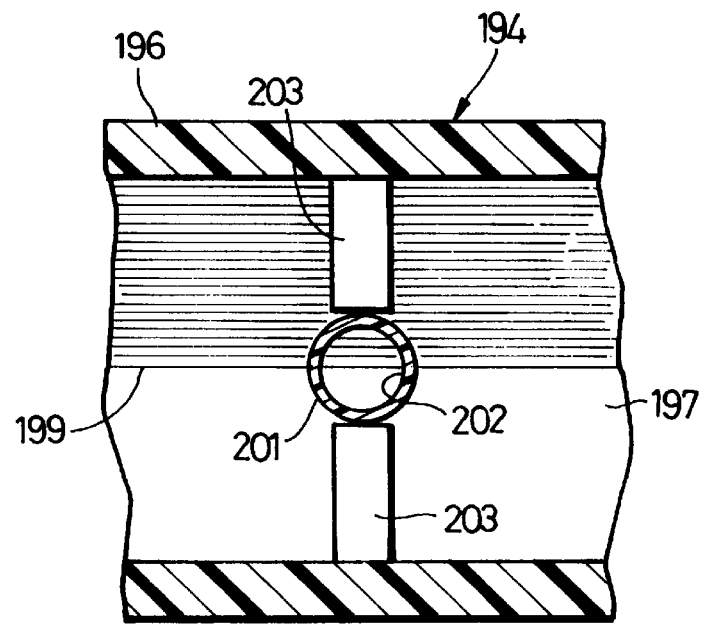
FIG. 29 is a sectional view taken along a line 29—29 in FIG. 11.

A sucking side of the treating pipe line 33 is passed through the bottom wall 83 of the electrolytic cell 12, and a sucking pipe 201, which is a terminal end thereof, rises within the electrode chamber 55 which is an electrode immersion zone. The sucking pipe 201 has a suction port 202 which is disposed in proximity to the portion of the ridgeline 199 of the roof-like portion 197 which is located at the higher elevation. The suction port 202 is inclined forwards and toward the ridgeline 199 in order to smoothly suck in the chlorine gas as best shown in FIGS. 7, 11 and 29, a pair of baffles 203 are provided on the hood 194 over opposed inner surfaces of the hood body 196 and the lower surface of the roof-like portion 197 to lie on opposite sides of the suction port 202. The baffles 203 act to prevent the chlorine gas from escaping from the suction port 202 and flowing toward the air venting through-hole 200.

The suction pipe 201 extends along the rear surface of the protruding plate 61 which is located on the left sidewall portion 48 of the electrolytic cell 12. The suction pipe 201 is fitted into a through-hole 205 in an annular member 204 which is projectingly provided on an upper portion of the rear surface of the protruding plate 61, and is held in a stationary state in the electrolytic cell 12

A chlorine gas collecting hood 194 and a suction pipe 201 similar to those described above are also in the right electrode chamber 55. Therefore, in the right electrode chamber 55, like reference characters are affixed to portions or components similar to those of the left electrode chamber 55.

As best shown in FIGS. 7, 8 and 14, the treating pipe line 33, including the two suction pipes 201, extends from the inside of the machine base 44 via mechanical section M along the outer surface of the rear wall portion 71 of the electrolytic cell 12. The line 33 is then bifurcated and enters two discharge ports 206 located in the rear wall portion 71 of the electrolytic cell 12. The discharge ports 206 open into portions of the heater chamber 68 in which the aqueous solution of NaCl 11 is stored.

As best shown in FIGS. 9 and 14, the suction pump 34 is disposed in the treating pipe line 33 in the mechanical section M. On the side of the outlet of the suction pump 34 in the treating pipe line 33, the chlorine gas purifying device 35 is disposed upstream, and the flow rate sensor 36 for detecting an abnormality of the treating system is disposed downstream. The suction pump 34 is mounted to a support member 207 on the machine base 44, and the chlorine gas purifying device 35 is mounted on a support 208 on the machine base 44. The suction pump 34 has a suction port 209 in its lower end face, and a discharge port 210 in a lower end of its outer peripheral surface.

A drainage pipe 211 diverges from the treating pipe line 33 at a location adjacent the suction side of the suction pump 34. The drainage pipe 211 has a manual cock 212 at its intermediate portion and is connected to the drainage pipe line 18 at a location downstream from the manual cock 32. The drainage pipe 211 is located at a level which is lower than the suction pump 34 and the chlorine gas purifying device 35. Thus, it is possible to withdraw water from the suction pump 34 and the chlorine gas purifying device 35.

The chlorine gas purifying device 35 includes a filter and a catalyst therein. The catalyst adsorbs the chlorine gas and decomposes NaClO and HClO which are, reaction products. The NaClO and HClO whiten the coating film 4 by their bleaching effects, so that the appearance of the coating film 4 is significantly different from a corroded state in a natural environment. Therefore, it is necessary to decompose NaClO and HClO If the chlorine gas treating device is constructed in the above manner, the chlorine gas generated around the carbon electrodes 13 immersed in the aqueous solution of NaCl 11 in the electrolytic cell 12 is immediately collected along with the aqueous solution of NaCl 11, released from the aqueous solution of NaCl 11, then purified by the chlorine gas purifying device 35. Thereafter, the aqueous solution of NaCl 11 is returned to the electrolytic cell 12.

In this case, the foamy chlorine gas generated in the vicinity of each of the carbon electrodes 13 is floated up in the aqueous solution of NaCl 11 and smoothly introduced in the form of a foam to the suction port 202 by a guiding effect of the chlorine gas collecting hood 194. In addition, the chlorine gas is effectively sucked in through the suction port 202 into the treating pipe line 33 by the baffles 203 for preventing the gas from escaping from the suction port. The generated chlorine gas cannot be accumulated within the hood 194 by virtue of the inclination of the lower surface of the hood 194. Furthermore, the accumulated chlorine gas cannot be vented and hence, the suction pump 34 cannot intake air.

Thus, the diffusion of the chlorine gas into the aqueous solution of NaCl within the electrolytic cell 12 is inhibited. Therefore, it is possible to inhibit the production of NaClO and HClO in the aqueous solution of NaCl 11 and the dissolution of the chlorine gas into the aqueous solution of NaCl 11 is inhibited to the maximum.

Figure 30:
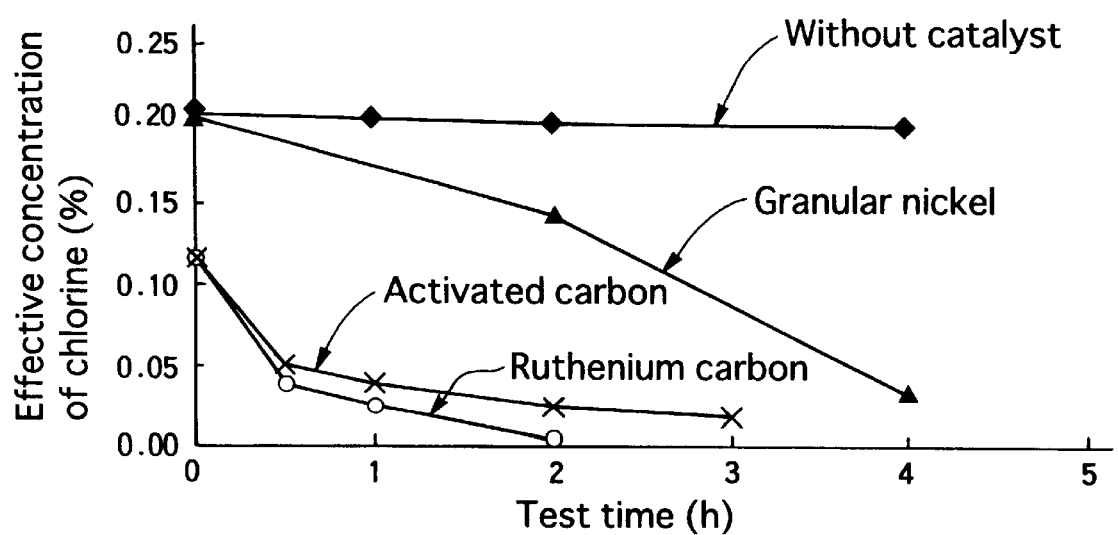
FIG. 30 is a graph illustrating a first example of the relationship between the test time and the effective concentration of chlorine.

FIG. 30 illustrates the relationship between the test time and the effective concentration of chlorine with regard to activated carbon, ruthenium carbon (a mixture of ruthenium and carbon) and granular nickel used as a catalyst in the chlorine gas purifying device 35. In FIG. 30, the term "effective concentration of chlorine" indicates a determined amount of chlorine gas dissolved in the aqueous solution of NaCl 11 (see Japanese Industrial Standard JIS K1425). In measuring the effective amount of chlorine, a procedure was employed which involves continuously supplying an electric current at 50 A for 20 hours while maintaining the temperature of the aqueous solution of NaCl 11 at 45° C., sampling 200 cc of the aqueous solution of NaCl 11, throwing the catalyst into the sampled aqueous solution of NaCl 11 the temperature of which is maintained at 45° C., and determining the effective concentration of chlorine after a lapse of a predetermined time. As apparent from FIG. 30, the activated carbon and the ruthenium carbon, having an excellent effective chlorine decomposing capability, are effective as the catalyst used in the chlorine gas purifying device 35.

Figure 31:
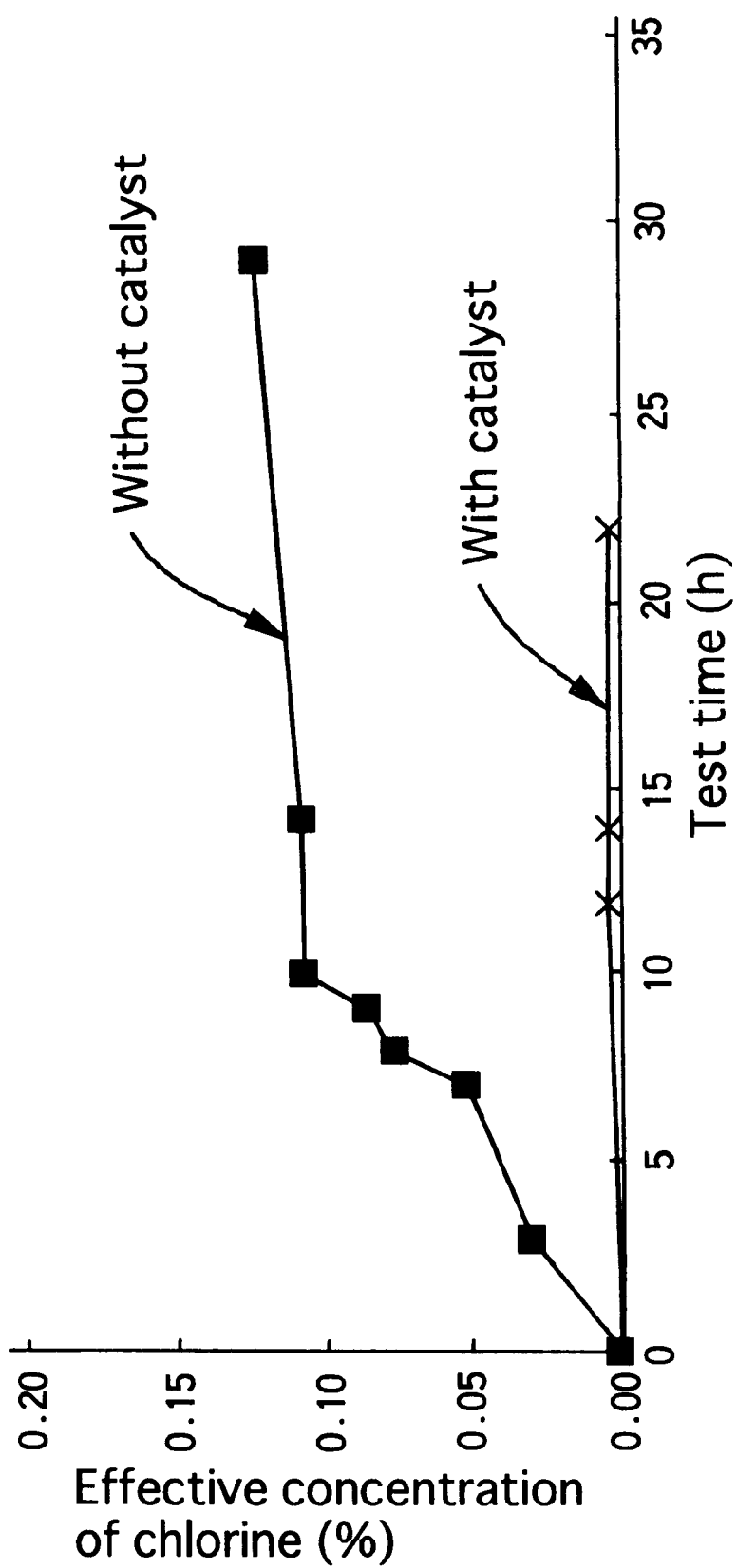
FIG. 31 is a graph illustrating a second example of the relationship between the test time and the effective concentration of chlorine.

FIG. 31 illustrates the relationship between the test time and the effective concentration of chlorine when activated carbon was used as the catalyst. Conditions for the test are such that an electric current of 50 A is supplied continuously, and the temperature of the aqueous solution of NaCl 11 is 45° C. As apparent from FIG. 31, if the above-described treating device 6 is used, and activated carbon is used as the catalyst, the effective concentration of chlorine can be maintained at an extremely low value such as about 0.003% or lower, even after the test time exceeds 20 hours.

Figure 32:
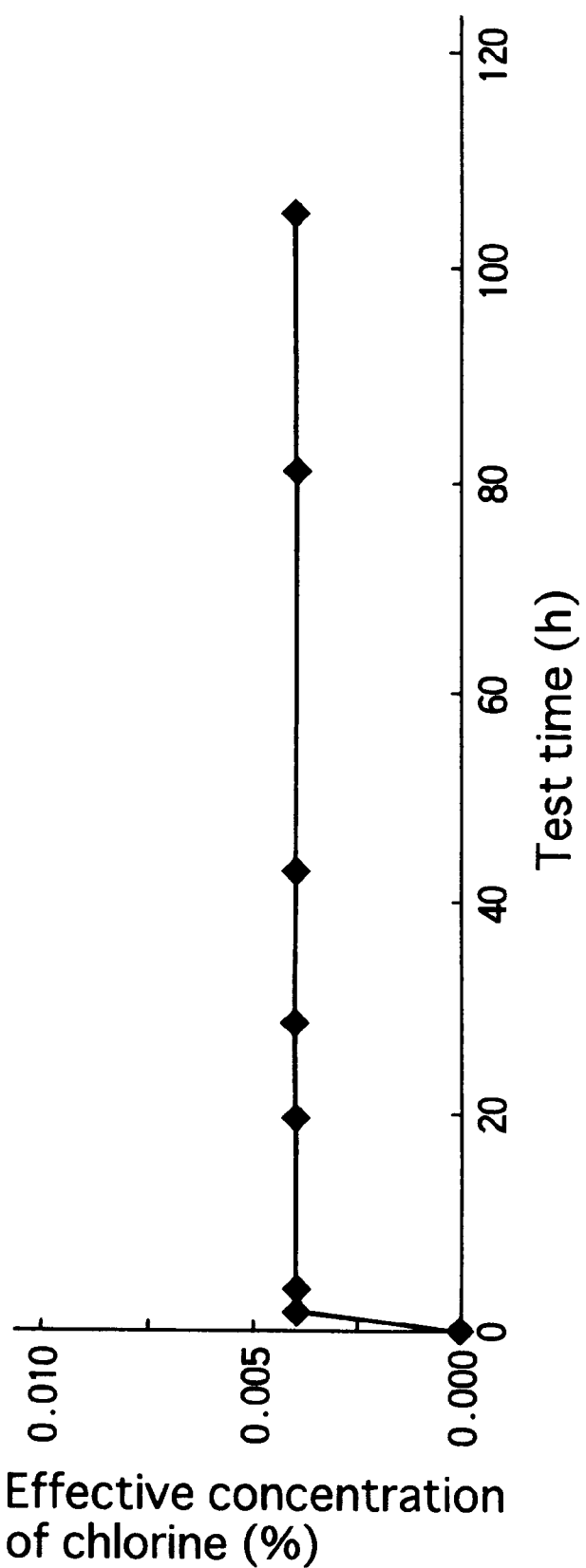
FIG. 32 is a graph illustrating a third example of the relationship between the test time and the effective concentration of chlorine.

FIG. 32 illustrates the test time and the effective concentration of chlorine when electric current of 20 A was continuously supplied at a temperature of the aqueous solution of NaCl 11 equal to 45° C. In this case, the effective concentration of chlorine can be maintained at about 0.004% or lower, even after the test time exceeds 100 hours.

As a result of the various tests, it was confirmed that if the effective concentration of chlorine is equal to or lower than 0.005%, the whitening of the coating film 4 does not occur.

$Na^+$ ion and $OH^-$ ion are contained in the aqueous solution of NaCl. Therefore, if the chlorine gas is collected along with the aqueous solution of NaCl, chemical reactions represented by the following chemical formulae occur between NaOH and the chlorine gas, thereby causing a portion of chlorine gas to be regenerated as NaCl. The regenerated NaCl is returned into the electrolytic cell 12 to contribute to the suppression of a variation in concentration of NaCl in the aqueous solution of NaCl 11.

$$Cl_2 + NaOH \rightarrow NaCl + HClO$$

$$Cl_2 + 2NaOH \rightarrow NaCl + NaClO + H_2O$$

The chlorine gas decomposing reaction as described above is promoted more, when the amount of NaOH is large.

Therefore, attention of the present inventors was drawn to the fact that NaOH attendant on the electrolysis of the aqueous solution of NaCl 11 is produced in the test material immersion zone within the electrolytic cell 12 due to the polarity of the test material 2 being set at a cathode. The electrolytic test machine 1 is arranged so that NaOH produced in the test material immersion zone can be introduced to both electrode chambers 55.

HClO and NaClO, produced by both the above-described chemical reactions as well as HClO and NaClO produced within the electrolytic cell 12 during the test and collected along with the chlorine gas, are decomposed mainly by chemical reactions with activated carbon (including ruthenium carbon) C of the chlorine gas purifying member 35. These reactions are represented by the following reaction formulae:

$$2NaClO + C \rightarrow 2NaCl + CO_2 \uparrow$$

$$2HClO + C \rightarrow 2HCl + CO_2 \uparrow$$

The regenerated NaCl is likewise returned into the electrolytic cell 12 to contribute to the suppression of a variation in concentration of NaCl in the aqueous solution of NaCl 11. The produced HCl is returned into the aqueous solution of NaCl 11 and neutralized by a reaction with NaOH produced by the electrolysis. This also regenerates NaCl.

As can be seen from the above-described chemical reaction formulae, activated carbon C is wasted in the form of $CO_2$. The activated carbon is wasted because it decomposes NaClO and HClO. Therefore, if NaClO and the like are previously decomposed in another method to decrease the amount of NaClO and the like which are to be loaded to the activated carbon, the load of the activated carbon can be alleviated to provide a prolongated life for the activated carbon.

Since the electrolytic testing machine 1 is arranged so that NaOH, produced in the test material immersion zone, can be introduced into both electrode chambers 55, a chemical reaction which is represented by the following reaction formula:

$$2HClO + NaClO + 2NaOH \rightarrow NaClO_3 + 2NaCl + 2H_2O$$

can be produced to eliminate predetermined amounts of HClO and NaClO, thereby alleviating the load of the activated carbon.

Figure 33:
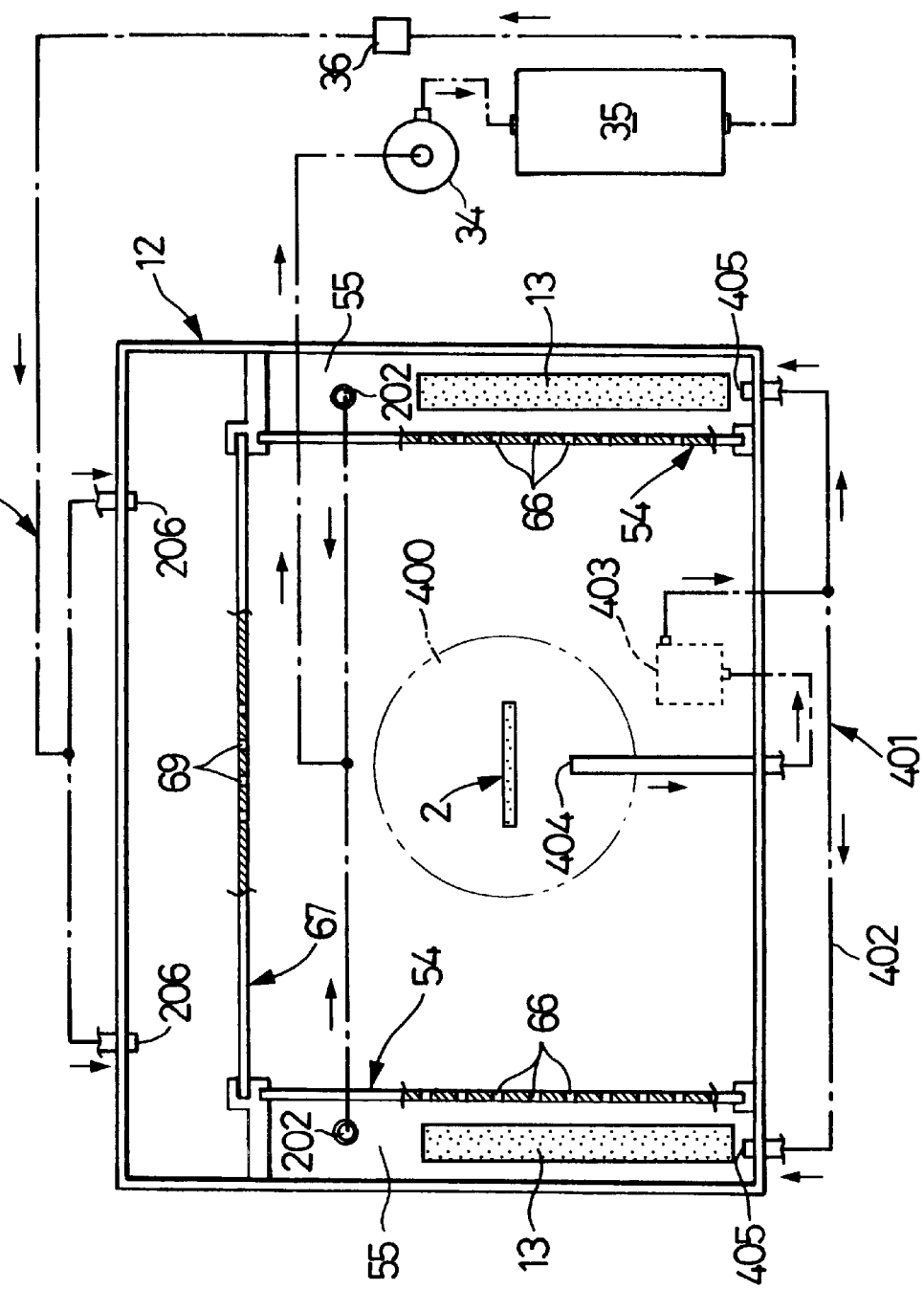
FIG. 33 is an illustration of a piping in the electrolytic test machine.

FIG. 33 shows an NaOH introducing device 401 mounted in the electrolytic cell 12 for introducing NaOH produced in a test material immersion zone 400 within the electrolytic cell 12 to both electrode chambers 55. The NaOH introducing device 401 includes an introducing pipe line 402, and a suction pump 403 disposed in the introducing pipe line 402. The introducing pipe line 402 has an inlet 404 disposed in the test material immersion zone 400, and two outlets 405 disposed in both electrode chambers 55, respectively.

Figure 34:
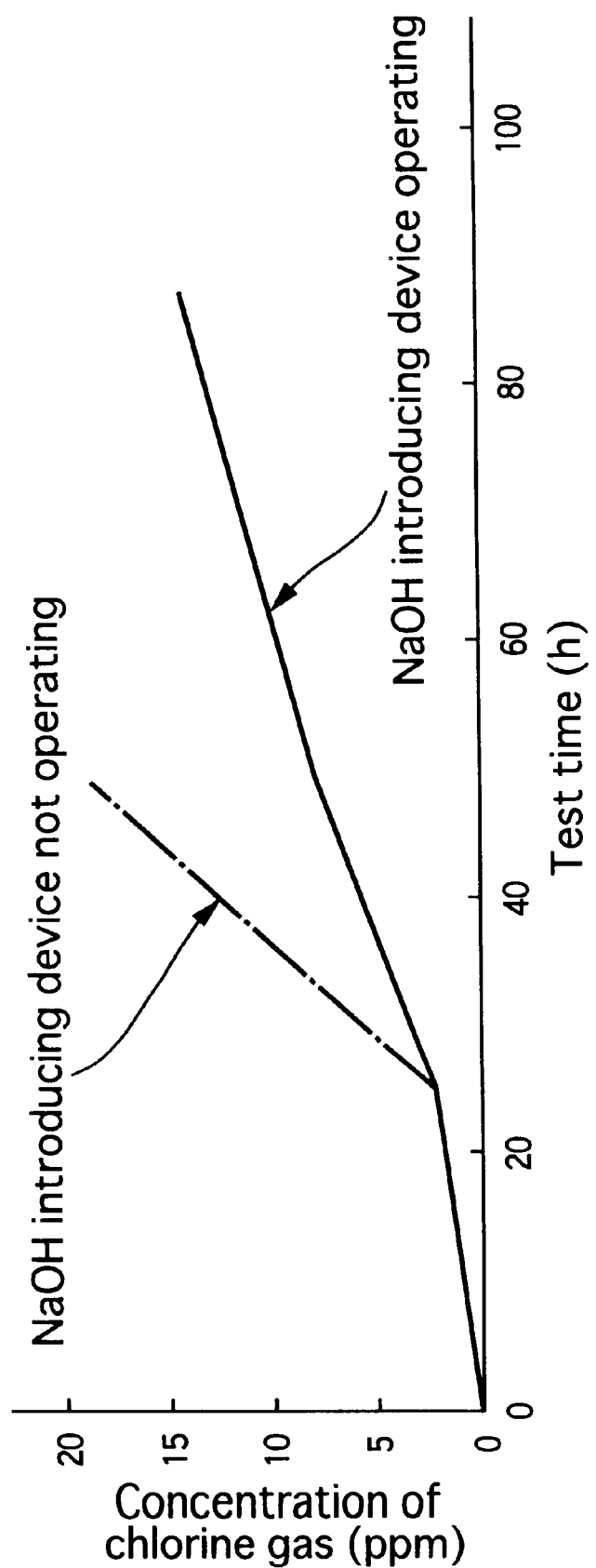
FIG. 34 is a graph illustrating a first example of the relationship between the test time and the concentration of a chlorine gas.

FIG. 34 illustrates the relationship between the testing time and the concentration of chlorine gas above a liquid level f within the electrolytic cell 12, when the NaOH introducing device 401 has been operated and when the device 401 has not been operated. Testing conditions are as follows: Electric current of 20 A is continuously supplied; the amount of activated carbon is 550 g; and the temperature of the aqueous solution of NaCl 11 is 45° C. As can be seen from FIG. 34, if about 25 hours lapse from the start of the test under non-operation of the device. 401, the concentration of chlorine gas is suddenly increased. This is due to wasting of the activated carbon. However, if the device 401 is operated the concentration of chlorine gas is gradually increased, thereby the waste of the activated carbon is suppressed which prolongs its service life.

If the amount of activated carbon is increased more than that in the above-described case, the wasting timing can be retarded. The reason why the amount of the activated carbon is set at a small value is for shortening the testing time. The amount of the activated carbon is set at about 1 kg in the actually operated electrolytic testing machine 1. Granular nickel as a catalyst is wasted in the form of nickel oxide, as NaClO and NClO are decomposed. Even in this case, if the NaOH introducing device 401 is used, the granular nickel has a prolonged life.

In the treating device 6, the flow rate of the aqueous solution of NaCl 11 flowing downstream from the chlorine gas purifying device 35 is measured by the flow rate sensor 36. Therefore, for example, if the chlorine gas purifying device 35 is not clogged and is operating normally, the flow rate sensor 36 measures a corresponding flow rate. On the other hand, if the chlorine gas purifying device 35 is clogged, the flow rate is decreased more than when the chlorine gas purifying device 35 is operating normally. Therefore, the flow rate sensor 36 measures such a decreased flow rate.

With the above-described construction, an abnormality of the treating system can be easily and reliably detected. In addition, since the flow rate sensor 36 is disposed downstream from the chlorine gas purifying device 35, so that fine foreign matter entering the treating pipe line 33 is caught by the chlorine gas purifying device 35, the operation of the flow rate sensor 36 cannot be obstructed by the foreign matter. Thus, the accuracy of the flow rate sensor 36 can be maintained over a long period of time.

(2) Abnormal-point Detector in Treating System (FIGS. 4 to 6 and 35 to 37)

Figure 35:
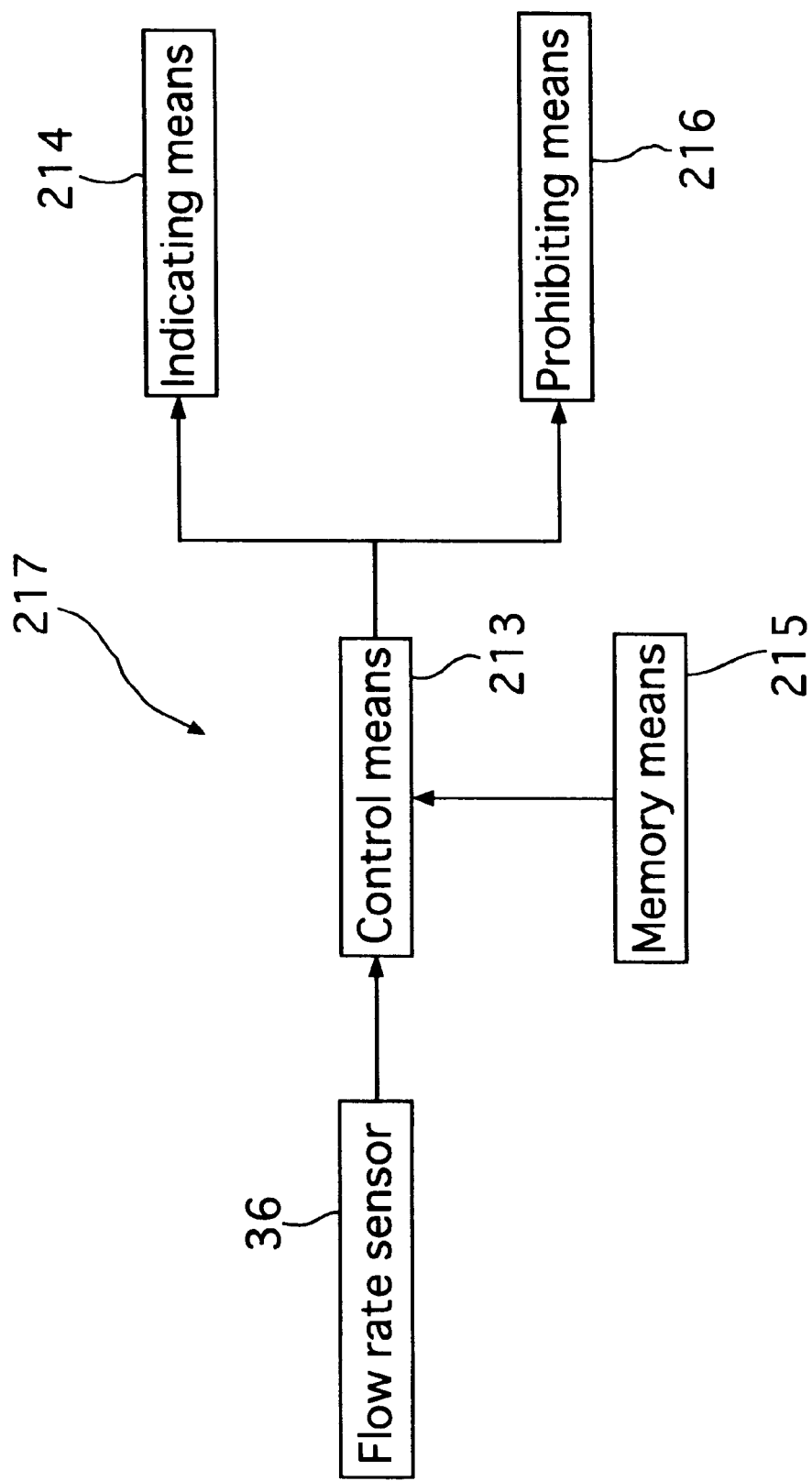
FIG. 35 is a block diagram of an abnormal-point detector in a chlorine gas treating device.

Referring to FIG. 35, the flow rate sensor 36 has a function to transmit an abnormality signal which varies depending upon the type of abnormality occurring in the treating system. A control means 213 is connected to the flow rate sensor 36 and discriminates the type of abnormality based on the abnormality signal from the flow rate sensor 36. The contrast means 213 transmits an output signal corresponding to the type of abnormality. An indicating means 214 is connected to the control means 213 for indicating the type of abnormality corresponding to the output signal from the control means 213.

Figure 36:
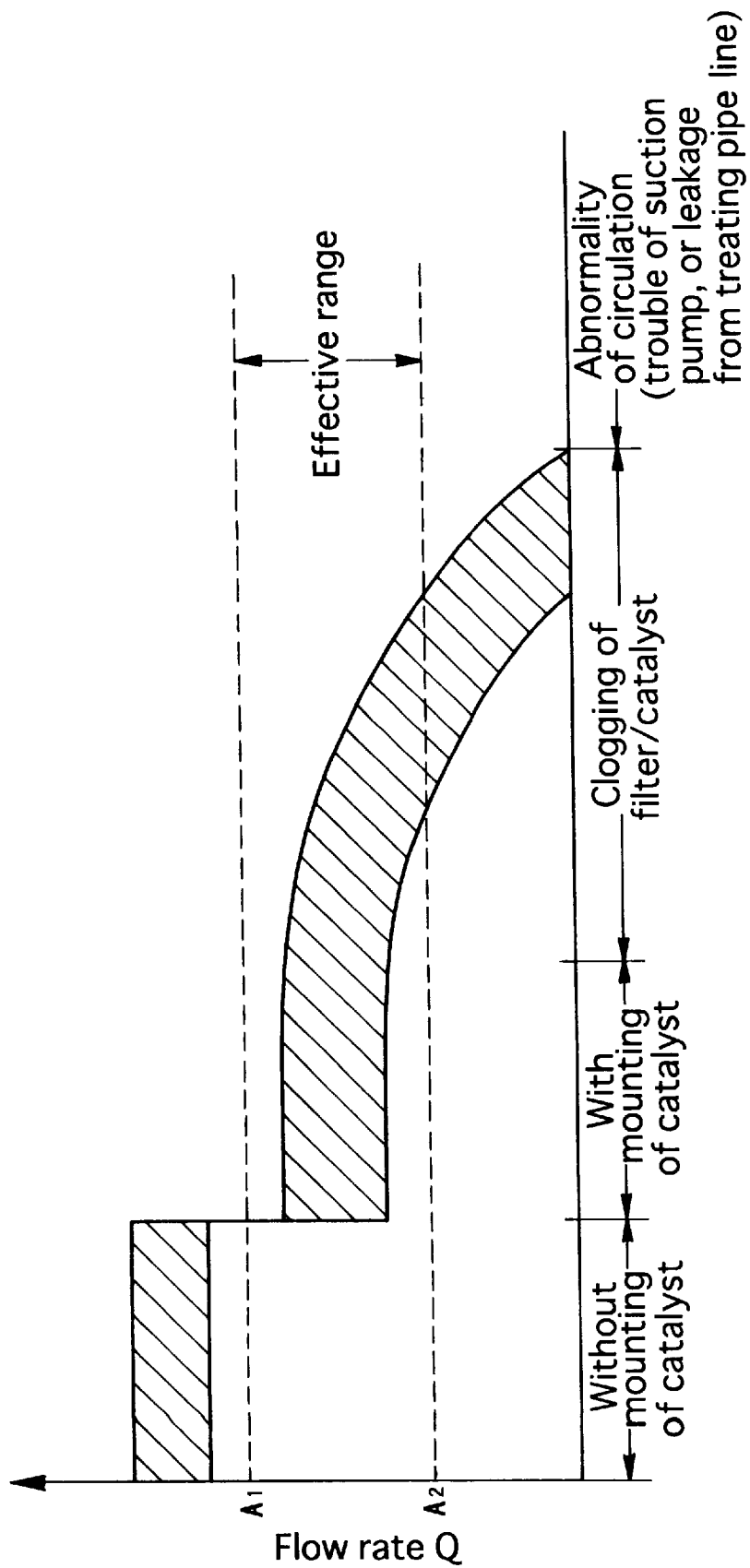
FIG. 36 is a graph illustrating the relationship between the situation of a treating system and the flow rate.

A memory means 215 is connected to the control means 213. An effective range of flow rate Q, namely, $A2 \leq Q \leq A1$ which is a range between an upper limit value A1 and a lower limit value A2 of flow rate, is previously stored in the memory means 215, as shown in FIG. 36. Further, a prohibiting means 216 is connected to the control means 213 for prohibiting electric current to be supplied to the carbon electrodes 13 in accordance with the output signal from the control means 213.

Figure 4:
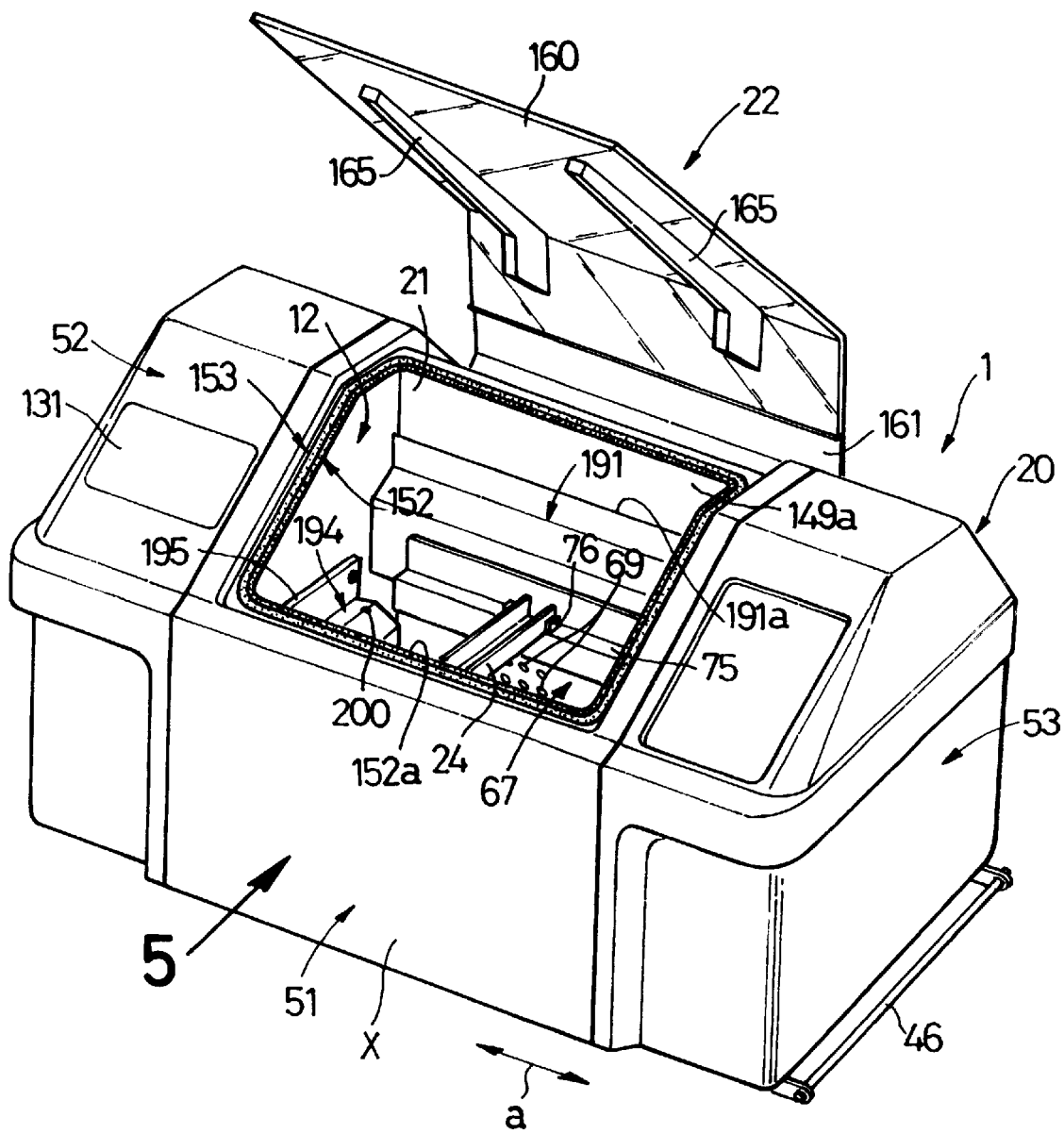
FIG. 4 is a perspective view of the electrolytic test machine.
Figure 5:
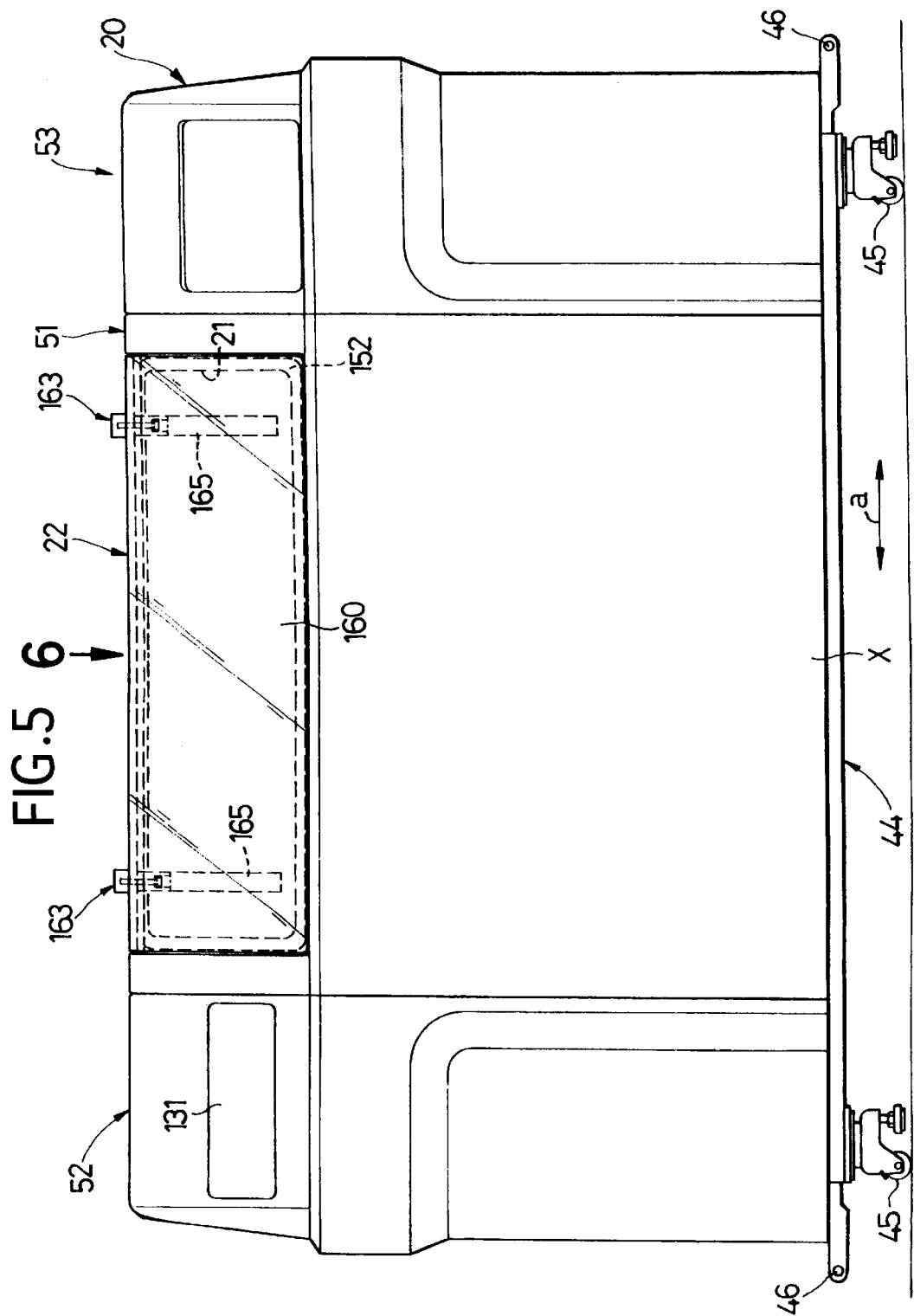
FIG. 5 is a front view of the electrolytic test machine, which corresponds to a view taken along an arrow 5 in FIG. 4.

These means 213 to 216 are incorporated in the computer programmed control unit 10 to constitute an abnormal-point detector 217 for the treating system together with the flow rate sensor 36. The indicating means 214 indicates, for example, a message which is displayed by characters on a liquid crystal display plate 131 on the upper surface of the left cover section 52 covering the control section C, as best shown in FIGS. 4 to 6. The prohibiting means 216 is operated to control the DC power source 9 to its OFF state.

Figure 37:
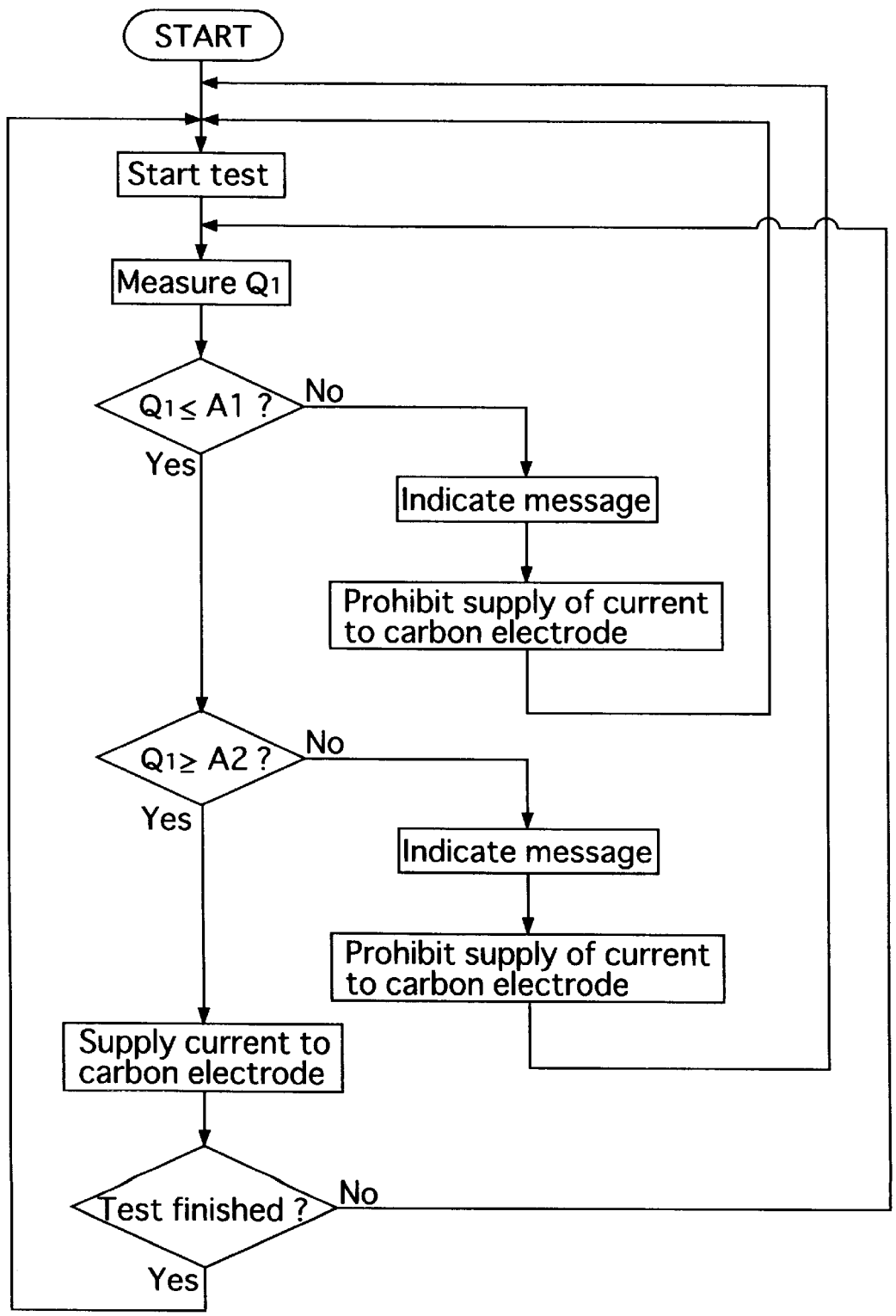
FIG. 37 is a flow chart illustrating the operation of the abnormal-point detector.

As shown in FIGS. 35 and 37, if a signal indicative of a command to start the test is input, the flow rate sensor 36 measures a flow rate $Q_1$ of the aqueous solution of NaCl 11 flowing in the treating pipe line 33. If the measured flow rate Q1 is in the effective range of $A2 \leq Q_1 \leq A1$, the control means 213 determines that the flow rate sensor 36 is transmitting a normal signal and thus, the carbon electrodes 13 are energized to start the corrosion test.

If the measured flow rate Q1 is larger than A1, the control means 213 determines that the flow rate sensor 36 is transmitting an abnormality signal. The abnormality signal corresponds to the non-mounting of the catalyst in the chlorine gas purifying device 35. Thus, a message "stop the test because of the non-mounting of the catalyst" is indicated by the indicating means 214, and electric current is prohibited from being supplied to the carbon electrodes 13 by the prohibiting means 216.

If the flow rate Q1 measured in the flow rate sensor 36 is smaller than A2, operations similar to those described above are carried out. However, a message "stop the test" is indicated by the indicating means 214, because the filter or catalyst is clogged, a circulation abnormality or the like has been produced.

The abnormal-point detector 217 for the treating system is controlled so that it is operated even during the corrosion test.

Any problems of the treating system can be easily and reliably detected by the detector 217 to precisely inform testing personnel of the problem. The detector 217 is relatively inexpensive because of its simple construction.

(3) Chlorine Gas Purifying Device (FIGS. 7, 9 and 38 to 40)

Figure 38:
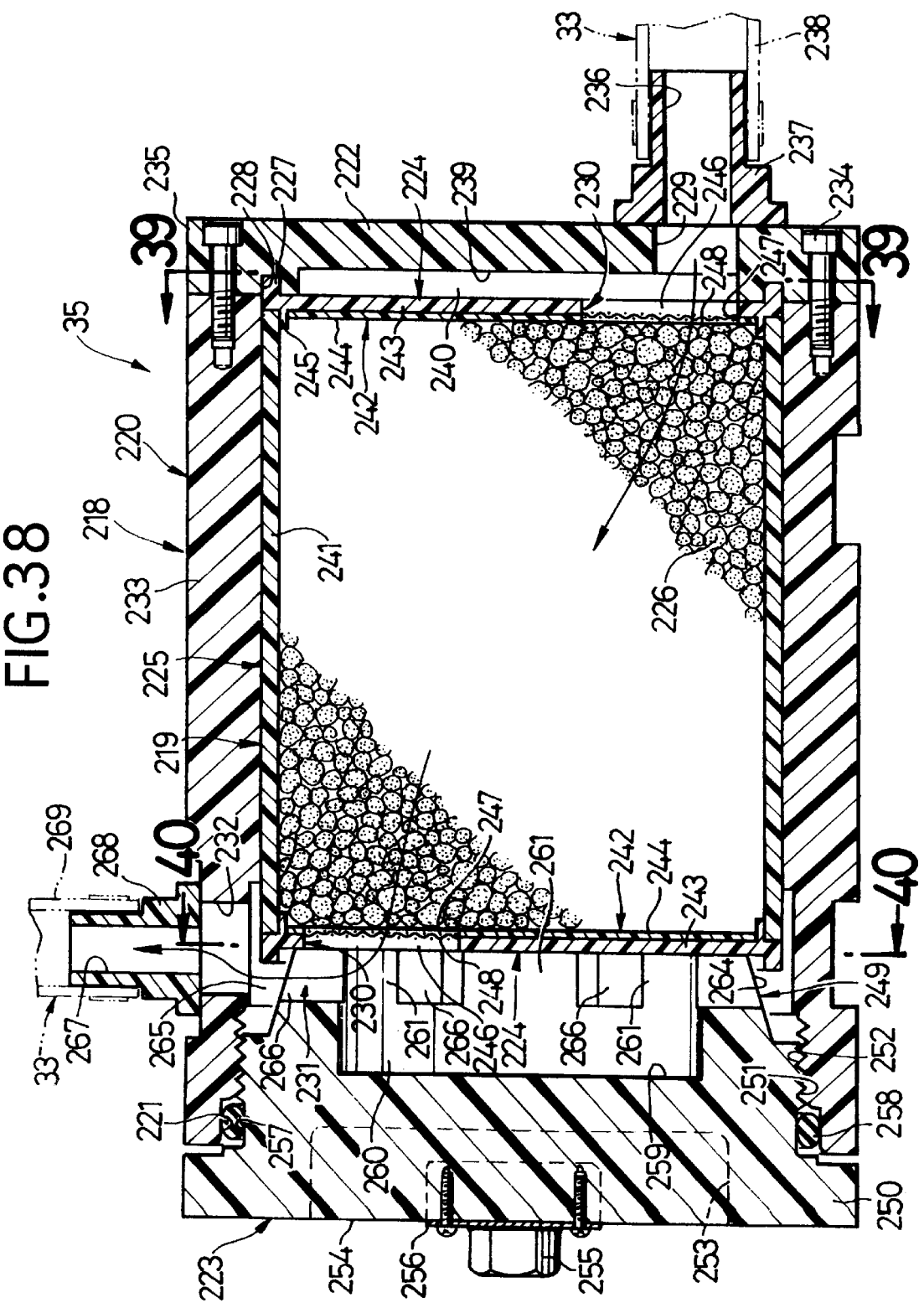
FIG. 38 is a vertical sectional side view of a chlorine gas purifying member, which corresponds to a sectional view taken along a line 38—38 in FIG. 7.

As best shown in FIG. 38, the chlorine gas purifying device 35 is comprised of an outer shell 218 made of a synthetic resin, and a tubular catalyst unit 219 accommodated in the outer shell 218. The outer shell 218 is comprised of a bottomed tubular body 220 into which the catalyst unit 219 is fitted, and a lid 223 capable of being attached to and detached from an opening 221 in the body 220. The lid 223 closes the opening 221 to urge the catalyst unit 219 to a bottom wall 222 of the body 220. The catalyst unit 219 is comprised of a tubular member 225 made of a synthetic resin and having end walls 224 at opposite ends thereof, and an activated carbon 226 as a catalyst accommodated in the tubular member 225.

One of the end walls 224 and the bottom wall 222 of the bottomed tubular body 220, e.g., an annular projection 227 located on the end wall 224 in the illustrated embodiment, is fitted into the other, i.e., an annular recess 228 provided in the bottom wall 222, so that an inlet 229 for the aqueous solution of NaCl, provided in the bottom wall 222 at a location between the projection 227/recess 228 fit portions, communicates with a through-hole 230 provided in the end wall 224. The through-hole 230, provided in the other end wall 224 of the catalyst unit 219, communicates with an outlet 232 for the aqueous solution of NaCl in a peripheral wall of the bottomed tubular body 220 through a passage 231 in the lid 223.

In the outer shell 218, the bottomed tubular body 220 is comprised of a cylinder 233 and a circular end plate 235. The end plate 235 is mounted to one end face of the cylinder 233 by a plurality of bolts 234 to form the bottom wall 222.

A liquid sealant is applied to one end face of the cylinder 233 against which the circular end plate 235 abuts. A connector 237, made of a synthetic resin, is bonded to an outer surface of the circular end plate 235 and has a through-hole 236 communicating with the inlet 229. A pipe 238, which is a portion of the treating pipe line 33, extends from the outlet 210 of the suction pump 34, as also shown in FIG. 9, and is connected to the connector 237.

The circular end plate 235 has a circular recess 239, provided in its inner surface at a location between the annular recess 228, and a space 240 for flowing of the aqueous solution of NaCl. The space 240 is defined by cooperation of the circular recess 239 and the end wall 224 of the catalyst unit 219. The space 240 communicates with the inlet 229 and the through-hole 230.

Figure 39:
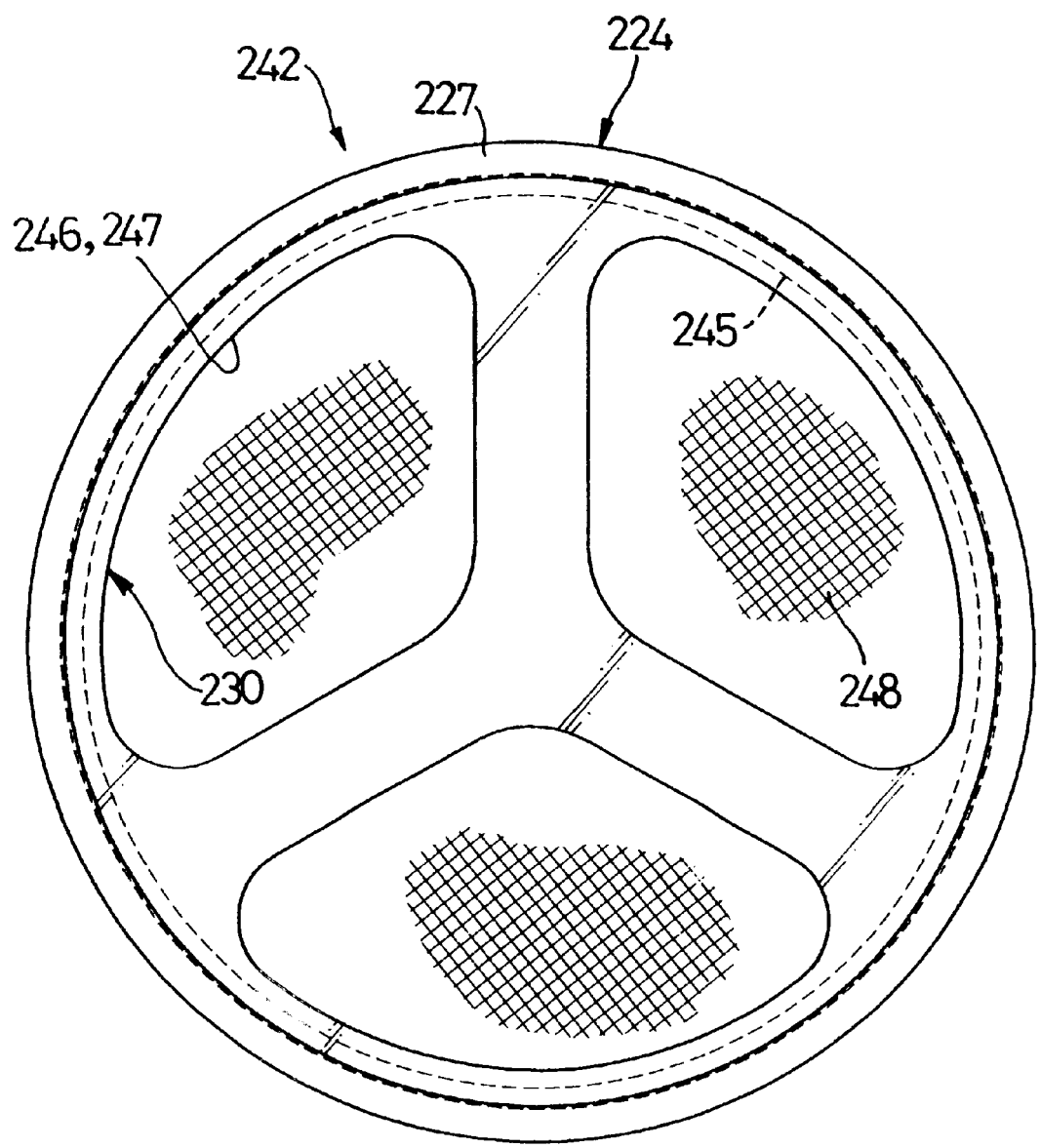
FIG. 39 is an end view of a catalyst unit, which corresponds to a view taken along a line 39—39 in FIG. 38.

The tubular member 225 of the catalyst unit 219 is comprised of a cylinder 241 and a pair of circular end plates 242 mounted to openings at opposite ends to form the end walls 224 and both end plates 242 have the same structure. The circular end plate 242 includes an outer plate 243 and an inner plate 244. The outer plate 243 has the annular projection 227 on an outer periphery of its outer surface, and also has an annular projection 245 fitted into and bonded in an opening in the cylinder 241 in the vicinity of an outer periphery of its inner surface. Further, the outer plate 243 has a plurality of openings 246, as also shown in FIG. 39, so that they open into an area surrounded by the annular projections 227 and 245. A net-like filter 248, made of a synthetic resin, is placed in the entire area surrounded by the inner annular projection 245 of the outer plate 243, and the inner plate 244 having a plurality of openings 247 matched with the openings 246 in the outer plate 243 is fitted into and bonded in such an area. A plurality of through-holes 230 are defined by the opposed openings 246 and 247 in the inner and outer plates 244 and 243 for permitting the communication between the flowing space 240 and the inside of the tubular member 225 of the catalyst unit 219. A filter 248 is located in each of the through-holes 230.

Figure 40:
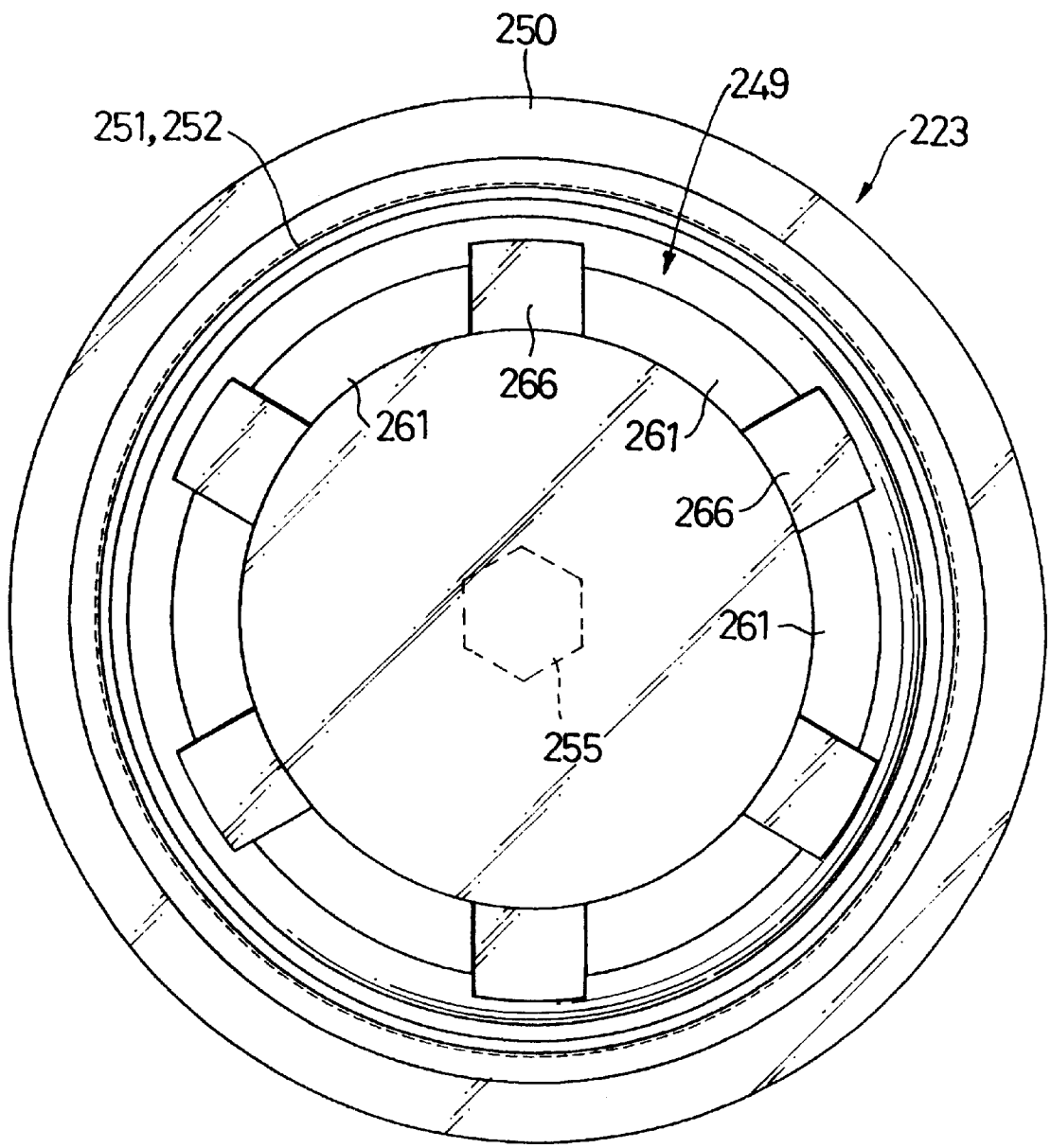
FIG. 40 is an end view of a lid, which corresponds to a view taken along a line 40—40 in FIG. 38.

As also shown in FIG. 40, the lid 223 includes a circular tubular portion 249, and a circular flange portion 250 connected to an outer end of the circular tubular portion 249. External threads 251 on an outer peripheral surface of the circular tubular portion 249 are threadedly engaged with internal threads 252 on an inner peripheral surface of the opening 221 in the bottomed tubular body 220. A fitment 256, having a hexagonal head 255, is mounted to a projection 254 between a pair of half moon-shaped recesses 253 located in an outer surface of the circular flange portion 250. In carrying out the above-described threaded engagement, a tool is brought into engagement with the hexagonal head 255. A ring groove 257 is defined in the circular tubular portion 249 on the side of the flange portion 250. The circular tubular portion 249 and the opening 221 in the bottomed tubular body 220 are sealed therebetween by a seal ring 258 made of a rubber and mounted in the ring groove 257.

The circular tubular portion 249 has a circular recess 259 in its inner surface, and an NaCl aqueous solution flowing space 260 is defined by cooperation of the circular recess 259 and the end walls 224 of the catalyst unit 219 to communicate with the through-holes 230. A plurality of projections 261 are disposed at equal distances around the circular recess 259, so that an end face of each of the projections 261 is urged against the end wall 224 of the catalyst unit 219. That portion of an outer peripheral surface of the circular tubular portion 249, which is between the external threads 251, is formed into a tapered surface 264. A flowing space 265 is defined between the tapered surface 264 and an inner peripheral surface of the bottomed tubular body 220 to communicate with the outlet 232. A space 266 is defined between the adjacent projections 261 and communicates with the flowing spaces 260 and 265. Therefore, the flowing spaces 260 and 265 and the space 266 form the passage 231.

A connector 268, made of a synthetic resin and having a through-hole 267 communicating with the outlet 232, is bonded to the outer peripheral surface of the bottomed tubular body 220. A pipe member 269, of the treating pipe line 33, is connected to the connector 268, as shown in FIG. 9.

In the outer shell 218, the inlet 229 and the outlet 232 are disposed on opposite sides of an axis of the outer shell 218.

As best shown in FIG. 9, the chlorine gas purifying device 35 is disposed on the machine base 44 through the support 208 in an inclined manner such that the outlet 232 thereof lies at an upper location and the inlet 229 thereof lies at a lower location. In this case, the inclination angle β is set at a value such that when the aqueous solution of NaCl 11 within the bottomed tubular body 220 has been withdrawn from the inlet 229 through the suction pump 34 and the drainage pipe 211 for the purpose of replacing the catalyst unit 219, the liquid level of the remaining aqueous solution of NaCl 11 lies below the opening 221 in the body 220.

If the chlorine gas purifying device 35 is constructed in the above-described manner, the aqueous solution of NaCl 11 including the chlorine gas is reliably introduced into the catalyst unit 219 without entering from the inlet 229 and without being between the outer peripheral surface of the tubular member 225 of the catalyst unit 219 and the inner peripheral surface of the bottomed tubular body 220 of the outer shell 218, by virtue of a labyrinth structure formed by the recess-projection fit portions 228 and 227. Therefore, it is possible to enhance the purification rate of the chlorine gas.

In this case, the catalyst unit 219 is urged against the bottom wall 222 of the outer shell 218 by the lid 223. Hence, the labyrinth structure is reliably formed and maintained. The closure of the labyrinth structure is easily determined by the condition of mounting of the lid 223 to the bottomed tubular body 220. For example, the incomplete closure of the labyrinth structure is confirmed by the fact that the seal ring 258 can be viewed from a gap between the flange portion 250 and the body 220.

The chlorine gas purifying device 35 is disposed in the inclined manner such that the outlet 232 is turned upwards, as described above. Therefore even when the unpurified chlorine gas is present in the device 35, the accumulation of the unpurified chlorine gas can be inhibited to the maximum extent.

Moreover, since the provision of the outlet 232 is not in the lid 223, the mounting and removal of the lid 223 can be easily performed, and the formation of the lid 223 and the catalyst into one unit ensures that the operation of replacing the catalyst can be efficiently performed. In addition, even if the lid 223 is removed from the bottomed tubular body 220 after withdrawal of water, the dropping of the remaining aqueous solution of NaCl from the opening 221 in the body 220 can be prevented by the inclined disposition of the chlorine gas purifying device 35.

The opposite end walls 224 in the catalyst unit 219 have the same structure. Hence, in fitting the catalyst unit 219 into the bottomed tubular body 220 to fit the annular projection 227 into the annular recess 228, the catalyst unit 219 may be fitted into the body 220 from either end wall 224. Thus, it is easy to mount the catalyst unit 219.

The labyrinth structure in the chlorine gas purifying device 35 may be omitted in some cases.

(4) Determining Device for Determining Timing of Replacement of Catalyst (FIGS. 4 to 6, 41 and 42)

The purifying capability of the activated carbon 226, which is used as the catalyst, is decreased in accordance with the product of the electric current flowing across the carbon electrode 13 and time. Therefor, in order to replace the activated carbon 226 by a new activated carbon 226, e.g., the catalyst unit 219 in this embodiment before the purifying capability of the activated carbon 226 in service is completely lost, a determining device 270 is mounted in the electrolytic test machine 1. The determining device 270 is incorporated in the computer programmed control unit 10.

Figure 41:
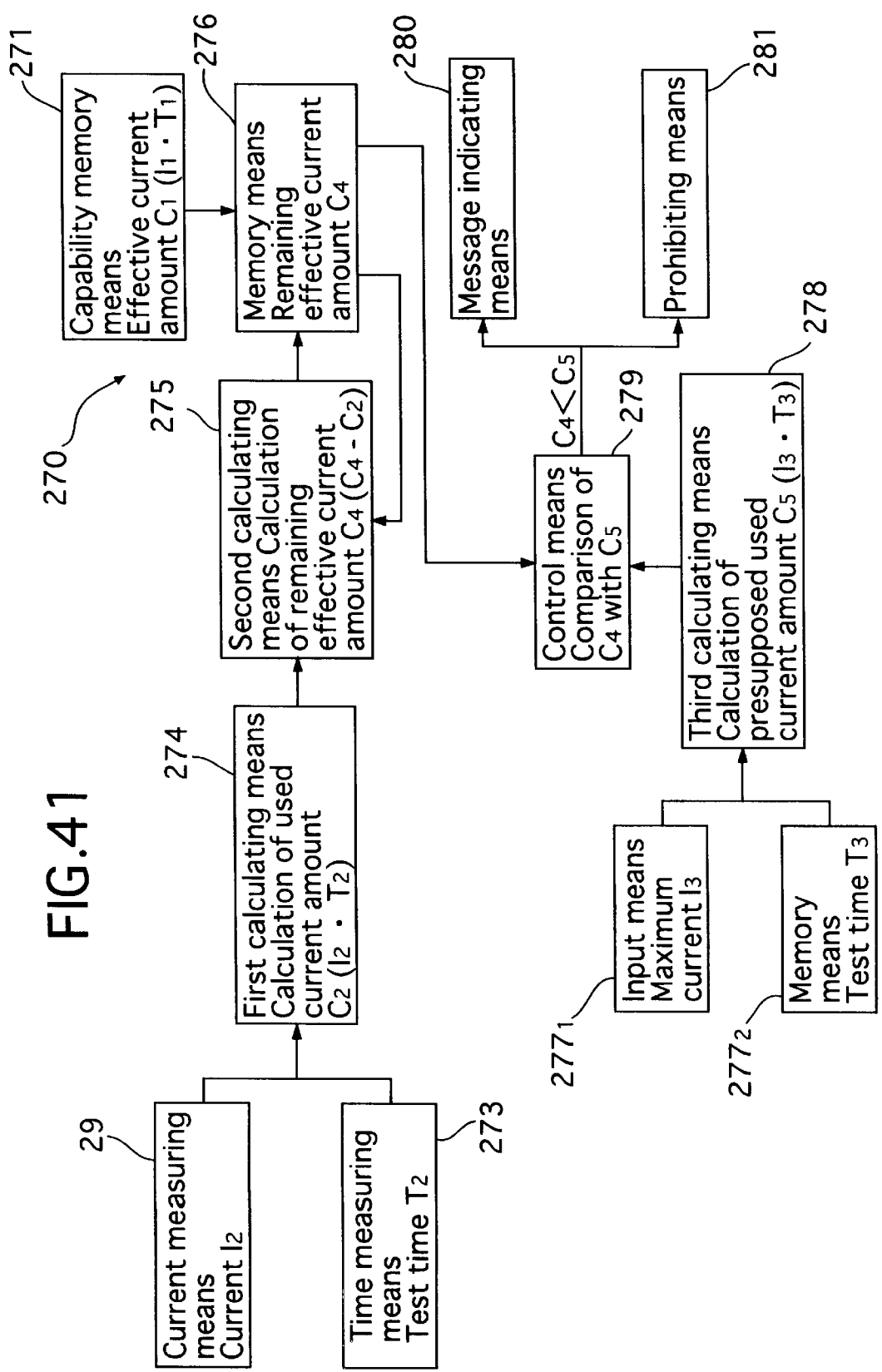
FIG. 41 is a block diagram of a determining device for determining a replacement time of a catalyst.
Figure 42:
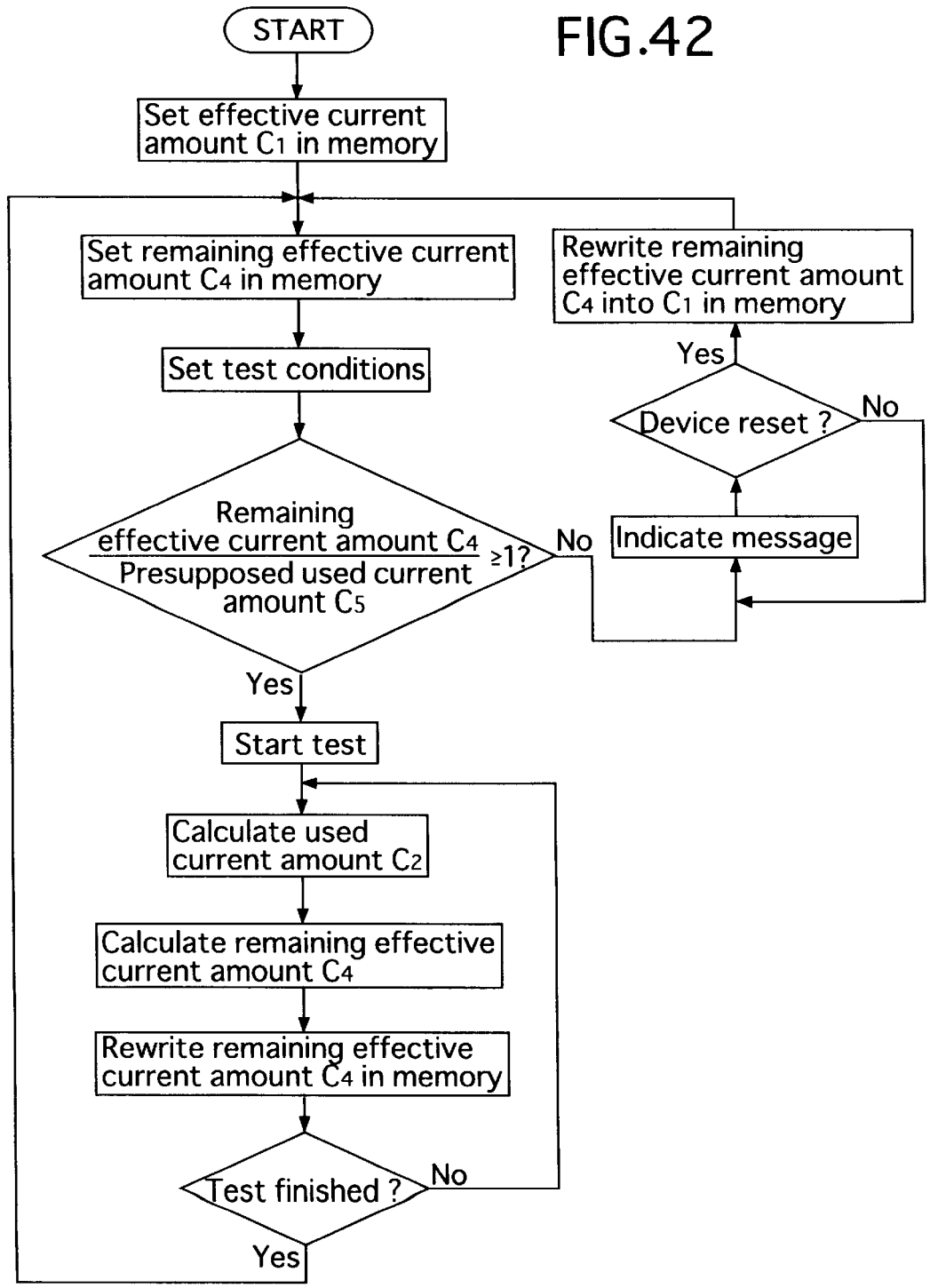
FIG. 42 is a flow chart illustrating the operation of the determining device for determining the replacement time of the catalyst.

FIG. 41 is a block diagram of the determining device 270, and FIG. 42 is a flow chart illustrating the operation of the determining device 270. The term "set test conditions" in FIG. 42 means that any of the following testes are selected: a) the corrosion test including the coating film peeling-off step and the steel plate corroding step, b) the coating film peeling-off test, and c) that the test is to be finished. Conditions selected are then input.

Referring to FIG. 41, the determining device 270 includes a capability storage means 271 for storing the purifying capability of the activated carbon 226 in the form of an effective current amount $C_1$ which is a product $I_1 \cdot T_1$ of a certain current $I_1$ flowing across the carbon electrode 13 and a total test time $T_1$ usable when the current $I_1$ continues to flow. A memory means 276 stores the effective current amount $C_1$ in the form of a remaining current amount $C_4$. A current measuring means (ammeter) 29 measures a current $I_2$ flowing across the carbon electrode 13 during a test. A time measuring means 273 measures a test time $T_2$. A first calculating means 274 calculates a used current amount $C_2$ which is a product $I_2 \cdot T_2$ Of the current $I_2$ and the test time $T_2$. A second calculating means 275 subtracts the used current amount $C_2$ from the remaining current amount $C_4$ to provide a new remaining effective current amount and stores the latter in the memory means 276. An input means $277_1$ inputs a maximum current $I_3$ of the DC power source 9 at the start of the test. A memory means $277_2$ stores a test time $T_3$. A third calculating means 278 calculates a presupposed used current amount $C_5$ which is a product $I_3 \cdot T_3$ of the maximum current $I_3$ and the test time $T_3$. A control means 279 compares the remaining effective current amount $C_4$ and the presupposed used current amount $C_5$ with each other and transmits a catalyst replacing signal, when $C_4 < C_5$.

If the determining device 270 is constructed in the above manner, it is possible, before the test is carried out, to automatically detect that the replacement time of the activated carbon 226 has been reached due to a decrease in purifying capability of the activated carbon 226.

The determining device also includes a) a message indicating means 280 adapted to inform testing personnel that the catalyst replacing timing has been reached based on the catalyst replacing signal from the control means 279, and b) a prohibiting means 281 which prohibits current to be supplied to the carbon electrodes 13.

As best shown in FIGS. 4 to 6, a message indicated in the message indicating means 280 is displayed on a liquid crystal display plate 131 mounted on the upper surface of the left cover section 52 covering the control section C. The prohibiting means 281 is operated to maintain the DC power source 9 in its OFF state. Thus, testing personnel can reliably know the replacement time of the activated carbon 226.

As shown in FIG. 42, the determining device 270 is constructed so that the device 270 will not operate after replacement of the catalyst unit 219 unless the remaining effective current amount $C_4$ stored in the memory means 276 is reset to a relation of $C_4=C_1$.

If the remaining effective current amount $C_4$ and the presupposed used current amount $C_5$ are in a relation of $C_4 \geq C_5$ prior to starting the test, the test is started, and the calculation of the used current amount $C_2$ and the like are carried out.

N. Exhaust Device (1) Entire Structure and Function thereof (FIGS. 7 to 9 and 43 to 46)

As described above, chlorine gas is generated around the carbon electrodes 13 in the corrosion test. Most of the chlorine gas is collected and purified by the chlorine gas treating device 6 described above. A portion of the chlorine gas is released out of the aqueous solution of NaCl and flows above the liquid level f. The exhaust device 7 is mounted in the electrolytic test machine to collect the released chlorine gas.

Figure 43:
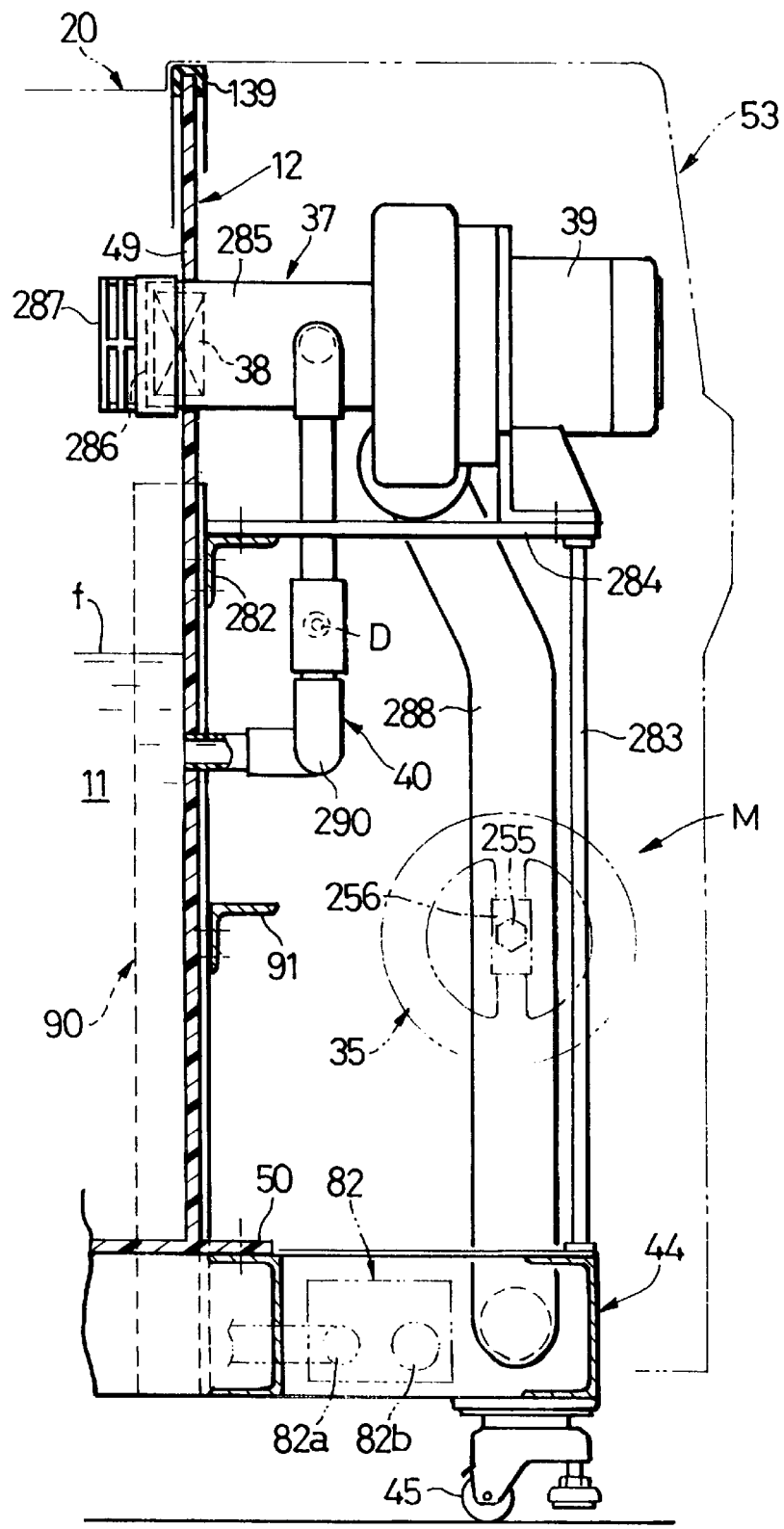
FIG. 43 is a sectional view taken along a line 43—43 in FIG. 9.

As best shown in FIGS. 9 and 43, the exhaust fan 39 of the exhaust device 7 is fixed on a mounting base 284 which is supported by an upper angle member 282 of the frame 90 and a support pillar 283. An intake pipe 285, extending from the inlet of the exhaust fan 39 in the exhaust pipe line 37, is passed through the right sidewall portion 49 of the electrolytic cell 12 to communicate with the inside of the electrolytic cell 12 above the liquid level f of the aqueous solution of NaCl 11. A cap-like grill 287, made of a synthetic resin, is detachably mounted to an inlet 286 of the intake pipe 285. A discharge pipe 288, extending from the outlet of the exhaust fan 39 in the exhaust pipe line 37, extends downwards and opens into the atmosphere in the vicinity of the water dispensing block 82.

On the suction side of the exhaust fan 39 in the exhaust pipe line 37, namely, in the intake pipe 285, an adsorbing member 38 for adsorbing chlorine gas is disposed at an upstream location. A detecting means 40, for detecting an abnormality of the exhaust system, is disposed at a downstream location. The adsorbing member 38 has a structure similar to that of the catalyst unit 219 and hence, includes activated carbon, has a permeability, and is formed into a single unit. When the grill 287 is removed from the inlet 286 of the intake pipe 285, the adsorbing member 38 can be placed into the intake pipe 285 through the inlet 286.

Figure 44:
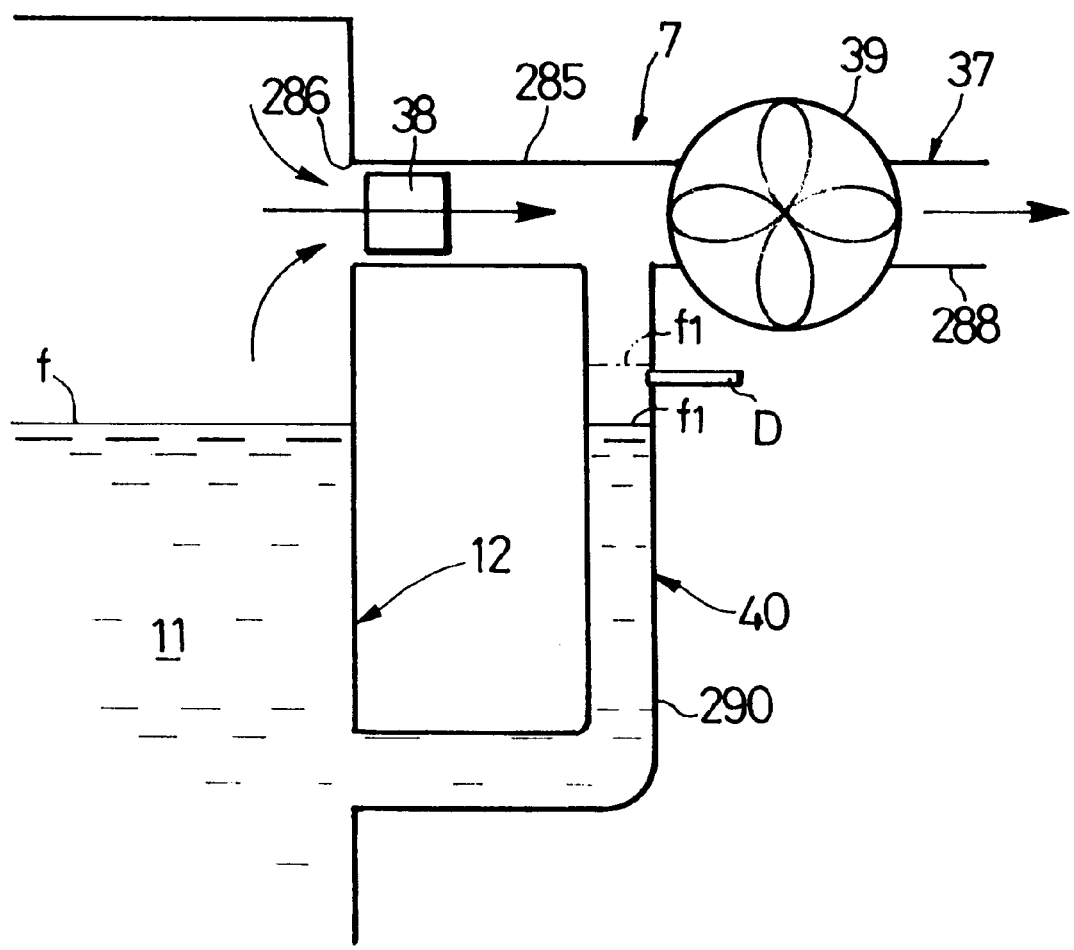
FIG. 44 is a diagram showing one example of an abnormality-generation detecting means in an exhaust system.

The detecting means 40 includes a detecting pipe 290 made of a synthetic resin and mounted between the intake pipe 285 and the electrolytic cell 12, and a water level sensor D mounted in the detecting pipe 290, as best shown in FIGS. 43 and 44. The detecting pipe 290 communicates at its upper end with a downstream portion of the intake pipe 285, and at its lower end with a zone of the electrolytic cell 12 in which the aqueous solution of NaCl 11 is stored. A sensor portion of the water level sensor D is disposed above a liquid level $f_1$ in the detecting pipe 290, which is the same level as the liquid level f in the electrolytic cell 12.

In the above-described construction, if the exhaust fan 39 is operated, the chlorine gas flowing above the liquid level f in the electrolytic cell 12 is adsorbed in the activated carbon when passed through the adsorbing member 38, and thus, clean air is discharged to the atmosphere through the exhaust pipe 288.

Figure 45:
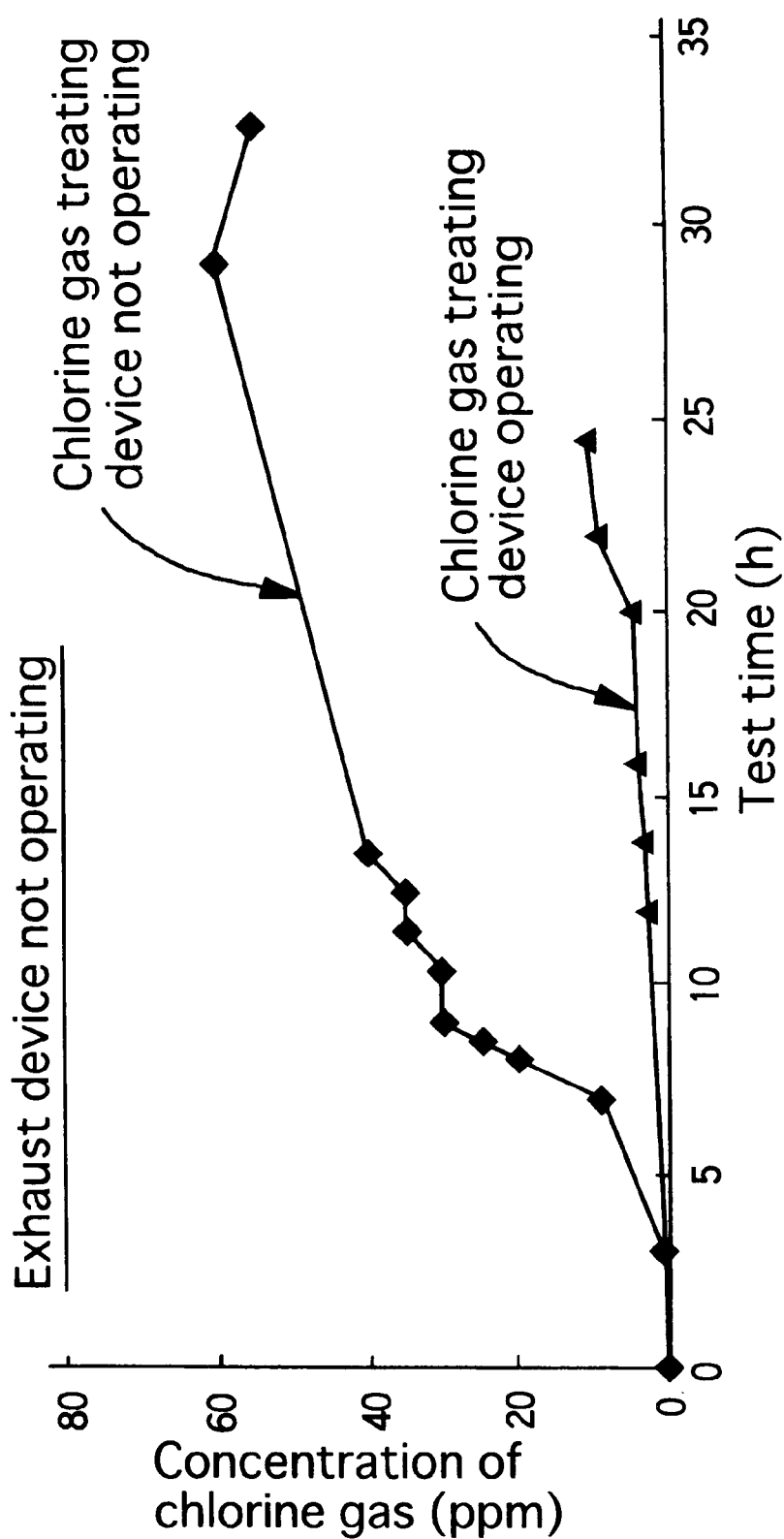
FIG. 45 is a graph illustrating a second example of the relationship between the test time and the concentration of the chlorine gas.

FIG. 45 illustrates the relationship between the test time and the concentration of chlorine gas above the liquid level f within the electrolytic cell 12, a) when the exhaust device 7 was not operated and the chlorine gas treating device 6 described above was operated, and b) when the device 6 was brought into a non-operated state. Test conditions were such that an electric current of 50 A was continuously supplied, the amount of the activated carbon was 550 g (corresponding to the case shown in FIG. 34), and the temperature of the aqueous solution of NaCl 11 was 45° C. As apparent from FIG. 45, if the chlorine gas treating device 6 is operated under the non-operation of the exhaust device 7, the concentration of the chlorine gas can be maintained at an extremely low level, but if the exhaust device 7 is operated, the concentration of the chlorine gas can be further lowered.

To confirm an effect of the exhaust device when activated carbon is used as the adsorbent of the adsorbing member 38, the outlet of the exhaust pipe 288 was put into communication with the inside of the electrolytic cell 12 above the liquid level f in the electrolytic cell 12, and a test, which involves circulating the inside gas above the liquid level f through the adsorbent, was carried out.

Figure 46:
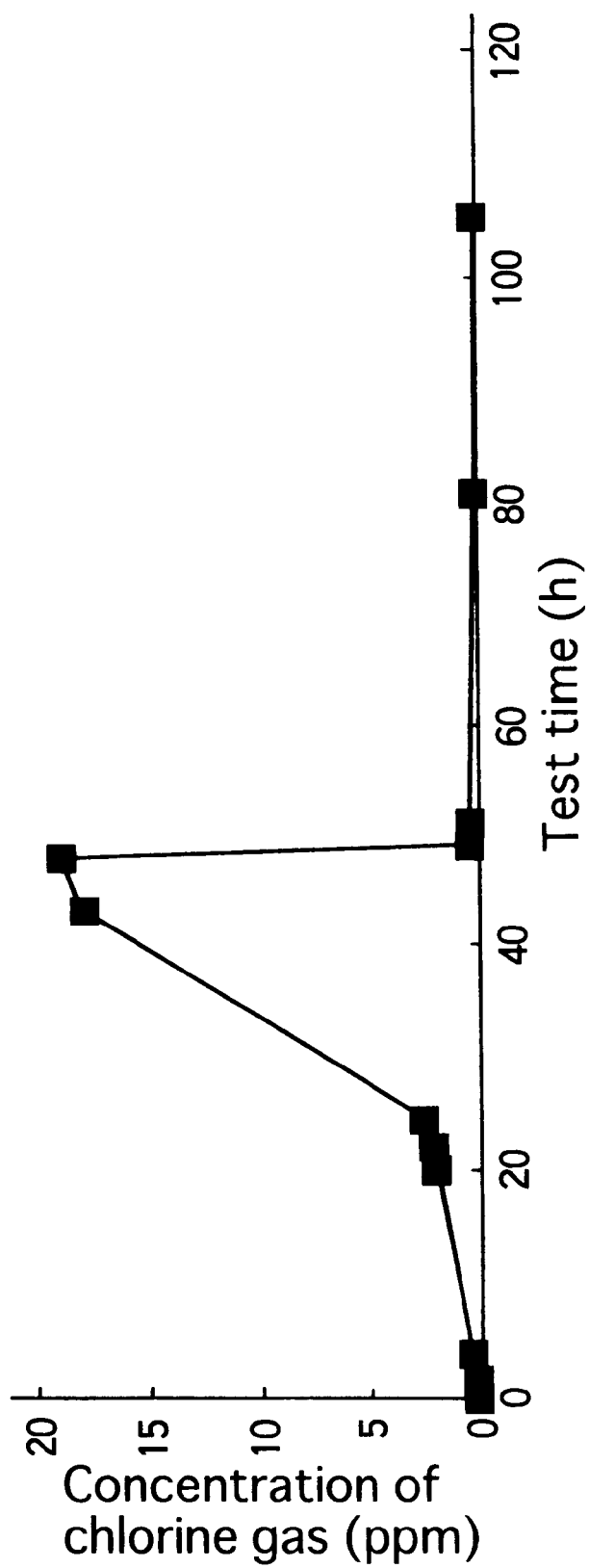
FIG. 46 is a graph illustrating a third example of the relationship between the test time and the concentration of the chlorine gas.

FIG. 46 illustrates the relationship between the test time and the concentration of the chlorine gas above the liquid level f within the electrolytic cell 12. Conditions for the test were such that an electric current of 20 A was continuously supplied, the amount of the activated carbon was 550 g (corresponding to the case shown in FIG. 34), and the temperature of the aqueous solution was 45° C. In this case, the exhaust fan 39 was not operated for a period from the start of the test until the test time reached 50 hours. The concentration of the chlorine gas relatively steeply rose for such a period and reached about 18 ppm after a lapse of 50 hours. If the exhaust fan 39 was operated thereafter, the concentration of chlorine gas was extremely decreased by the purifying effect of the adsorbent and eventually reached 0.5 ppm or less. Thus, with use of the exhaust device 7 having one end of the exhaust pipe 288 open to the atmosphere, the concentration of the chlorine gas above the liquid level f within the electrolytic cell 12 and the concentration of the chlorine gas discharged to the atmosphere are further decreased and suppressed at least to 0.5 ppm or less.

In the above-described construction, for example, if the adsorbing member 38 is operating normally, a corresponding negative pressure is generated in the downstream portion of the intake pipe 285, and the liquid level $f_1$ within the detection pipe 290 rises to a level equal to or higher than the position of the water level sensor D due to the negative pressure, as shown by a dashed line in FIG. 44. Thus, the water level sensor D detects that the exhaust system is operating normally. On the other hand, during replacement of the adsorbing member 38, if a new adsorbing member 38 is not disposed within the intake pipe 285 such as due to forgetting to mount a replacement adsorbing member 38, the negative pressure is considerably lower than under normal operating conditions. Therefore, the liquid level $f_1$ is below the water level sensor D, and this state is detected by the water level sensor D.

According to such a construction, an abnormality of the exhaust system can be easily and reliably detected.

(2) Abnormal-point Detector for Exhaust System (FIGS. 4 to 6, 47A, 47B to 49)

Figure 47A:
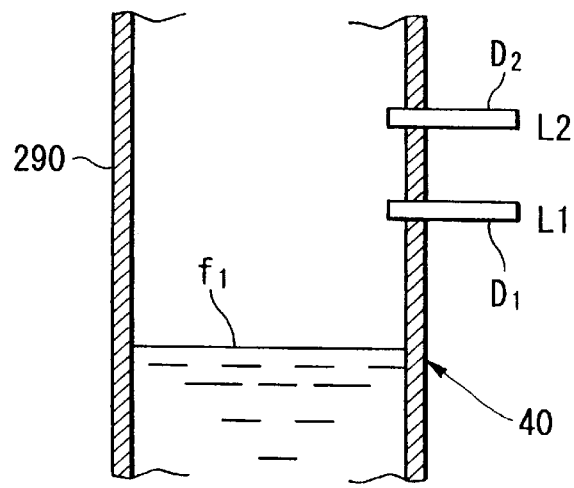
FIG. 47A is a diagram for explaining the positions of liquid level sensors disposed in the abnormal-point detector in the exhaust system.
Figure 47B:
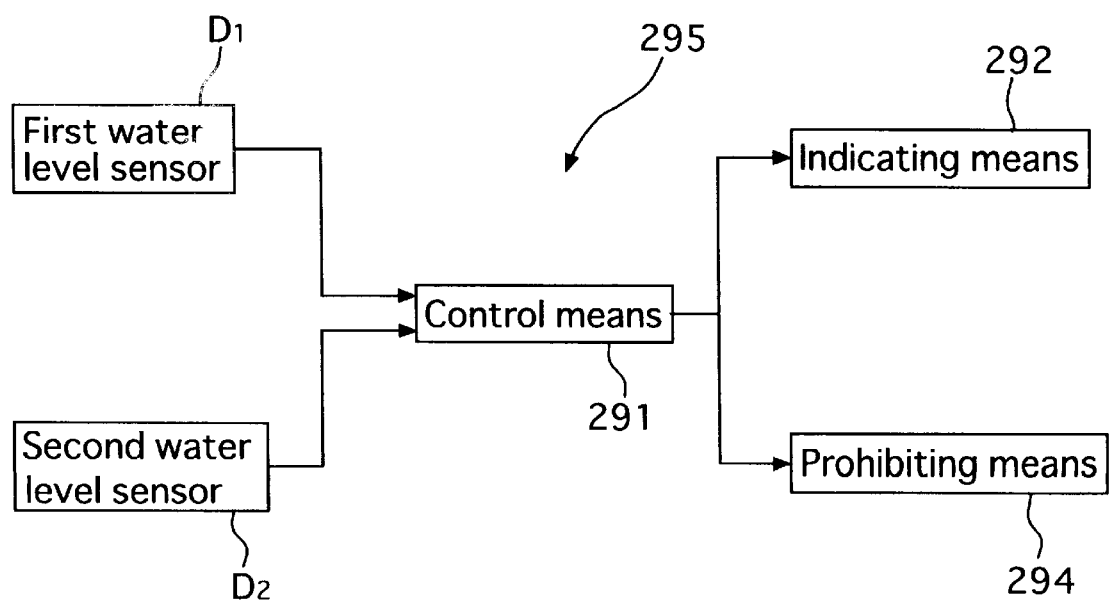
FIG. 47B is a block diagram of the abnormal-point detector in the exhaust system.
Figure 49:
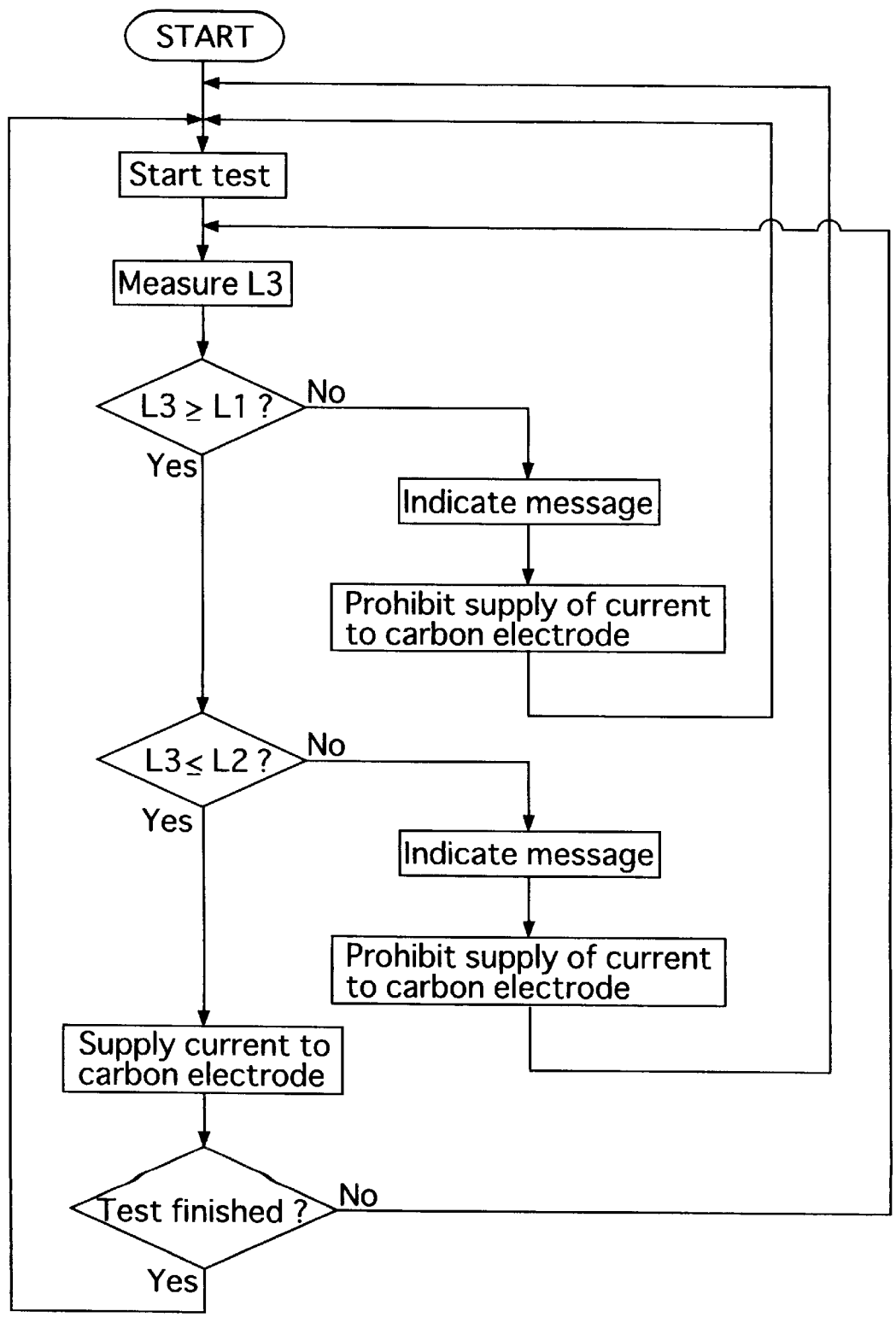
FIG. 49 is a flow chart illustrating the operation of the abnormal-point detector.

As shown in FIGS. 47A and 47B, the detecting means 40 transmits an abnormality signal which varies depending upon the type of abnormality of the exhaust system. First and second water level sensors $D_1$ and $D_2$ are disposed at locations indicating the lower limit value L1 and the upper limit value L2 of the water level L in the detection pipe 290, respectively. A control means 291 is connected to the first and second water level sensors $D_1$ and $D_2$ in the detecting means 40 and discriminates the type of abnormality based on the abnormality signals from the first and second water level sensors $D_1$ and $D_2$. The control means 291 transmits an output signal corresponding to the type of abnormality. An indicating means 292 is connected to the control means 291 and indicates the type of abnormality in accordance with the output signal from the control means 291. A prohibiting means 294 is connected to the control means 291 and prohibits electric current to be supplied to the carbon electrodes 13 based upon the output signal from the control means 291.

These means 291, 292 and 294 are incorporated in the computer programmed control unit 10 to constitute an abnormal-point detector 295 for the exhaust system together with the first and second water level sensors $D_1$ and $D_2$. The indicating means 292 indicates, for example, a message, which is displayed by characters on a liquid crystal display plate 131 mounted on the upper surface of the left cover section 52 covering the control section C, as best shown in FIGS. 4 to 6. The prohibiting means 294 is operated to maintain the DC power source 9 in its OFF state.

As shown in FIGS. 47A, 47B, 48 and 49, if a signal indicative of a command to start the test is input, one of the first and second water level sensors $D_1$ and $D_2$ detects a water level depending upon the negative pressure in the intake pipe 285. If the detected water level $L_3$ is in an acceptable range of $L_1 \leq L_3 < L_2$, the first water level sensor $D_1$ is in its ON state, and the control means 291 determines that the first water level sensor $D_1$ is transmitting a normal condition signal. Therefore, an electric current is supplied to the carbon electrodes 13 to start the corrosion test.

If the detected water level $L_3$ is lower than $L_1$, the first water level sensor $D_1$ is in its OFF state, and the control means 291 determines that the first water level sensor $D_1$ is not transmitting the normal condition signal. That is, the sensor $D_1$ is transmitting an abnormality signal, which corresponds to the non-mounting of the adsorbing member 38 and the non-operation of the exhaust fan 39, whereby the control means 291, transmits a corresponding output signal. Thus, a message "stop the test because of the non-mounting of the adsorbing member 38 or the non-operation of the exhaust fan 39" is indicated by the indicating means 292, and current supply to the carbon electrodes 13 is prohibited by the prohibiting means 294.

If the detected water level $L_3$ is equal to or higher than $L_2$, the second water level sensor $D_2$ is in its ON state, and the control means 291 determines that the second water level sensor $D_2$ is transmitting an abnormality signal, which corresponds to indicating that the adsorbing member 38 is clogged. The control means 291 transmits a corresponding output signal. Thus, because the adsorbing member 38 is clogged, a message "stop the test because of the clogging of the adsorbing member 38" is indicated by the indicating means 292, and the current supply to the carbon electrodes 13 is prohibited by the prohibiting means 294.

The abnormal-point detector 295 for the exhaust system is controlled so that it is operated even during the corrosion test.

The detector 295 enables problems on the exhaust system to be easily and reliably detected so that testing personnel can be informed thereof. In addition, the detector 295 has a simple construction and hence, is relatively inexpensive.

Only the indicating means 292 may be connected to the control means 291. In addition, in place of the water level sensors $D_1$ and $D_2$, a diaphragm-type negative pressure sensor, an air flow sensor, a wind speed sensor or the like may be used.

Figure 50:
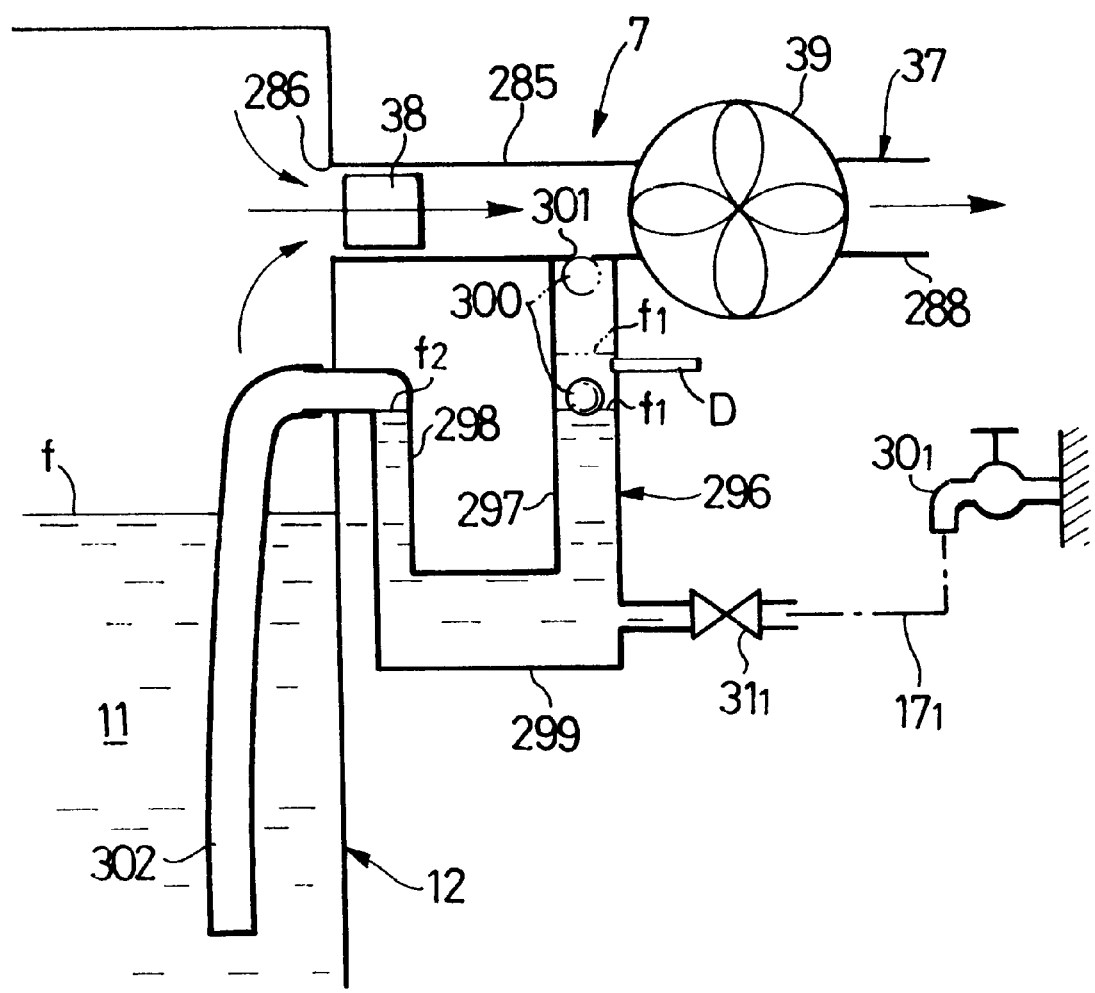
FIG. 50 is a diagram showing another example of an abnormallty-generation detecting means in the exhaust system.

(3) Modification to Exhaust Device (FIG. 50)

A detection pipe 296, made of the synthetic resin, is comprised of first and second pipe portions 297 and 298 extending vertically, and a third pipe portion 299 which connects lower ends of the first and second pipe portions 297 and 298 to each other. An upper end of the first pipe portion 297 communicates with the downstream portion of the intake pipe 285, and an upper folded end of the second pipe portion 298 communicates with the first pipe portion 297 at a location lower than the upper end of the first pipe portion 297. A water supply pipe line $17_1$, which is made of a synthetic resin pipe material, is connected to the third pipe portion 299 and is also connected to a cock $30_1$ of a water service inlet.

A water level sensor D, similar to the sensor described above, is mounted in the first pipe portion 297 to lie above the liquid level $f_1$. A float valve 300 is accommodated in the first pipe portion 297. A valve seat 301 of the float valve 300 is formed at a communication portion of the first pipe portion 297 with the intake pipe 285.

A tube 302, made of a soft synthetic resin, is connected to the upper end of the second pipe portion 298, and extends into the electrolytic cell 12. The tube 302 is used for supplying water to the electrolytic cell 12 and for washing the electrolytic cell 12.

A solenoid valve $31_1$, similar to the solenoid valve 31 described above, is mounted at an intermediate portion of the water supply pipe line $17_1$. The water supply pipe line 17 in the above-described example is eliminated by mounting of the water supply pipe line $17_1$.

Water is supplied to the electrolytic cell 12 through the detection pipe 296 from the water supply pipe line $17_1$. The liquid level $f_1$ in the first pipe portion 297 is defined at the same position as a liquid level $f_2$ at the upper folded portion of the second pipe portion 298 by water flowing from the upper folded end of the second pipe portion 298 into the electrolytic cell 12.

During supplying of water to the electrolytic cell 12, if water substantially fills up the first pipe portion 297 due to the force of water, the clogging of the tube 302 or the like, the float valve 300 is seated onto the valve seat 301 to prevent water from flowing toward the exhaust fan 39. The same is true when the inside of the electrolytic cell 12 is washed through the tube 302.

A sensor portion of the water level sensor D is immersed in tap water when the liquid level $f_1$ rises. Hence, the sensor portion can be kept clean, The chlorine gas flowing above the liquid level f in the electrolytic cell 12 is prevented from leaking to the outside by a trap effect of the detecting pipe 296.

O. Overflow Device having Adsorbing Function (FIGS. 7, 8, 13, 14 and 51)

The overflow device 8 is mounted in the electrolytic test machine 1 in order to discharge an extra amount of the aqueous solution of NaCl when the amount of the aqueous solution of NaCl 11 exceeds a defined value due to a problem with the water level sensor 15 which is placed in the electrolytic cell 12 on the intake side corresponding to the exhaust device 7.

Figure 51:
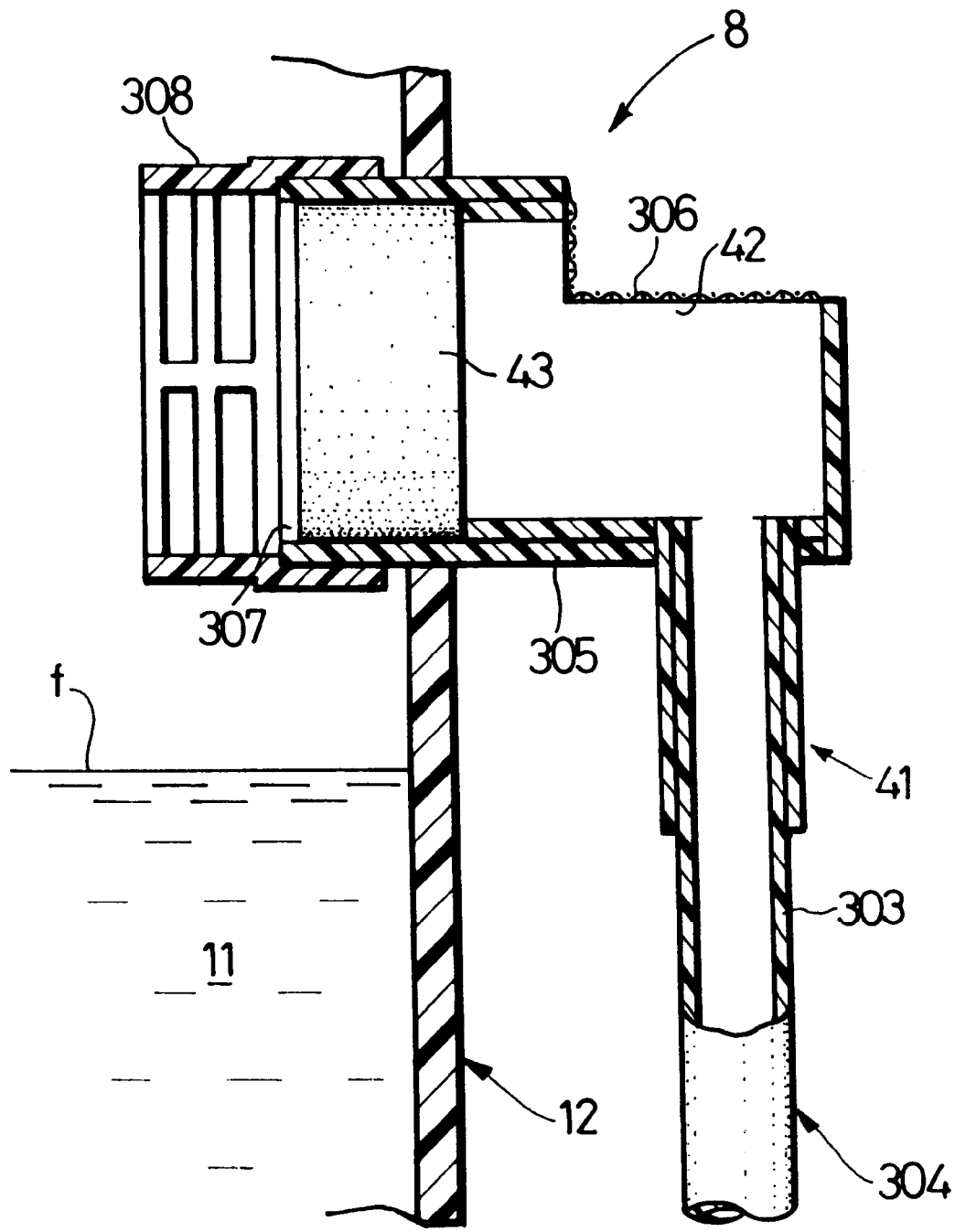
FIG. 51 is a sectional view taken along a line 51—51 in FIG. 7.

As best shown in FIGS. 8, 13 and 51, the overflow pipe 41 is comprised of a folded pipe section 304 having a vertical portion 303 extending along the outer surface of the rear wall portion 71 of the electrolytic cell 12, and a horizontal inlet-side pipe section 305 which is connected to an upper end of the vertical portion 303 and which has a diameter larger than that of the vertical portion 303. The horizontal inlet-side pipe section 305 passes through the rear wall portion 71 of the electrolytic cell 12 and is connected to the space above the liquid level f. As shown in FIGS. 8 and 14, the folded pipe portion 304 is connected at its lower end to the drainage portion 82b of the water dispensing block 82.

In a portion of the inlet pipe section 305 which protrudes from the electrolytic cell 12, substantial half of the inlet pipe section 305 is notched from an outer end to an intermediate portion, so that the inlet pipe section 305 is also used as an intake pipe. Thus, the gas intake port 42 is defined in the inlet pipe section 305. A net 306, for removing foreign matter, is mounted on a peripheral portion of the gas intake port 42 to cover the gas intake port 42.

The adsorbing member 43 for adsorbing the chlorine gas is disposed in the inlet pipe section 305 at a place closer to an inlet 307 than to the gas intake port 42. The adsorbing member 43 has a structure similar to that of the catalyst unit 219 and hence, includes activated carbon, has an air/water permeability and is formed as a single unit. Therefore, a cap-like grill 308, made of a synthetic resin, is attachable to and detachable from the inlet 307 of the inlet pipe section 305. When the grille 305 is removed from the inlet pipe section 305, the adsorbing member 43 can be placed into the inlet pipe section 305 through the inlet 307.

In the above-described construction, if the amount of the aqueous solution of NaCl 11 within the electrolytic cell 12 exceeds the defined value, the extra amount of the aqueous solution is discharged from the inlet 307 through the adsorbing member 43 and the overflow pipe 41 to the water dispensing block 82. In this case, the aqueous solution of NaCl 11 flows in the lower portion of the inlet pipe section 305 and hence, the solution does not flow out from the gas intake port 42.

The suction of the gas into the electrolytic cell 12, produced by the operation of the exhaust device 7, is performed through the gas intake port 42 and the inlet pipe section 305. The chlorine gas, which flows above the liquid level f during non-operation of the exhaust device 7, is inhibited from leaking out of the electrolytic cell 12 by the adsorbing member 43.

P. Other Example of Determining Device for Determining Timing of Replacement of Carbon Electrode (FIGS. 4 to 6, 52 and 53)

Figure 52:
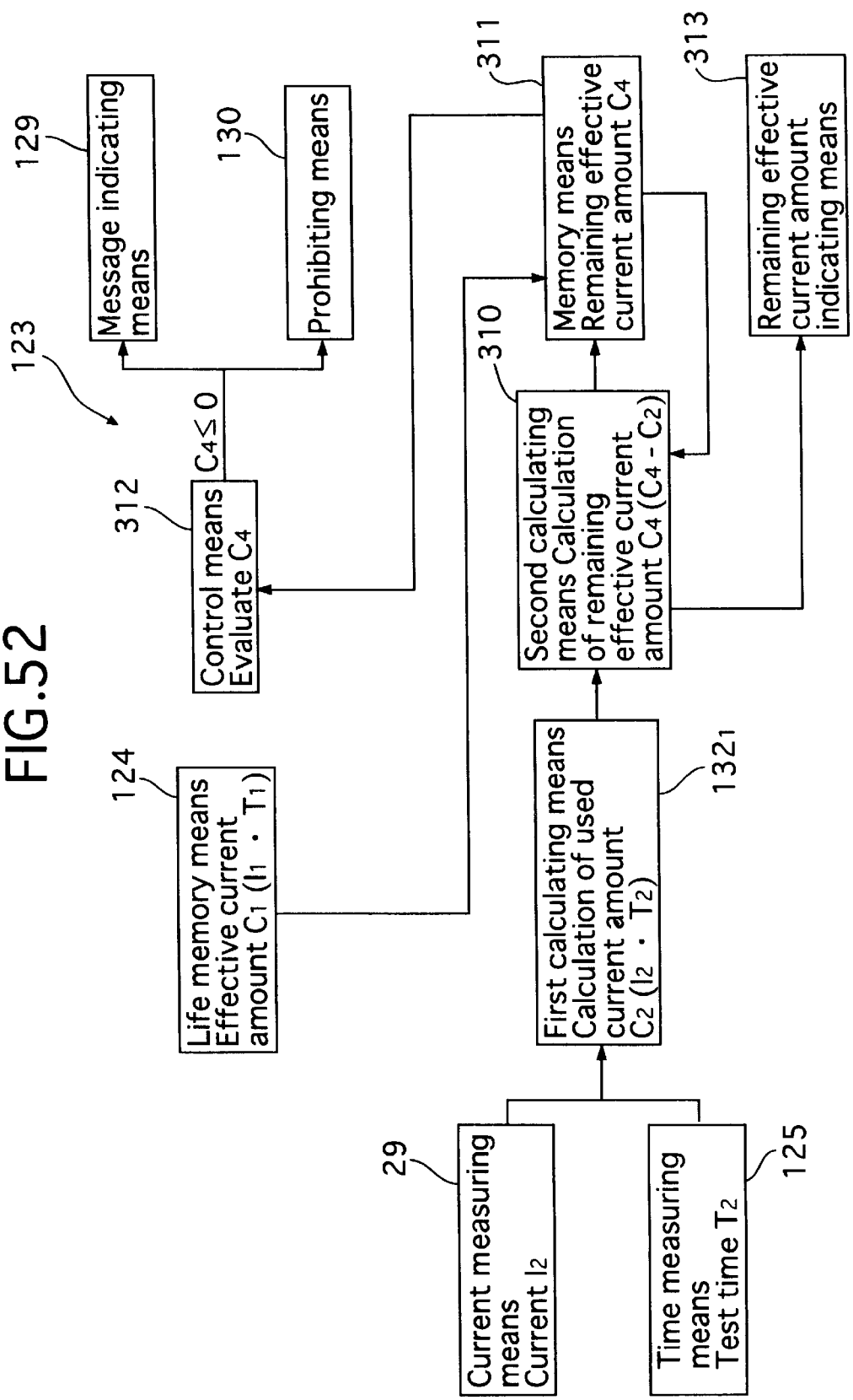
FIG. 52 is a block diagram showing another example of a determining device for determining a replacement time of the carbon electrode.
Figure 53:
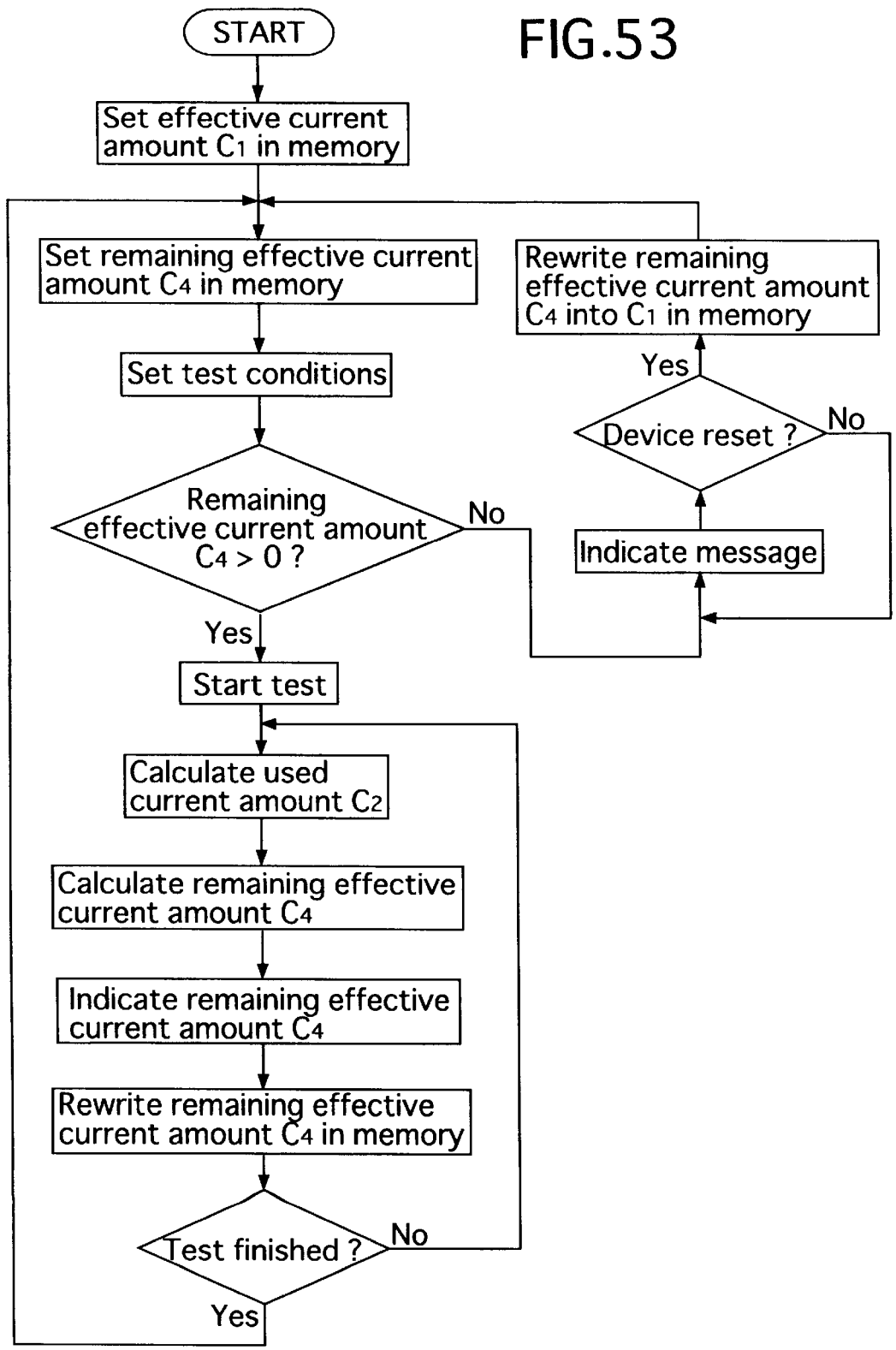
FIG. 53 is a flow chart illustrating the operation of the other example of the determining device for determining the replacement time of the carbon electrode.

FIG. 52 is a block diagram of the determining device 123 and FIG. 53 is a flow chart illustrating the operation of the determining device 123. The term "set test conditions" in FIG. 53 means that any of the following conditions are selected: a) the corrosion test including the coating film peeling-off step and the steel plate corroding step, b) the coating film peeling-off test, and c) the test is to be finished. Conditions selected are then input.

Referring to FIG. 52, the determining device 123 includes a life storing means 124 for storing a service life of the carbon electrode 13 as an effective current amount $C_1$ which is product $I_1 \cdot T_1$ of a certain current $I_1$ flowing across the carbon electrode 13 and a total test time $T_1$ usable when the current $I_1$ continues to flow. A memory means 311 stores the effective current amount $C_1$ as a remaining effective current amount $C_4$. A current measuring means (ammeter) 29 measures a current $I_2$ flowing across the carbon electrode 13 during a test. A time measuring means 125 measures a test time $T_2$. A first calculating means $132_1$ calculates a used current amount $C_2$ which is a product $I_2 \cdot T_2$ of the current $I_2$ and the test time $T_2$. A second calculating means 310 subtracts the used current amount $C_2$ from the remaining effective current amount $C_4$ to provide a new remaining effective current amount and stores it in the memory means 311. A control means 312 evaluates the remaining effective current amount $C_4$ at the start of the test and transmits an electrode replacing signal when $C_4 \leq 0$.

If the determining device 123 is constructed in the above manner, it is possible to automatically detect the replacement time, as the service life of the carbon electrode 13, which is a consumable electrode, reaches the end of its service life.

In this case, even if the remaining effective current amount $C_4$ is smaller than 0, the test is continued. This is permitted by depending on a margin of the effective current amount $C_1$ corresponding to several runs of the test.

The determining device 123 also includes a) a message indicating means 129 adapted to inform testing personnel that the replacement time of the electrode has been reached, based on the electrode replacing signal from the control means 312, and b) a prohibiting means 130 for prohibiting current to be supplied to the carbon electrode 13.

As best shown in FIGS. 4 to 6, the message provided by the message indicating means 129 is displayed by characters on the display plate 131 mounted on the upper surface of the left cover section 52 covering the control section C as described above. The prohibiting means 130 is operated to maintain the DC power source 9 in its OFF state. Thus, testing personnel can reliably know the replacement time of the carbon electrode 13.

As shown in FIG. 53, the determining device 123 is constructed so that the device 123 will not operate unless the remaining effective current amount $C_4$ stored in the memory means 311 is reset to a relation of $C_4 = C_1$.

If the remaining effective current amount $C_4$ is larger than 0 prior to starting the test, the test is started, and the calculation and the integration of the used current amount $C_2$ and the like are carried out.

The determining device 123 includes a remaining effective current amount indicating means 313 for indicating the remaining effective current amount $C_4$ of the carbon electrode 13. The remaining effective current amount $C_4$ indicated by the remaining effective current amount indicating means 313 is displayed as a bar graph on the liquid crystal display plate 131 such that the remaining effective current amount $C_4$ is gradually decreased, as shown in FIG. 24, as described above. Thus, testing personnel can easily know the remainder and varying situation of the service life of the carbon electrode 13.

Q. Another Example of Determining Device for Determining Timing of Replacement of Catalyst (FIGS. 4 to 6, 54 and 55)

Figure 54:
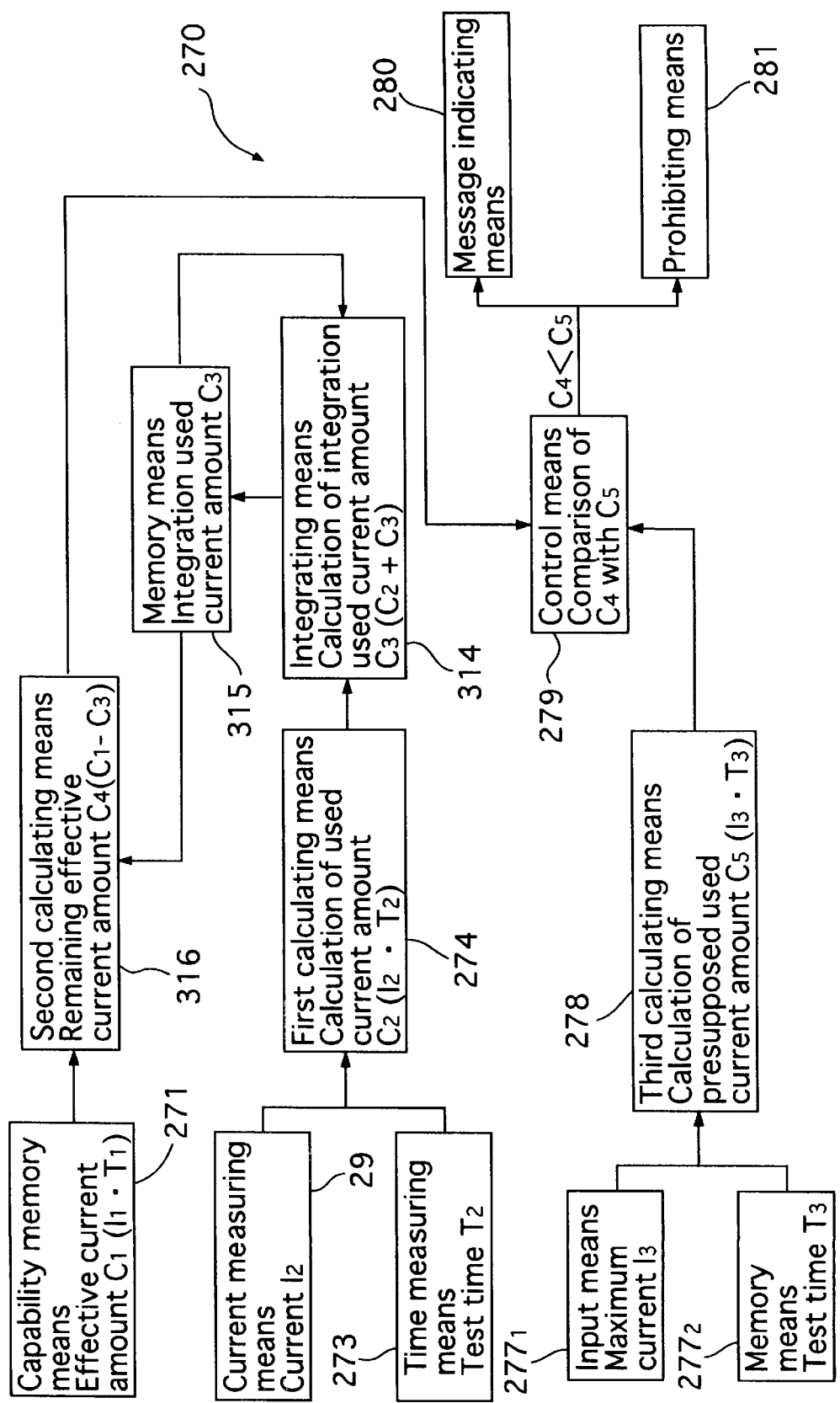
FIG. 54 is a block diagram showing another example of a determining device for determining a replacement time of the catalyst.
Figure 55:
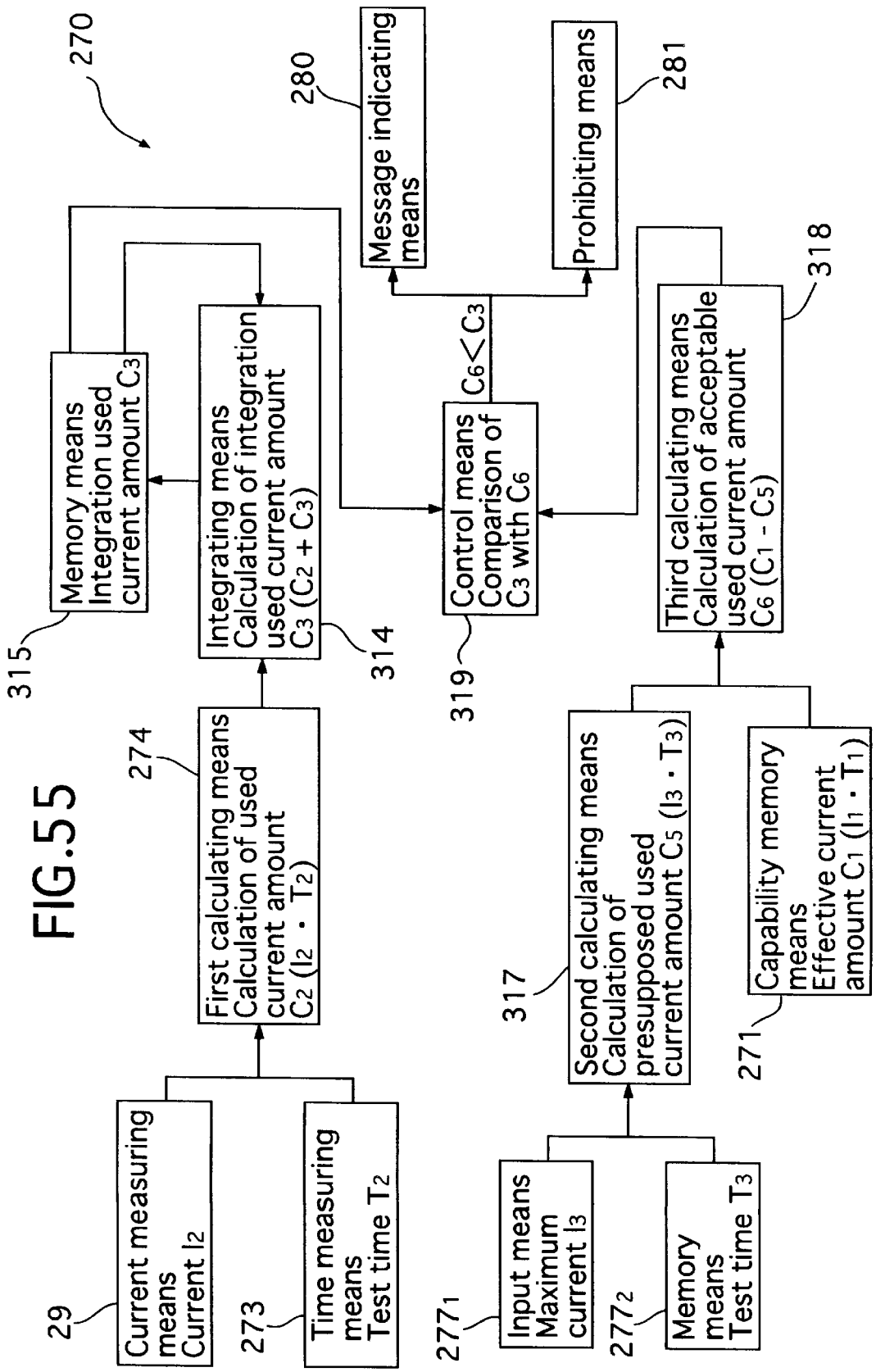
FIG. 55 is a block diagram showing a further example of a determining device for determining a replacement time of the catalyst.

(1) Referring to FIG. 54, the determining device 270 includes a capability storing means 271 for storing a purifying capability of an activated carbon 226 as an effective current amount $C_1$ which is a product $I_1 \cdot T_1$ of a certain current $I_1$ flowing across the carbon electrode 13 and a total test time $T_1$ usable when the current $I_1$ continues to flow. A current measuring means (ammeter) 29 measures a current $I_2$ flowing across the carbon electrode 13 during a test. A time measuring means 273 measures a test time $T_2$. A first calculating means 274 calculates a used current amount $C_2$ which is a product $I_2 \cdot T_2$ of the current $I_2$ and the test time $T_2$. An integrating means 314 integrates the used current amount $C_2$. A memory means 315 stores the integration used current amount $C_3$. A second calculating means 316 subtracts the integration used current amount $C_3$ from the effective current amount $C_1$ to provide a remaining effective current amount $C_4$. An input means $277_1$ inputs a maximum current $I_3$ in the DC power source 9 at the start of the test. A memory means $277_2$ stores a test time $T_3$. A third calculating means 278 calculates a presupposed used current amount $C_5$ which is a product $I_3 \cdot T_3$ of the maximum current $I_3$ and the test time $T_3$. A control means 279 compares the remaining effective current amount $C_4$ and the presupposed used current amount $C_5$ with each other and transmits a catalyst replacing signal when $C_4 < C_5$.

If the determining device 270 is constructed in the above manner, it is possible before the test is carried out to automatically detect that the replacement time of the activated carbon has been reached due to a decrease in purifying capability of the activated carbon 226.

The determining device 270 also includes a) a message indicating means 280 adapted to inform testing personnel that the replacement time of the electrode has been reached, based on the catalyst replacing signal from the control means 279, and b) a prohibiting means 281 for prohibiting current to be supplied to the carbon electrode 13.

As best shown in FIGS. 4 to 6, the message provided by the message indicating means 280 is displayed by characters on the display plate 131 mounted on the upper surface of the left cover section 52 covering the control section C such as described above. The prohibiting means 281 is operated to maintain the DC power source 9 in its OFF state. Thus, testing personnel can reliably know the replacement time of the activated carbon electrode 13.

The determining device 270 is constructed such that the device 270 will not operate unless the integration used current amount $C_3$ is reset in the memory means 315 to 0 after the catalyst unit 219 is replaced.

If the acceptable used current amount $C_6$ and the integration used current amount $C_3$ are in a relation of $C_6 \geq C_3$ prior to starting the test, the test is started, and the integration of the used current amount $C_2$ and the like are carried out.

Although the embodiments of the present invention have been described in detail, it will be understood that the present invention is not limited to the above-described embodiments, and various modifications may be made without departing from the spirit and scope of the invention defined in the claims.

What is claimed is:

1. An electrolytic test machine comprising:

an electrolytic cell in which an aqueous solution of NaCl is stored so that a test material is immersed in the aqueous solution of NaCl;

an electrode immersed in the aqueous solution of NaCl;

a DC power source for supplying electric current between said electrode and said test material;

a chlorine gas treating device for collection, out of the aqueous solution of NaCl, a) chlorine gas which is generated around said electrode with electrolysis of the aqueous solution of NaCl and b) aqueous solution of NaCl;

a chlorine gas collecting hood which covers a portion of said electrode, wherein said chlorine gas collecting hood is entirely disposed within the aqueous solution of NaCl; and a suction port is located below said chlorine gas collecting hood.

2. An electrolytic test machine according to claim 1, wherein said chlorine gas treating device includes a treating pipe line leading to said suction port, a suction pump disposed in said treating pipe line, and a chlorine gas purifying member disposed in said treating pipe line and said chlorine gas purifying member having a catalyst which decomposes NaClO and HClO which are reaction products in a test.

3. An electrolytic test machine according to claim 2, further including an NaOH introducing device mounted in said electrolytic cell for introducing NaOH, produced in a test material immersion zone within said electrolytic cell, to said electrode immersion zone.

4. An electrolytic test machine according to claim 2, wherein said suction port is inclined.

5. An electrolytic test machine according to claim 1, further including an NaOH introducing device mounted in said electrolytic cell for introducing NaOH, produced in a test material immersion zone within said electrolytic cell, to an electrode immersion zone.

6. An electrolytic test machine according to claim 1, wherein said chlorine gas collecting hood has an inclined roof.

* * * * *